(12) United States Patent
von Deyn et al.

(10) Patent No.: US 7,608,564 B2
(45) Date of Patent: Oct. 27, 2009

(54) 3-HETEROCYCLYL-SUBSTITUTED BENZOYL DERIVATIVES

(75) Inventors: Wolfgang von Deyn, Neustadt (DE); Regina Luise Hill, Speyer (DE); Uwe Kardorff, Mannheim (DE); Ernst Baumann, Dudenhofen (DE); Stefan Engel, Idstein (DE); Guido Mayer, Neustadt (DE); Matthias Witschel, Ludwigshafen (DE); Michael Rack, Heidelberg (DE); Norbert Götz, Worms (DE); Joachim Gebhardt, Wachenheim (DE); Ulf Mißlitz, Neustadt (DE); Helmut Walter, Obrigheim (DE); Karl-Otto Westphalen, Speyer (DE); Martina Otten, Ludwigshafen (DE); Joachim Rheinheimer, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/739,928

(22) Filed: Apr. 25, 2007

(65) Prior Publication Data

US 2008/0039327 A1 Feb. 14, 2008

Related U.S. Application Data

(62) Division of application No. 09/748,006, filed on Dec. 27, 2000, now Pat. No. 7,232,792, which is a division of application No. 09/091,300, filed as application No. PCT/EP98/00069 on Jan. 8, 1998.

(30) Foreign Application Priority Data

Jan. 17, 1997 (DE) ................ 197 01 446

(51) Int. Cl.
*A01N 43/76* (2006.01)
*C07D 263/02* (2006.01)

(52) U.S. Cl. ............... 504/270; 504/271; 548/215; 548/240

(58) Field of Classification Search ........... 548/215, 548/240; 504/270, 271
See application file for complete search history.

(56) References Cited

U.S. PATENT DOCUMENTS

| | | | |
|---|---|---|---|
| 4,070,536 A | 1/1978 | Konotsune et al. | |
| 4,687,858 A | 8/1987 | Konotsune et al. | |
| 4,948,887 A | 8/1990 | Baba et al. | |
| 4,986,845 A | 1/1991 | Oya et al. | |
| 5,846,907 A | 12/1998 | von Deyn et al. | |
| 6,147,031 A | 11/2000 | Adachi et al. | |
| 6,479,437 B1 | 11/2002 | Bratz et al. | |
| 6,613,719 B1 * | 9/2003 | Kudis et al. | 504/271 |
| 6,713,436 B1 * | 3/2004 | Neidlein et al. | 504/271 |
| 6,831,039 B1 * | 12/2004 | Neidlein et al. | 504/280 |
| 7,232,792 B2 * | 6/2007 | von Deyn et al. | 504/266 |

FOREIGN PATENT DOCUMENTS

| | | |
|---|---|---|
| EP | 203 428 | 12/1986 |
| WO | WO-96/26206 A1 | 8/1996 |
| WO | WO-97/41105 | 11/1997 |
| WO | WO-97/46530 | 12/1997 |

* cited by examiner

*Primary Examiner*—Rei-tsang Shiao
(74) *Attorney, Agent, or Firm*—Birch, Stewart, Kolasch & Birch, LLP

(57) ABSTRACT

Benzoyl derivatives of the formula I

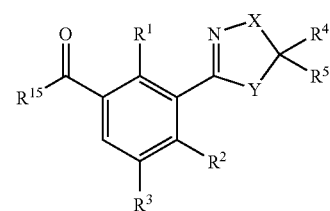

where the variables have the following meanings:
$R^1$, $R^2$ are hydrogen, nitro, halogen, cyano, alkyl, haloalkyl, alkoxy, haloalkoxy, alkylthio, haloalkylthio, alkylsulfinyl, haloalkylsulfinyl, alkylsulfonyl or $C_1$-$C_6$-haloalkylsulfonyl;
$R^3$ is hydrogen, halogen or alkyl;
$R^4$, $R^5$ are hydrogen, halogen, cyano, nitro, alkyl, alkoxy, alkylthio, dialkylamino, phenyl or carbonyl, it being possible for the 6 last-mentioned radicals to be substituted;
X is O, S, $NR^9$, CO or $CR^{10}R^{11}$;
Y is O, S, $NR^{12}$, CO or $CR^{13}R^{14}$;
$R^{15}$ is pyrazole which is unsubstituted or substituted, linked in the 4-position and has attached to it in the 5-position a hydroxyl or sulfonyloxy radical;
and the agriculturally useful salts thereof; processes and intermediates for the preparation of the 3-heterocyclyl-substituted benzoyl derivatives; compositions comprising them; and the use of these derivatives or compositions comprising them for controlling undesirable plants.

15 Claims, No Drawings

3-HETEROCYCLYL-SUBSTITUTED BENZOYL DERIVATIVES

CROSS-REFERENCE TO RELATED APPLICATIONS

The present application is a 37 C.F.R. § 1.53(b) Divisional of U.S. application Ser. No. 09/748,006 filed Dec. 27, 2000, now U.S. Pat. No. 7,232,792 which in turn is a Divisional of U.S. application Ser. No. 09/091,300 filed Jun. 16, 1998 which in turn claims priority of International Application No. PCT/EP98/00069 filed on Jan. 8, 1998. The entire contents of these applications are hereby incorporated by reference.

The present invention relates to 3-heterocyclyl-substituted benzoyl derivatives of the formula I

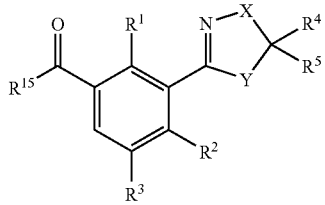

where the variables have the following meanings:

$R^1$, $R^2$ are hydrogen, nitro, halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl or $C_1$-$C_6$-haloalkylsulfonyl;

$R^3$ is hydrogen, halogen or $C_1$-$C_6$-alkyl;

$R^4$, $R^5$ are hydrogen, halogen, cyano, nitro, $C_1$-$C_4$-alkyl, $C_1$-$C_4$-alkoxy-$C_1$-$C_4$-alkyl, di($C_1$-$C_4$-alkoxy)-$C_1$-$C_4$-alkyl, di($C_1$-$C_4$-alkyl)-amino-$C_1$-$C_4$-alkyl, [2,2-di($C_1$-$C_4$-alkyl)-1-hydrazino]-$C_1$-$C_4$-alkyl, $C_1$-$C_6$-alkyliminooxy-$C_1$-$C_4$-alkyl, $C_1$-$C_4$-alkoxycarbonyl -$C_1$-$C_4$-alkyl, $C_1$-$C_4$-alkylthio-$C_1$-$C_4$-alkyl, $C_1$-$C_4$-haloalkyl, $C_1$-$C_4$-cyanoalkyl, $C_3$-$C_8$-cycloalkyl, $C_1$-$C_4$-alkoxy, $C_1$-$C_4$-alkoxy-$C_2$-$C_4$-alkoxy, $C_1$-$C_4$-haloalkoxy, hydroxyl, $C_1$-$C_4$-alkylcarbonyloxy, $C_1$-$C_4$-alkylthio, $C_1$-$C_4$-haloalkylthio, di($C_1$-$C_4$-alkyl)amino, $COR^6$, phenyl or benzyl, it being possible for the two last-mentioned substituents to be fully or partially halogenated and/or to have attached to them one to three of the following groups:
nitro, cyano, $C_1$-$C_4$-alkyl, $C_1$-$C_4$-haloalkyl, $C_1$-$C_4$-alkoxy or $C_1$-$C_4$-haloalkoxy;

or $R^4$ and $R^5$ together form a $C_2$-$C_6$-alkanediyl chain which can be mono-to tetrasubstituted by $C_1$-$C_4$-alkyl and/or which can be interrupted by oxygen or by a nitrogen which is unsubstituted or substituted by $C_1$-$C_4$-alkyl;

or $R^4$ and $R^5$ together with the corresponding carbon form a carbonyl or thiocarbonyl group;

$R^6$ is hydrogen, $C_1$-$C_4$-alkyl, $C_1$-$C_4$-haloalkyl, $C_1$-$C_4$-alkoxy, $C_1$-$C_4$-alkoxy-$C_2$-$C_4$-alkoxy, $C_1$-$C_4$-haloalkoxy, $C_3$-$C_6$-alkenyloxy, $C_3$-$C_6$-alkynyloxy or $NR^7R^8$;

$R^7$ is hydrogen or $C_1$-$C_4$-alkyl;

$R^8$ is $C_1$-$C_4$-alkyl;

x is O, S, $NR^9$, CO or $CR^{10}OR^{11}$;

Y is O, S, $NR^{12}$, CO or $CR^{13}R^{14}$;

$R^9$, $R^{12}$ are hydrogen or $C_1$-$C_4$-alkyl;

$R^{10}$, $R^{11}$, $R^{13}$, $R^{14}$ are hydrogen, $C_1$-$C_4$-alkyl, $C_1$-$C_4$-haloalkyl, $C_1$-$C_4$-alkoxycarbonyl, $C_1$-$C_4$-haloalkoxycarbonyl or $CONR^7R^8$;

or $R^4$ and $R^9$ or $R^4$ and $R^{10}$ or $R^5$ and $R^{12}$ or $R^5$ and $R^{13}$ together form a $C_2$-$C_6$-alkanediyl chain which can be mono- to tetrasubstituted by $C_1$-$C_4$-alkyl and/or interrupted by oxygen or by a nitrogen which is unsubstituted or substituted by $C_1$-$C_4$-alkyl;

$R^{15}$ is a pyrazole of the formula II which is linked in the 4-position

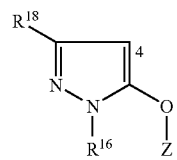

where $R^{16}$ is $C_1$-$C_6$-alkyl;

Z is H or $S_2R^{17}$;

$R^{17}$ is $C_1$-$C_4$-alkyl, $C_1$-$C_4$-haloalkyl, phenyl or phenyl which is partially or fully halogenated and/or has attached to it one to three of the following groups:

nitro, cyano, $C_1$-$C_4$-alkyl, $C_1$-$C_4$-haloalkyl, $C_1$-$C_4$-alkoxy or C1-C4-haloalkoxy;

$R^{18}$ is hydrogen or C1-C6-alkyl;

where X and Y are not simultaneously oxygen or sulfur;

with the exception of 4-[2-chloro-3-(4,5-dihydroisoxazol-3-yl)-4-methylsulfonylbenzoyl]-l-ethyl-5-hydroxy-lH-pyrazole, 4-[2-chloro-3-(4,5-dihydroisoxazol-3-yl)-4-methylsulfonyl-benzoyl]-1,3-dimethyl-5-hydroxy-lH-pyrazole, 4-[2-chloro-3-(5-cyano-4,5-dihydroisoxazol-3-yl)-4-methyl-sulfonylbenzoyl]-1,3-dimethyl-5-hydroxy-lH-pyrazole, 4-[2-chloro-3-(4,5-dihydrothiazol-2-yl)-4-methylsulfonyl-benzoyl]-1,3-dimethyl-5-hydroxy-lH-pyrazole and 4-[2-chloro-3- (thiazoline-4,5-dion-2-yl)-4-methylsulfonyl- benzoyl]-1,3-dimethyl-5-hydroxy-lH- pyrazole;

or the agriculturally useful salts thereof.

The invention furthermore relates to processes and intermediates for the preparation of compounds of the formula I, to compositions comprising them, and to the use of these derivatives or compositions comprising them for the control of harmful plants.

Pyrazol-4-yl-benzoyl derivatives have been disclosed in the literature, for example in WO 96/26206.

However, the herbicidal properties of the compounds which have been known to date and their compatibility properties regarding crop plants are only moderately satisfactory.

It is an object of the present invention to provide novel, in particular herbicidally active, compounds which have improved properties.

We have found that this object is achieved by the 3-heterocyclyl-substituted benzoyl derivatives of the formula I and by their herbicidal activity.

We have furthermore found herbicidal compositions which comprise the compounds I and which have a very good herbicidal activity. Moreover, we have found processes for the preparation of these compositions and methods of controlling undesirable vegetation using the compounds I.

Depending on the substitution pattern, the compounds of the formula I can contain one or more chiral centers, in which case they exist as enantiomer or diastereomer mixtures. The present invention relates to the pure enantiomers or diastereomers and to the mixtures thereof.

The compounds of the formula I may also exist in the form of their agriculturally useful salts, the type of salt generally being of no importance. In general, suitable salts are the salts of those cations or the acid addition salts of those acids whose cations, or anions, respectively, do not adversely affect the herbicidal activity of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, it being possible in this case, if desired, for one to four hydrogen atoms to be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, in addition phosphonium ions, sulfonium ions, preferably tri($C_1$-$C_4$-alkyl)sulfonium and sulfoxonium ions, preferably tri($C_1$-$C_4$-alkyl)sulfoxonium.

Anions of useful acid addition salts are mainly chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate.

The organic moieties mentioned for the substituents $R^1$-$R^{18}$ or as radicals on phenyl rings are collective terms for individual enumerations of the individual group members. All hydrocarbon chains, ie. all alkyl, haloalkyl, cyanoalkyl, alkoxy, haloalkoxy, alkyliminooxy, alkylcarbonyloxy, alkylthio, haloalkylthio, alkylsulfinyl, haloalkylsulfinyl, alkylsulfonyl, haloalkylsulfonyl, alkoxycarbonyl, haloalkoxycarbonyl, alkenyloxy, alkynyloxy, dialkylamino, dialkylhydrazino, alkoxyalkyl, hydroxyalkoxyalkyl, dialkoxyalkyl, alkylthioalkyl, dialkylaminoalkyl, dialkylhydrazinoalkyl, alkyliminooxyalkyl, alkoxycarbonylalkyl and alkoxyalkoxy moieties, can be straight-chain or branched. Unless otherwise specified, halogenated substituents preferably have attached to them one to five identical or different halogen atoms. The meaning of halogen is in each case fluorine, chlorine, bromine or iodine.

Other examples of meanings are:

$C_1$-$C_4$-alkyl and the alkyl moieties of di-($C_1$-$C_4$-alkoxy)-$C_1$-$C_4$-alkyl, [2,2-di($C_1$-$C_4$-alkyl)-1-hydrazino]-$C_1$-$C_4$-alkyl, $C_1$-$C_6$-alkyliminooxy-$C_1$-$C_4$-alkyl, hydroxy-$C_1$-$C_4$-alkoxy-$C_1$-$C_4$-alkyl and $C_1$-$C_4$-alkylcarbonyloxy: for example methyl, ethyl, propyl, 1-methylethyl, butyl, 1-methylpropyl, 2-methylpropyl and 1,1-dimethylethyl;

$C_1$-$C_6$-alkyl: $C_1$-$C_4$-alkyl as mentioned above and, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$-$C_4$-haloalkyl: a $C_1$-$C_4$-alkyl radical as mentioned above which is partially or fully substituted by fluorine, chlorine, bromine and/or iodine, for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$-$C_6$-haloalkyl: $C_1$-$C_4$-haloalkyl as mentioned above and, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$-$C_4$-cyanoalkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl and 2-cyanomethylprop-2-yl;

$C_1$-$C_4$-alkoxy and the alkoxy moieties of di-($C_1$-$C_4$-alkoxy)-$C_1$-$C_4$-alkyl and hydroxy-$C_1$-$C_4$-alkoxy-$C_1$-$C_4$-alkyl: for example methoxy, ethoxy, propoxy, 1-methylethoxy, butoxy, 1-methylpropoxy, 2-methylpropoxy and 1,1-dimethylethoxy;

$C_1$-$C_6$-alkoxy: $C_1$-$C_4$-alkoxy as mentioned above and, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-haloalkoxy: a $C_1$-$C_4$-alkoxy radical as mentioned above which is partially or fully substituted by fluorine, chlorine, bromine and/or iodine, for example fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy: $C_1$-$C_4$-haloalkoxy as mentioned above and, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_6$-alkyliminooxy and the $C_1$-$C_6$-akyliminooxy moieties of $C_1$-$C_6$-alkyliminooxy-$C_1$-$C_4$-alkyl: for example methyliminooxy, ethyliminooxy, 1-propyliminooxy, 2-propyliminooxy, 1-butyliminooxy, 2-butyliminooxy, 2-methylprop-1-yliminooxy, 1-pentyliminooxy, 2-pentyliminooxy, 3-pentyliminooxy, 3-methylbut-2-yliminoxy, 2-methylbut-1-yliminooxy, 3-methylbut-1-yliminooxy, 1-hexyliminooxy, 2-Hexyliminooxy, 3-hexyliminooxy, 2-methylpent-1-yliminooxy, 3-methylpent-1-yliminooxy, 4-methylpent-1-yliminooxy, 2-ethylbut-1-yliminooxy, 3-ethylbut-1-yliminooxy, 2,3-dimethylbut-1-yliminooxy, 3-methylpent-2-yliminooxy, 4-methylpent-2-yliminooxy and 3,3-dimethylbut-2-yliminooxy;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above and, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_4$-haloalkylthio: a $C_1$-$C_4$-alkylthio radical as mentioned above, which is partially or fully substituted by fluorine, chlorine, bromine and/or iodine, for example fluoromethylthio, difluoromethylthio, trifluoromethylthio, chlorodifluoromethylthio, bromodifluoromethylthio, 2-fluorethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$-$C_6$-haloalkylthio: $C_1$-$C_4$-haloalkylthio as mentioned above and, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio and dodecafluorohexylthio;

$C_1$-$C_6$-alkylsulfinyl($C_1$-$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-haloalkylsulfinyl: a $C_1$-$C_6$-alkylsulfinyl radical as mentioned above which is partially or fully substituted by fluorine, chlorine, bromine and/or iodine, for example fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl and dodecafluorohexylsulfinyl;

$C_1$-$C_6$-alkylsulfonyl($C_1$-$C_6$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$-$C_6$-haloalkylsulfonyl: a $C_1$-$C_6$-alkylsulfonyl radical as mentioned above which is partially or fully substituted by fluorine, chlorine, bromine and/or iodine, for example fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$-$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl and 1,1-dimethoxycarbonyl;

$C_1$-$C_4$-haloalkoxycarbonyl: a $C_1$-$C_4$-alkoxycarbonyl as mentioned above which is partially or fully substituted by fluorine, chlorine, bromine and/or iodine, for example fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl and 4-iodobutoxycarbonyl;

$C_3$-$C_6$-alkenyloxy: for example prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, hex-1-en-1-yloxy, hex-2-en-1-yloxy, hex-3-en-1-yloxy, hex-4-en-1-yloxy, hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy and 1-ethyl-2-methylprop-2-en-1-yloxy;

$C_3$-$C_6$-alkynyloxy: for example prop-1-yn-1-yloxy, prop-2-yn-1-yloxy, but-1-yn-1-yloxy, but-1-yn-3-yloxy, but-1-yn-4-yloxy, but-2-yn-1-yloxy, pent-1-yn-1-yloxy, pent-1-yn-3-yloxy, pent-1-yn-4-yloxy, pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, hex-1-yn-1-yloxy, hex-1-yn-3-yloxy, hex-1-yn-4-yloxy, hex-1-yn-5-yloxy, hex-1-yn-6-yloxy, hex-2-yn-1-yloxy, hex-2-yn-4-yloxy, hex-2-yn-5-yloxy, hex-2-yn-6-yloxy, hex-3-yn-1-yloxy, hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy and 4-methylpent-2-yn-5-yloxy;

di($C_1$-$C_4$-alkyl)amino: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

[2,2-di($C_1$-$C_4$-alkyl)-1-hydrazino], and the dialkylhydrazino moieties of [2,2-di($C_1$-$C_4$-alkyl)-1-hydrazino]-$C_1$-$C_4$-alkyl: for example 2,2-dimethylhydrazino-1,2,2-diethylhydrazino-1,2,2-dipropylhydrazino-1,2,2-di(1-methylethyl)-1-hydrazino, 2,2-dibutylhydrazino-1,2,2-di(1-methylpropyl)-1-hydrazino, 2,2-di(2-methylpropyl)-1-hydrazino, 2,2-di(1,1-dimethylethyl)-1-hydrazino, 2-ethyl-2-methyl-1-hydrazino, 2-methyl-2-propyl-1-hydrazino, 2-methyl-2-(1-methylethyl)-1-hydrazino, 2-butyl-2-methyl-1-hydrazino, 2-methyl-2-(1-methylpropyl)-1-hydrazino, 2-methyl-2-(2-methylpropyl)-1-hydrazino, 2-(1,1-dimethylethyl)-2-methyl-1-hydrazino, 2-ethyl-2-propyl-1-hydrazino, 2-ethyl-2-(1-methylethyl)-1-hydrazino, 2-butyl-2-ethyl-1-hydrazino, 2-ethyl-2-(1-methylpropyl)-1-hydrazino, 2-ethyl-2-(2-methylpropyl)-1-hydrazino, 2-ethyl-2-(1,1-dimethylethyl)-1-hydrazino, 2-(1-methylethyl)-2-propyl-1-hydrazino, 2-butyl-2-propyl-1-hydrazino, 2-(1-methylpropyl)-2-propyl-1-hydrazino, 2-(2-methylpropyl)-2-propyl-1-hydrazino, 2-(1,1-dimethylethyl)-2-propyl-1-hydrazino, 2-butyl-2-(1-methylethyl)-1-hydrazino, 2-(1-methylethyl)-2-(1-methylpropyl)-1-hydrazino, 2-(1-methylethyl)-2-(2-methylpropyl)-1-hydrazino, 2-(1,1-dimethylethyl)-2-(1-methylethyl)-1-hydrazino, 2-butyl-2-(1-methylpropyl)-1-hydrazino, 2-butyl-2-(2-methylpropyl)-1-hydrazino, 2-butyl-2-(1,1-dimethylethyl)-1-hydrazino, 2-(1-methylpropyl)-2-(2-methylpropyl)-1-hydrazino, 2-(1,1-dimethylethyl)-2-(1-methylpropyl)-1-hydrazino and 2-(1,1-dimethylethyl)-2-(2-methylpropyl)-1-hydrazino;

di($C_1$-$C_4$-alkyl)amino-$C_1$-$C_4$-alkyl: $C_1$-$C_4$-alkyl which is substituted by di($C_1$-$C_4$-alkyl)amino as mentioned above, for example N,N-dimethylaminomethyl, N,N-diethylaminomethyl, N,N-dipropylaminomethyl, N,N-di(1-methylethyl)aminomethyl, N,N-dibutylaminomethyl, N,N-di(1-methylpropyl)aminomethyl, N,N-di(2-methylpropyl)aminomethyl, N,N-di(1,1-dimethylethyl)aminomethyl, N-ethyl-N-methylaminomethyl, N-methyl-N-propylaminomethyl, N-methyl-N-(1-methylethyl)aminomethyl, N-butyl-N-methylaminomethyl, N-methyl-N-(1-methylpropyl)aminomethyl, N-methyl-N-(2-methylpropyl)aminomethyl, N-(1,1-dimethylethyl)-N-methylaminomethyl, N-ethyl-N-propylaminomethyl, N-ethyl-N-(1-methylethyl)aminomethyl, N-butyl-N-ethylaminomethyl, N-ethyl-N-(1-methylpropyl) aminomethyl, N-ethyl-N-(2-methylpropyl)aminomethyl, N-ethyl-N-(1,1-dimethylethyl)aminomethyl, N-(1-methylethyl)-N-propylaminomethyl, N-butyl-N-propylaminomethyl, N-(1-methylpropyl)-N-propylaminomethyl, N-(2-methylpropyl)-N-propylaminomethyl, N-(1,1-dimethylethyl)-N-propylaminomethyl, N-butyl-N-(1-methylethyl) aminomethyl, N-(1-methylethyl)-N-(1-methylpropyl) aminomethyl, N-(1-methylethyl)-N-(2-methylpropyl) aminomethyl, N-(1,1-dimethylethyl)-N-(1-methylethyl) aminomethyl, N-butyl-N-(1-methylpropyl)aminomethyl, N-butyl-N-(2-methylpropyl)aminomethyl, N-butyl-N-(1,1-dimethylethyl)aminomethyl, N-(1-methylpropyl)-N-(2-methylpropyl)aminomethyl, N-(1,1-dimethylethyl)-N-(1-methylpropyl)aminomethyl, N-(1,1-dimethylethyl)-N-(2-methylpropyl)aminomethyl, 2-(N,N-dimethylamino)ethyl, 2-(N,N-diethylamino)ethyl, 2-(N,N-dipropylamino)ethyl, 2-[N,N-di(1-methylethyl)amino]ethyl, 2-[N,N-dibutylamino]ethyl, 2-[N,N-di(1-methylpropyl)amino]ethyl, 2-[N,N-di(2-methylpropyl)amino]ethyl, 2-[N,N-di(1,1-dimethylethyl)amino]ethyl, 2-[N-ethyl-N-methylamino]ethyl, 2-[N-methyl-N-propylamino]ethyl, 2-[N-methyl-N-(1-methylethyl)amino]ethyl, 2-[N-butyl-N-methylamino]ethyl, 2-[N-methyl-N-(1-methylpropyl)amino]ethyl, 2-[N-methyl-N-(2-methylpropyl)amino]ethyl, 2-[N-(1,1-dimethylethyl)-N-methylamino]ethyl, 2-[N-ethyl-N-propylamino]ethyl, 2-[N-ethyl-N-(1-methylethyl)amino]ethyl, 2-[N-butyl-N-ethylamino]ethyl, 2-[N-ethyl-N-(1-methylpropyl)amino] ethyl, 2-[N-ethyl-N-(2-methylpropyl)amino]ethyl, 2-[N-ethyl-N-(1,1-dimethylethylamino]ethyl, 2-[N-(1-methylethyl)-N-propylamino]ethyl, 2-[N-butyl-N-propylamino]ethyl, 2-[N-(1-methylpropyl)-N-propylamino] ethyl, 2-[N-(2-methylpropyl)-N-propylamino]ethyl, 2-[N-(1,1-dimethylethyl)-N-propylamino]ethyl, 2-[N-butyl-N-(1-methylethyl)amino]ethyl, 2-[N-(1-methylethyl)-N-(1-methylpropyl)amino]ethyl, 2-[N-(1-methylethyl)-N-(2-methylpropyl)amino]ethyl, 2-[N-(1,1-dimethylethyl)-N-(1-methylethyl)amino]ethyl, 2-[N-butyl-N-(1-methylpropyl) amino]ethyl, 2-[N-butyl-N-(2-methylpropyl)amino]ethyl,2-[N-butyl-N-(1,1-dimethylethyl)amino]ethyl, 2-[N-(1-methylpropyl)-N-(2-methylpropyl)amino]ethyl, 2-[N-(1,1-dimethylethyl)-N-(1-methylpropyl)amino]ethyl, 2-[N-(1,1-dimethylethyl)-N-(2-methylpropyl)amino]ethyl, 3-(N,N-dimethylamino)propyl, 3-(N,N-diethylamino)propyl, 4-(N,N-dimethylamino)butyl and 4-(N,N-diethylamino)butyl;

$C_1$-$C_4$-alkoxy-$C_1$-$C_4$-alkyl: $C_1$-$C_4$-alkyl which is substituted by $C_1$-$C_4$-alkoxy as mentioned above, for example methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy) ethyl, 2-(2-methylpropoxy)ethyl, 2-(1,1-dimethylethoxy) ethyl, 2-(methoxy)-propyl, 2-(ethoxy)propyl, 2-(propoxy) propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)-propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy) butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl and 4-(1,1-dimethylethoxy)butyl;

$C_1$-$C_4$-alkylthio-$C_1$-$C_4$-alkyl: $C_1$-$C_4$-alkyl which is substituted by $C_1$-$C_4$-alkylthio as mentioned above, for example methylthiomethyl, ethylthiomethyl, propylthiomethyl, (1-methylethylthio)methyl, butylthiomethyl, (1-methylpropylthio)methyl, (2-methylpropylthio)methyl, (1,1-dimethylethylthio)methyl, 2-methylthioethyl, 2-ethylthioethyl, 2-(propylthio)ethyl, 2-(1-methylethylthio)ethyl, 2-(butylthio)ethyl, 2-(1-methylpropylthio)ethyl, 2-(2-methylpropylthio)ethyl, 2-(1,1-dimethylethylthio)ethyl, 2-(methylthio) propyl, 3-(methylthio)propyl, 2-(ethylthio)propyl, 3-(ethylthio)propyl, 3-(propylthio)propyl, 3-(butylthio)propyl, 4-(methylthio)butyl, 4-(ethylthio)butyl, 4-(propylthio) butyl and 4-(butylthio)butyl;

$C_1$-$C_4$-alkoxycarbonyl-$C_1$-$C_4$-alkyl: $C_1$-$C_4$-alkyl which is substituted by $C_1$-$C_4$-alkoxycarbonyl as mentioned above, for example methoxycarbonylmethyl, ethoxycarbonylmethyl, propoxycarbonylmethyl, (1-methylethoxycarbonyl) methyl, butoxycarbonylmethyl, (1-methylpropoxycarbonyl) methyl, (2-methylpropoxycarbonyl)methyl, (1,1-dimethylethoxycarbonyl)methyl, 2-(methoxycarbonyl)ethyl, 2-(ethoxycarbonyl)ethyl, 2-(propoxycarbonyl)ethyl, 2-(1-methylethoxycarbonyl)ethyl, 2-(butoxycarbonyl)ethyl, 2-(1-methylpropoxycarbonyl)ethyl, 2-(2-methylpropoxycarbonyl)ethyl, 2-(1,1-dimethylethoxycarbonyl)ethyl, 2-(methoxycarbonyl)propyl, 2-(ethoxycarbonyl)propyl, 2-(propoxycarbonyl)propyl, 2-(1-methylethoxycarbonyl) propyl, 2-(butoxycarbonyl)propyl, 2-(1-methylpropoxycarbonyl)propyl, 2-(2-methylpropoxycarbonyl)propyl, 2-(1,1-dimethylethoxycarbonyl)propyl, 3-(methoxycarbonyl) propyl, 3-(ethoxycarbonyl)propyl, 3-(propoxycarbonyl) propyl, 3-(1-methylethoxycarbonyl)propyl, 3-(butoxycarbonyl)propyl, 3-(1-methylpropoxycarbonyl) propyl, 3-(2-methylpropoxycarbonyl)propyl, 3-(1,1-dimethylethoxycarbonyl)propyl, 2-(methoxycarbonyl)butyl, 2-(ethoxycarbonyl)butyl, 2-(propoxycarbonyl)butyl, 2-(1-methylethoxycarbonyl)butyl, 2-(butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl)butyl, 3-(ethoxycarbonyl)butyl, 3-(propoxycarbonyl)butyl, 3-(1-methylethoxycarbonyl)butyl, 3-(butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl)-butyl, 4-(ethoxycarbonyl)butyl, 4-(propoxycarbonyl)butyl, 4-(1-methylethoxycarbonyl)butyl, 4-(butoxycarbonyl)butyl, 4-(1-methylpropoxy)butoxy, 4-(2-methylpropoxy)butoxy und 4-(1,1-dimethylethoxycarbonyl)butyl;

$C_1$-$C_4$-alkoxy-$C_2$-$C_4$-alkoxy: $C_2$-$C_4$-alkoxy which is substituted by $C_1$-$C_4$-alkoxy as mentioned above, for example 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy) butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)-butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy) butoxy, 4-(1-methylpropoxy)butoxy, 4-(2-methylpropoxy) butoxy and 4-(1,1-dimethylethoxy)butoxy;

$C_2$-$C_6$-alkanediyl: for example ethane-1,2-diyl, propane-1,3-diyl, butane-1,4-diyl, pentane-1,5-diyl and hexane-1,6-diyl;

$C_3$-$C_8$-cycloalkyl: for example cyclopropyl, cyclobutyl, cyclopentyl, cyclohexyl, cycloheptyl or cyclooctyl;

All phenyl rings are preferably unsubstituted or have attached to them one to three halogen atoms and/or a nitro group, a cyano radical and/or one or two methyl, trifluoromethyl, methoxy or trifluoromethoxy substituents.

Preference is given to the 3-heterocyclyl-substituted benzoyl derivatives of the formula I where the variables have the following meanings:

$R^1$, $R^2$ are hydrogen, nitro, halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl or $C_1$-$C_6$-haloalkylsulfonyl;

$R^3$ is hydrogen, halogen or $C_1$-$C_6$-alkyl;

$R^4$, $R^5$ are hydrogen, halogen, cyano, nitro, $C_1$-$C_4$-alkyl, $C_1$-$C_4$-alkoxy-$C_1$-$C_4$-alkyl, di($C_1$-$C_4$-alkoxy)-$C_1$-$C_4$-alkyl, di($C_1$-$C_4$-alkyl)-amino-$C_1$-$C_4$-alkyl, [2,2-di($C_1$-$C_4$-alkyl)-1-hydrazino]-$C_1$-$C_4$-alkyl, $C_1$-$C_6$-alkyliminooxy-$C_1$-$C_4$-alkyl, $C_1$-$C_4$-alkoxycarbonyl-$C_1$-$C_4$-alkyl, $C_1$-$C_4$-alkylthio-$C_1$-$C_4$-alkyl, $C_1$-$C_4$-haloalkyl, $C_1$-$C_4$-cyanoalkyl, $C_3$-$C_8$-cycloalkyl, $C_1$-$C_4$-alkoxy, $C_1$-$C_4$-alkoxy-$C_2$-$C_4$-alkoxy, $C_1$-$C_4$-haloalkoxy, $C_1$-$C_4$-alkylthio, $C_1$-$C_4$-haloalkylthio, di($C_1$-$C_4$-alkyl)amino, $COR^6$, phenyl or benzyl, it being possible for the two last-mentioned substituents to be fully or partially halogenated and/or to have attached to them one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy;

or $R^4$ and $R^5$ together form a $C_2$-$C_6$-alkanediyl chain which can be mono-to tetrasubstituted by $C_1$-$C_4$-alkyl and/or which can be interrupted by oxygen or by a nitrogen which is unsubstituted or substituted [lacuna] $C_1$-$C_4$-alkyl;

or $R^4$ and $R^5$ together with the corresponding carbon form a carbonyl or thiocarbonyl group;

$R^6$ is $C_1$-$C_4$-alkyl, $C_1$-$C_4$-haloalkyl, $C_1$-$C_4$-alkoxy, $C_1$-$C_4$-alkoxy-$C_2$-$C_4$-alkoxy, $C_1$-$C_4$-haloalkoxy, $C_3$-$C_6$-alkenyloxy, $C_3$-$C_6$-alkynyloxy or $NR^7R^8$;

$R^7$ is hydrogen or $C_1$-$C_4$-alkyl;

$R^8$ is $C_1$-$C_4$-alkyl;

X is O, S, $NR^9$, CO or $CR^{10}R^{11}$;

Y is O, S, $NR^{12}$, CO or $CR^{13}R^{14}$;

$R^9$, $R^{12}$ are hydrogen or $C_1$-$C_4$-alkyl;

$R^{10}$, $R^{11}$, $R^{13}$, $R^{14}$ are hydrogen, $C_1$-$C_4$-alkyl, $C_1$-$C_4$-haloalkyl, $C_1$-$C_4$-alkoxycarbonyl, $C_1$-$C_4$-haloalkoxycarbonyl or $CONR^7R^8$;

or $R^4$ and $R^9$ or $R^4$ and $R^{10}$ or $R^5$ and $R^{12}$ or $R^5$ and $R^{13}$ together form a $C_2$-$C_6$-alkanediyl chain which can be mono- to tetrasubstituted by $C_1$-$C_4$-alkyl and/or interrupted by oxygen or by a nitrogen which is unsubstituted or substituted by $C_1$-$C_4$-alkyl;

$R^{15}$ is a pyrazole of the formula II which is linked in the 4-position

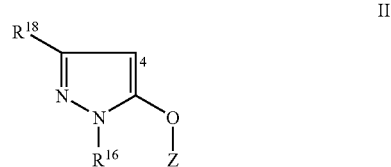

where $R^{16}$ is $C_1$-$C_6$-alkyl;

Z is H or $SO_2R^{17}$;

$R^{17}$ is $C_1$-$C_4$-alkyl, $C_1$-$C_4$-haloalkyl, phenyl or phenyl which is partially or fully halogenated and/or has attached to it one to three of the following groups:

nitro, cyano, $C_1$-$C_4$-alkyl, $C_1$-$C_4$-haloalkyl, $C_1$-$C_4$-alkoxy or $C_1$-$C_4$-haloalkoxy;

$R^{18}$ is hydrogen or $C_1$-$C_6$-alkyl;

where X and Y are not simultaneously oxygen or sulfur;

with the exception of 4-[2-chloro-3-(4,5-dihydroisoxazol-3-yl)-4-methylsulfonylbenzoyl]-1-ethyl-5-hydroxy-1H-pyrazole, 4-[2-chloro-3-(4,5-dihydroisoxazol-3-yl)-4-methylsulfonyl-benzoyl]-1,3-dimethyl-5-hydroxy-1H-pyrazole, 4-[2-chloro-3-(5-cyano-4,5-dihydroisoxazol-3-yl)-4-methyl-sulfonylbenzoyl]-1,3-dimethyl-5-hydroxy-1H-pyrazole, 4-[2-chloro-3-(4,5-dihydrothiazol-2-yl)-4-methylsulfonylbenzoyl]-1,3-dimethyl-5-hydroxy-1H-pyrazole and 4-[2-chloro-3-(thiazoline-4,5-dion-2-yl)-4-methylsulfonyl-benzoyl]-1,3-dimethyl-5-hydroxy-1H-pyrazole;

or the agriculturally useful salts thereof.

With a view to the use of the compounds of the formula I according to the invention as herbicides, the variables preferably have the following meanings, in each case alone or in combination:

$R^1$, $R^2$ are nitro, halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl or $C_1$-$C_6$-haloalkylsulfonyl;

especially preferably nitro, halogen such as, for example, chlorine and bromine, $C_1$-$C_6$-alkyl such as, for example, methyl and ethyl, $C_1$-$C_6$-alkoxy such as, for example, methoxy and ethoxy, $C_1$-$C_6$-haloalkyl such as, for example, difluoromethyl and trifluoromethyl, $C_1$-$C_6$-alkylthio such as, for example, methylthio and ethylthio, $C_1$-$C_6$-alkylsulfinyl such as, for example, methylsulfinyl and ethylsulfinyl, $C_1$-$C_6$-alkylsulfonyl such as, for example, methylsulfonyl, ethylsulfonyl and propylsulfonyl or $C_1$-$C_6$-haloalkylsulfonyl such as, for example, trifluoromethylsulfonyl and pentafluoroethylsulfonyl;

$R^3$ is hydrogen;

$R^4$, $R^5$ are hydrogen, halogen, cyano, nitro, $C_1$-$C_4$-alkyl, $C_1$-$C_4$-alkoxy-$C_1$-$C_4$-alkyl, di($C_1$-$C_4$-alkoxy)-$C_1$-$C_4$-alkyl, di($C_1$-$C_4$-alkyl)amino-$C_1$-$C_4$-alkyl, [2,2-di($C_1$-$C_4$-alkyl)hydrazino-1]-$C_1$-$C_4$-alkyl, $C_1$-$C_6$-alkyliminooxy-$C_1$-$C_4$-alkyl, $C_1$-$C_4$-alkoxycarbonyl-$C_1$-$C_4$-alkyl, $C_1$-$C_4$-alkylthio-$C_1$-$C_4$-alkyl, $C_1$-$C_4$-haloalkyl, $C_1$-$C_4$-cyanoalkyl, $C_3$-$C_8$-cycloalkyl, $C_1$-$C_4$-alkoxy, $C_1$-$C_4$-alkoxy-$C_2$-$C_4$-alkoxy, $C_1$-$C_4$-haloalkoxy, $C_1$-$C_4$-alkylthio, $C_1$-$C_4$-haloalkylthio, di($C_1$-$C_4$-alkyl)amino, $COR^6$, phenyl or benzyl, it being possible for the two last-mentioned substituents to be partially or fully halogenated and/or to have attached to them one to three of the following groups:

nitro, cyano, $C_1$-$C_4$-alkyl, $C_1$-$C_4$-haloalkyl, $C_1$-$C_4$-alkoxy or $C_1$-$C_4$-haloalkoxy;

or $R^4$ and $R^5$ together form a $C_2$-$C_6$-alkanediyl chain which can be mono-to tetrasubstituted by $C_1$-$C_4$-alkyl and/or which can be interrupted by oxygen or by a nitrogen which is unsubstituted or substituted by $C_1$-$C_4$-alkyl;

$R^4$ is especially preferably hydrogen, $C_1$-$C_4$-alkyl, $C_1$-$C_4$-haloalkyl, $C_1$-$C_4$-alkoxycarbonyl or $CONR^7R^8$;

$R^5$ is especially preferably hydrogen or $C_1$-$C_4$-alkyl; or $R^4$ and $R^5$ especially preferably form a $C_2$-$C_6$-alkanediyl chain which can be mono- to tetrasubstituted by $C_1$-$C_4$-alkyl and/or which can be interrupted by oxygen or by a nitrogen which is unsubstituted or substituted by $C_1$-$C_4$-alkyl;

$R^6$ is $C_1$-$C_4$-alkyl, $C_1$-$C_4$-alkoxy or $NR^7R^8$;

$R^7$ is hydrogen or $C_1$-$C_4$-alkyl;

$R^8$ is $C_1$-$C_4$-alkyl;

X is O, S, $NR^9$, CO or $CR^{10}R^{11}$;

Y is O, S, $NR^{12}$ or $CR^{13}R^{14}$;

$R^9$, $R^{12}$ are hydrogen or $C_1$-$C_4$-alkyl;

$R^{10}$, $R^{11}$, $R^{13}$, $R^{14}$ are hydrogen, $C_1$-$C_4$-alkyl, $C_1$-$C_4$-haloalkyl, $C_1$-$C_4$-alkoxycarbonyl, $C_1$-$C_4$-haloalkoxycarbonyl or $CONR^7R^8$;

or $R^4$ and $R^9$ or $R^4$ and $R^{10}$ or $R^5$ and $R^{12}$ or $R^5$ and $R^{13}$ together form a $C_2$-$C_6$-alkanediyl chain which can be mono-to tetrasubstituted by $C_1$-$C_4$-alkyl and/or which can be interrupted by oxygen or by a nitrogen which is unsubstituted or substituted by $C_1$-$C_4$-alkyl;

$R^{16}$ is $C_1$-$C_6$-alkyl;

especially preferably methyl, ethyl, propyl, 2-methylpropyl or butyl;

Z is H or $SO_2R^{17}$;

$R^{17}$ is $C_1$-$C_4$-alkyl, phenyl or phenyl which is partially or fully halogenated and/or has attached to it one to three of the following groups:

nitro, cyano, $C_1$-$C_4$-alkyl, $C_1$-$C_4$-haloalkyl, $C_1$-$C_4$-alkoxy or $C_1$-$C_4$-haloalkoxy;

$R^{18}$ is hydrogen or $C_1$-$C_6$-alkyl;

especially preferably hydrogen or methyl.

The following embodiments of the 3-heterocyclyl-substituted benzoyl derivatives of the formula I must be emphasized:

1. In a preferred embodiment of the 3-heterocyclyl-substituted benzoyl derivatives of the formula I, Z is $SO_2R^{17}$.

Especially preferred are the 3-heterocyclyl-substituted benzoyl derivatives of the formula I, where $R^{18}$ is hydrogen.

Also especially preferred are 3-heterocyclyl-substituted benzoyl derivatives of the formula I, where $R^{18}$ is methyl.

Particularly preferred are 3-heterocylyl-substituted benzoyl derivatives of the formula I, where $R^{17}$ is $C_1$-$C_4$-alkyl.

2. In a further preferred embodiment of the 3-heterocyclyl-substituted benzoyl derivatives of the formula I, Z is hydrogen.

Especially preferred are 3-heterocyclyl-substituted benzoyl derivatives of the formula I where X is oxygen and Y is $CR^{13}R^{14}$.

Particularly preferred are 3-heterocyclyl-substituted benzoyl derivatives of the formula I where $R^4$ is halogen, nitro, $C_1$-$C_4$-alkyl, $C_1$-$C_4$-alkoxy-$C_1$-$C_4$-alkyl, $C_1$-$C_4$-alkoxycarbonyl-$C_1$-$C_4$-alkyl, $C_1$-$C_4$-alkylthio-$C_1$-$C_4$-alkyl, $C_1$-$C_4$-haloalkyl, $C_1$-$C_4$-cyanoalkyl, $C_3$-$C_8$-cycloalkyl, $C_1$-$C_4$-alkoxy, $C_1$-$C_4$-Alkoxy-$C_2$-$C_4$-alkoxy, $C_1$-$C_4$-haloalkoxy, $C_1$-$C_4$-alkylthio, $C_1$-$C_4$-haloalkylthio, di($C_1$-$C_4$-alkyl)amino, $COR^6$, phenyl or benzyl, it being possible for the two last-mentioned substituents to be partially or fully halogenated and/or to have attached to them one to three of the following groups:

nitro, cyano, $C_1$-$C_4$-alkyl, $C_1$-$C_4$-haloalkyl, $C_1$-$C_4$-alkoxy or $C_1$-$C_4$-haloalkoxy;

$R^5$ is hydrogen or $C_1$-$C_4$-alkyl;

or $R^4$ and $R^5$ together form a $C_2$-$C_6$-alkanediyl chain which can be mono- to tetrasubstituted by $C_1$-$C_4$-alkyl and/or which can be interrupted by oxygen or by a nitrogen which is unsubstituted or substituted by $C_1$-$C_4$-alkyl;

or $R^5$ and $R^{13}$ together form a $C_2$-$C_6$-alkanediyl chain which can be mono- to tetrasubstituted by $C_1$-$C_4$-alkyl and/or which can be interrupted by oxygen or by a nitrogen which is unsubstituted or substituted by $C_1$-$C_4$-alkyl.

Extraordinarily preferred are 3-heterocyclyl-substituted benzoyl derivatives of the formula I where $R^4$ is $C_1$-$C_4$-alkyl, $C_1$-$C_4$-haloalkyl, $C_1$-$C_4$-alkoxycarbonyl or $CONR^7R^8$;

$R^5$ is hydrogen or $C_1$-$C_4$-alkyl;

or $R^4$ and $R^5$ together form a $C_2$-$C_6$-alkanediyl chain which can be mono- to tetrasubstituted by $C_1$-$C_4$-alkyl and/or which can be interrupted by oxygen or by a nitrogen which is unsubstituted or substituted by $C_1$-$C_4$-alkyl;

or $R^5$ and $R^{13}$ together form a $C_2$-$C_6$-alkanediyl chain which can be mono- to tetrasubstituted by $C_1$-$C_4$-alkyl and/or which can be interrupted by oxygen or by a nitrogen which is unsubstituted or substituted by $C_1$-$C_4$-alkyl.

Especially extraordinarily preferred are 3-heterocyclyl-substituted benzoyl derivatives of the formula I where $R^{18}$ is hydrogen.

Also particularly preferred are 3-heterocyclyl-substituted benzoyl derivatives of the formula I where $R^4$ and $R^5$ are hydrogen.

Extraordinarily preferred are 3-heterocyclyl-substituted benzoyl derivatives of the formula I where $R^{18}$ is hydrogen.

Especially extraordinarily preferred are 3-heterocyclyl-substituted benzoyl derivatives of the formula I where $R^1$ is nitro, $C_1$-$C_6$-alkyl such as, for example, methyl and ethyl, $C_1$-$C_6$-alkoxy such as, for example, methoxy and ethoxy, $C_1$-$C_6$-haloalkyl such as, for example, difluoromethyl and trifluoromethyl, $C_1$-$C_6$-alkylsulfonyl such as, for example, methylsulfonyl, ethylsulfonyl and propylsulfonyl, or $C_1$-$C_6$-haloalkylsulfonyl such as, for example, trifluoromethylsulfonyl and pentafluoroethylsulfonyl;

Also especially extraordinarily preferred are 3-heterocyclyl-substituted benzoyl derivatives of the formula I where $R^2$ is nitro, halogen such as, for example, chlorine and bromine, $C_1$-$C_6$-alkyl such as, for example, methyl and ethyl, $C_1$-$C_6$-haloalkyl such as, for example, difluoromethyl and trifluoromethyl, $C_1$-$C_6$-alkylthio such as, for example, methylthio and ethylthio, $C_1$-$C_6$-alkylsulfinyl such as, for example, methylsulfinyl and ethylsulfinyl, $C_1$-$C_6$-alkylsulfonyl such as, for example, methylsulfonyl, ethylsulfonyl and propylsulfonyl, or $C_1$-$C_6$-haloalkylsulfonyl such as, for example, trifluomethylsulfonyl and pentafluoroethylsulfonyl.

Also especially extraordinarily preferred is 4-[2-chloro-3-(4,5-dihydroisoxazol-3-yl)-4-methylsulfonylbenzoyl]-1-methyl-5-hydroxy-1H-pyrazole.

Also especially extraordinarily preferred are the agriculturally useful salts of 4-[2-chloro-3-(4,5-dihydroisoxazol-3-yl)-4-methylsulfonyl-benzoyl]-1-methyl-5-hydroxy-1H-pyrazole, in particular the alkali metal salts, such as, for example, lithium, sodium and potassium, and the ammonium salts, it being possible in this case, if desired, for one to four hydrogen atoms to be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium.

Also extraordinarily preferred are 3-heterocyclyl-substituted benzoyl derivatives of the formula I where $R^{18}$ is methyl.

Especially extraordinarily preferred are 3-heterocyclyl-substituted benzoyl derivatives of the formula I where $R^1$ is nitro, $C_1$-$C_6$-alkyl such as, for example, methyl and ethyl, $C_1$-$C_6$-alkoxy such as, for example, methoxy and ethoxy, $C_1$-$C_6$-haloalkyl such as, for example, difluoromethyl and trifluoromethyl, $C_1$-$C_6$-alkylsulfonyl such as, for example, methylsulfonyl, ethylsulfonyl and propylsulfonyl, or $C_1$-$C_6$-haloalkylsulfonyl, for example trifluoromethylsulfonyl and pentafluoroethylsulfonyl.

Also especially extraordinarily preferred are 3-heterocyclyl-substituted benzoyl derivatives of the formula I where $R^2$ is nitro, halogen such as, for example, chlorine and bromine, $C_1$-$C_6$-alkyl such as, for example, methyl and ethyl, $C_1$-$C_6$-haloalkyl such as, for example, difluoromethyl and trifluoromethyl, $C_1$-$C_6$-alkylthio such as, for example, methylthio and ethylthio, $C_1$-$C_6$-alkylsulfinyl such as, for example, methylsulfinyl and ethylsulfinyl, $C_1$-$C_6$-alkylsulfonyl such as, for example, methylsulfonyl, ethylsulfonyl and propylsulfonyl, or $C_1$-$C_6$-haloalkylsulfonyl such as, for example, trifluoromethylsulfonyl and pentafluoroethylsulfonyl.

Also especially preferred are 3-heterocyclyl-substituted benzoyl derivatives of the formula I where X is S, $NR^9$, CO or $CR^{10}OR^{11}$;

or

Y is O, S, $NR^{12}$ or CO.

Particularly preferred are 3-heterocyclyl-substituted benzoyl derivatives of the formula I where $R^{18}$ is hydrogen.

Also particularly preferred are 3-heterocyclyl-substituted benzoyl derivatives of the formula I where $R^{18}$ is $C_1$-$C_6$-alkyl.

Extraordinarily preferred are 3-heterocyclyl-substituted benzoyl derivatives of the formula I where $R^4$ is halogen, cyano, nitro, $C_1$-$C_4$-alkyl, $C_1$-$C_4$-alkoxy-$C_1$-$C_4$-alkyl, $C_1$-$C_4$-alkoxycarbonyl-$C_1$-$C_4$-alkyl, $C_1$-$C_4$-alkylthio-$C_1$-$C_4$-alkyl, $C_1$-$C_4$-haloalkyl, $C_1$-$C_4$-cyanoalkyl, $C_3$-$C_8$-cycloalkyl, $C_1$-$C_6$-alkoxy, $C_1$-$C_4$-alkoxy-$C_1$-$C_4$-alkoxy, $C_1$-$C_4$-haloalkoxy, $C_1$-$C_4$-alkylthio, $C_1$-$C_4$-haloalkylthio, di($C_1$-$C_4$-alkyl)amino, $COR^6$, phenyl or benzyl, it being possible for the two last-mentioned substituents to be partially or fully halogenated and/or to have attached to them one to three of the following groups:

nitro, cyano, $C_1$-$C_4$-alkyl, $C_1$-$C_4$-haloalkyl, $C_1$-$C_4$-alkoxy or $C_1$-$C_4$-haloalkoxy;

$R^5$ is hydrogen or $C_1$-$C_4$-alkyl;

or $R^4$ and $R^5$ together form a $C_2$-$C_6$-alkanediyl chain which can be mono- to tetrasubstituted by $C_1$-$C_4$-alkyl and/or which can be interrupted by oxygen or by a nitrogen which is unsubstituted or substituted by $C_1$-$C_4$-alkyl;

or $R^4$ and $R^9$ or $R^4$ and $R^{10}$ or $R^5$ and $R^{12}$ or $R^5$ and $R^{13}$ together form a $C_2$-$C_6$-alkanediyl chain which can be mono- to tetrasubstituted by $C_1$-$C_4$-alkyl and/or which can be interrupted by oxygen or by a nitrogen which is unsubstituted or substituted by $C_1$-$C_4$-alkyl.

Also particularly preferred are 3-heterocyclyl-substituted benzoyl derivatives of the formula I where X is S, $NR^9$ or CO or y is O, $NR^{12}$ or CO.

Extraordinarily preferred are 3-heterocyclyl-substituted benzoyl derivatives of the formula I where $R^4$ is halogen, cyano, nitro, $C_1$-$C_4$-alkyl, $C_1$-$C_4$-alkoxy-$C_1$-$C_4$-alkyl, $C_1$-$C_4$-alkoxycarbonyl-$C_1$-$C_4$-alkyl, $C_1$-$C_4$-alkylthio-$C_1$-$C_4$-alkyl, $C_1$-$C_4$-haloalkyl, $C_1$-$C_4$-cyanoalkyl, $C_3$-$C_8$-cycloalkyl, $C_1$-$C_6$-alkoxy, $C_1$-$C_4$-alkoxy-$C_1$-$C_4$-alkoxy, $C_1$-$C_4$-haloalkoxy, $C_1$-$C_4$-alkylthio, $C_1$-$C_4$-haloalkylthio, di($C_1$-$C_4$-alkyl)amino, $COR^6$, phenyl or benzyl, it being possible for the two last-mentioned substituents to be partially or fully halogenated and/or to have attached to them one to three of the following groups:

nitro, cyano, $C_1$-$C_4$-Alkyl, $C_1$-$C_4$-haloalkyl, $C_1$-$C_4$-alkoxy or $C_1$-$C_4$-haloalkoxy;

$R^5$ is hydrogen or $C_1$-$C_4$-alkyl;

or $R^4$ and $R^5$ together form a $C_2$-$C_6$-alkanediyl chain which can be mono- to tetrasubstituted by $C_1$-$C_4$-alkyl and/or which can be interrupted by oxygen or by a nitrogen which is unsubstituted or substituted by $C_1$-$C_4$-alkyl;

or $R^4$ and $R^9$ or $R^4$ and $R^{10}$ or $R^5$ and $R^{12}$ or $R^5$ and $R^{13}$ together form a $C_2$-$C_6$-alkanediyl chain which can be mono- to tetrasubstituted by $C_1$-$C_4$-alkyl and/or which can be interrupted by oxygen or by a nitrogen which is unsubstituted or substituted by $C_1$-$C_4$-alkyl.

Particularly extraordinarily preferred are the compounds Ia1 (≙ I where R¹=Cl, R²=SO₂CH₃, R³=H, R¹⁶, R¹⁸=CH₃, Z=H), in particular the compounds of Table 1.

TABLE 1

Ia1

| No. | X | R⁴ | R⁵ | Y |
|---|---|---|---|---|
| Ia1.1 | CH₂ | H | CH₃ | O |
| Ia1.2 | CH₂ | H | H | O |
| Ia1.3 | C(CH₃)₂ | H | H | O |
| Ia1.4 | CH₂ | H | C₂H₅ | O |
| Ia1.5 | CH₂ | CH₃ | CH₃ | O |
| Ia1.6 | CH(CH₃) | H | CH₃ | O |
| Ia1.7 | CH(C₂H₅) | H | CH₃ | O |
| Ia1.8 | CH[CH(CH₃)₂] | H | H | O |
| Ia1.9 | CH₂ | H | CH(CH₃)₂ | O |
| Ia1.10 | CH(C₂H₅) | H | C₂H₅ | O |
| Ia1.11 | —CH—(CH₂)₄— | | H | O |
| Ia1.12 | C=O | CH₃ | CH₃ | O |
| Ia1.13 | C=O | H | C₂H₅ | O |
| Ia1.14 | C=O | C₂H₅ | C₂H₅ | O |
| Ia1.15 | C=O | H | H | O |
| Ia1.16 | C=O | H | CH₃ | O |
| Ia1.17 | CH₂ | H | CH₃ | S |
| Ia1.18 | C(CH₃)₂ | H | H | S |
| Ia1.19 | CH₂ | H | C₂H₅ | S |
| Ia1.20 | CH₂ | CH₃ | CH₃ | S |
| Ia1.21 | CH(CH₃) | H | CH₃ | S |
| Ia1.22 | CH(C₂H₅) | H | CH₃ | S |
| Ia1.23 | CH(C₂H₅) | H | C₂H₅ | S |
| Ia1.24 | —CH—(CH₂)₄— | | H | S |
| Ia1.25 | CH[CH(CH₃)₂] | H | H | S |
| Ia1.26 | CH₂ | H | CH(CH₃)₂ | S |
| Ia1.27 | CH₂ | H | CH₃ | NH |
| Ia1.28 | CH₂ | H | H | NH |
| Ia1.29 | C(CH₃)₂ | H | H | NH |
| Ia1.30 | CH₂ | H | C₂H₅ | NH |
| Ia1.31 | CH₂ | CH₃ | CH₃ | NH |
| Ia1.32 | CH(CH₃) | H | CH₃ | NH |
| Ia1.33 | CH(C₂H₅) | H | CH₃ | NH |
| Ia1.34 | CH(C₂H₅) | H | C₂H₅ | NH |
| Ia1.35 | —CH—(CH₂)₄— | | H | NH |
| Ia1.36 | CH[CH(CH₃)₂] | H | H | NH |
| Ia1.37 | CH₂ | H | CH(CH₃)₂ | NH |
| Ia1.38 | CH₂ | H | CH₃ | NCH₃ |
| Ia1.39 | CH₂ | H | H | NCH₃ |
| Ia1.40 | C(CH₃)₂ | H | H | NCH₃ |
| Ia1.41 | CH₂ | H | C₂H₅ | NCH₃ |
| Ia1.42 | CH₂ | CH₃ | CH₃ | NCH₃ |
| Ia1.43 | CH(CH₃) | H | CH₃ | NCH₃ |
| Ia1.44 | CH(C₂H₅) | H | CH₃ | NCH₃ |
| Ia1.45 | CH[CH(CH₃)₂] | H | H | NCH₃ |
| Ia1.46 | CH₂ | H | CH(CH₃)₂ | NCH₃ |
| Ia1.47 | CH(C₂H₅) | H | C₂H₅ | NCH₃ |
| Ia1.48 | —CH—(CH₂)₄— | | H | NCH₃ |
| Ia1.49 | CH₂ | H | CH₃ | NC₂H₅ |
| Ia1.50 | CH₂ | H | H | NC₂H₅ |
| Ia1.51 | C(CH₃)₂ | H | H | NC₂H₅ |
| Ia1.52 | CH₂ | H | C₂H₅ | NC₂H₅ |
| Ia1.53 | CH₂ | CH₃ | CH₃ | NC₂H₅ |
| Ia1.54 | CH(CH₃) | H | CH₃ | NC₂H₅ |
| Ia1.55 | CH(C₂H₅) | H | CH₃ | NC₂H₅ |
| Ia1.56 | CH[CH(CH₃)₂] | H | H | NC₂H₅ |
| Ia1.57 | CH₂ | H | CH(CH₃)₂ | NC₂H₅ |
| Ia1.58 | CH(C₂H₅) | H | C₂H₅ | NC₂H₅ |
| Ia1.59 | —CH—(CH₂)₄— | | H | NC₂H₅ |
| Ia1.60 | CH₂ | =O | | S |
| Ia1.61 | CH(CH₃) | =O | | S |

TABLE 1-continued

Ia1

| No. | X | R⁴ | R⁵ | Y |
|---|---|---|---|---|
| Ia1.62 | CH(C₂H₅) | =O | | S |
| Ia1.63 | CH[CH(CH₃)₂] | =O | | S |
| Ia1.64 | C(CH₃)₂ | =O | | S |
| Ia1.65 | CCH₃(C₂H₅) | =O | | S |
| Ia1.66 | CCH₃[CH(CH₃)₂] | =O | | S |
| Ia1.67 | CH₂ | =O | | NH |
| Ia1.68 | CH(CH₃) | =O | | NH |
| Ia1.69 | CH(C₂H₅) | =O | | NH |
| Ia1.70 | CH[CH(CH₃)₂] | =O | | NH |
| Ia1.71 | C(CH₃)₂ | =O | | NH |
| Ia1.72 | CCH₃(C₂H₅) | =O | | NH |
| Ia1.73 | CCH₃[CH(CH₃)₂] | =O | | NH |
| Ia1.74 | CH₂ | =O | | NCH₃ |
| Ia1.75 | CH(CH₃) | =O | | NCH₃ |
| Ia1.76 | CH(C₂H₅) | =O | | NCH₃ |
| Ia1.77 | CH[CH(CH₃)₂] | =O | | NCH₃ |
| Ia1.78 | C(CH₃)₂ | =O | | NCH₃ |
| Ia1.79 | CCH₃(C₂H₅) | =O | | NCH₃ |
| Ia1.80 | CCH₃[CH(CH₃)₂] | =O | | NCH₃ |
| Ia1.81 | O | COOCH₃ | H | CH₂ |
| Ia1.82 | O | COOC₂H₅ | H | CH₂ |
| Ia1.83 | O | CONHCH₃ | H | CH₂ |
| Ia1.84 | O | CON(CH₃)₂ | H | CH₂ |
| Ia1.85 | O | CONHC₂H₅ | H | CH₂ |
| Ia1.86 | O | CON(C₂H₅)₂ | H | CH₂ |
| Ia1.87 | O | CH₃ | H | CH₂ |
| Ia1.88 | O | C₂H₅ | H | CH₂ |
| Ia1.89 | O | CH(CH₃)₂ | H | CH₂ |
| Ia1.90 | O | COC₂H₅ | H | CH₂ |
| Ia1.91 | O | CH₂CN | H | CH₂ |
| Ia1.92 | O | CH₂N(CH₃)₂ | H | CH₂ |
| Ia1.93 | O | CH₂CN=C(CH₃)₂ | H | CH₂ |
| Ia1.94 | O | OH(OC₂H₅)₂ | H | CH₂ |
| Ia1.95 | O | OH(OCH₃)₂ | H | CH₂ |
| Ia1.96 | O | CH₃ | CH₃ | CH₂ |
| Ia1.97 | O | CH₃ | C₂H₅ | CH₂ |
| Ia1.98 | O | C₂H₅ | C₂H₅ | CH₂ |
| Ia1.99 | O | —(CH₂)₄— | | CH₂ |
| Ia1.100 | O | —(CH₂)₂—O—(CH₂)₂— | | CH₂ |
| Ia1.101 | O | H | | —(CH₂)₃—OH— |
| Ia1.102 | O | H | | —(CH₂)₄—OH— |
| Ia1.103 | O | CH₃ | H | CHCH₃ |
| Ia1.104 | S | =O | | O |
| Ia1.105 | CH₂ | =S | | S |
| Ia1.106 | CH(CH₃) | =S | | S |
| Ia1.107 | CH(C₂H₅) | =S | | S |
| Ia1.108 | C(CH₃)₂ | =S | | S |
| Ia1.109 | O | =O | | NH |
| Ia1.110 | O | =O | | NCH₃ |
| Ia1.111 | O | CH₃ | H | NH |
| Ia1.112 | O | C₂H₅ | H | NH |
| Ia1.113 | O | CH₃ | CH₃ | NH |
| Ia1.114 | O | C₂H₅ | C₂H₅ | NH |
| Ia1.115 | O | CH₃ | H | NCH₃ |
| Ia1.116 | O | C₂H₅ | H | NCH₃ |
| Ia1.117 | O | CH₃ | CH₃ | NCH₃ |
| Ia1.118 | O | C₂H₅ | C₂H₅ | NCH₃ |
| Ia1.119 | NH | =O | | NH |
| Ia1.120 | NH | =O | | NCH₃ |
| Ia1.121 | NCH₃ | =O | | NH |
| Ia1.122 | NCH₃ | =O | | NCH₃ |
| Ia1.123 | NC₂H₅ | =O | | NH |
| Ia1.124 | NC₂H₅ | =O | | NC₂H₅ |

In addition, the following benzoyl derivatives of the formula I are particularly extraordinarily preferred:

The compounds Ia2.1-Ia2.124, which differ from the corresponding compounds Ia1.1-Ia1.124 by the fact that $R^{16}$ is ethyl and $R^{18}$ is hydrogen.

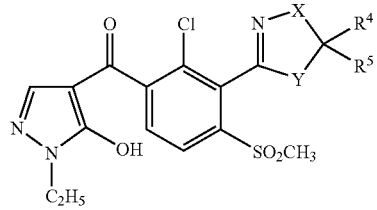

Ia2

Also particularly extraordinarily preferred are the compounds Ib1 (≙I where $R^1$, $R^2$=Cl, $R^3$=H, $R^{16}$, $R^{18}$=CH$_3$, Z=H) in particular the compounds of Table 2

TABLE 2

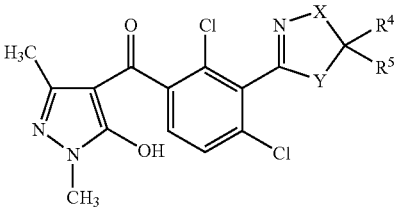

Ib1

| No. | X | R⁴ | R⁵ | Y |
|---|---|---|---|---|
| Ib1.1 | CH₂ | H | CH₃ | O |
| Ib1.2 | CH₂ | H | H | O |
| Ib1.3 | C(CH₃)₂ | H | H | O |
| Ib1.4 | CH₂ | H | C₂H₅ | O |
| Ib1.5 | CH₂ | CH₃ | CH₃ | O |
| Ib1.6 | CH(CH₃) | H | CH₃ | O |
| Ib1.7 | CH(C₂H₅) | H | CH₃ | O |
| Ib1.8 | CH[CH(CH₃)₂] | H | H | O |
| Ib1.9 | CH₂ | H | CH(CH₃)₂ | O |
| Ib1.10 | CH(C₂H₅) | H | C₂H₅ | O |
| Ib1.11 | —CH—(CH₂)₄— | | H | O |
| Ib1.12 | C=O | CH₃ | CH₃ | O |
| Ib1.13 | C=O | H | C₂H₅ | O |
| Ib1.14 | C=O | C₂H₅ | C₂H₅ | O |
| Ib1.15 | C=O | H | H | O |
| Ib1.16 | C=O | H | CH₃ | O |
| Ib1.17 | CH₂ | H | CH₃ | S |
| Ib1.18 | CH₂ | H | H | S |
| Ib1.19 | C(CH₃)₂ | H | H | S |
| Ib1.20 | CH₂ | H | C₂H₅ | S |
| Ib1.21 | CH₂ | CH₃ | CH₃ | S |
| Ib1.22 | CH(CH₃) | H | CH₃ | S |
| Ib1.23 | CH(C₂H₅) | H | CH₃ | S |
| Ib1.24 | CH(C₂H₅) | H | C₂H₅ | S |
| Ib1.25 | —CH—(CH₂)₄— | | H | S |
| Ib1.26 | CH[CH(CH₃)₂] | H | H | S |
| Ib1.27 | CH₂ | H | CH(CH₃)₂ | S |
| Ib1.28 | CH₂ | H | CH₃ | NH |
| Ib1.29 | CH₂ | H | H | NH |
| Ib1.30 | C(CH₃)₂ | H | H | NH |
| Ib1.31 | CH₂ | H | C₂H₅ | NH |
| Ib1.32 | CH₂ | CH₃ | CH₃ | NH |
| Ib1.33 | CH(CH₃) | H | CH₃ | NH |
| Ib1.34 | CH(C₂H₅) | H | CH₃ | NH |
| Ib1.35 | CH(C₂H₅) | H | C₂H₅ | NH |
| Ib1.36 | —CH—(CH₂)₄— | | H | NH |
| Ib1.37 | CH[CH(CH₃)₂] | H | H | NH |
| Ib1.38 | CH₂ | H | CH(CH₃)₂ | NH |
| Ib1.39 | CH₂ | H | CH₃ | NCH₃ |
| Ib1.40 | CH₂ | H | H | NCH₃ |
| Ib1.41 | C(CH₃)₂ | H | H | NCH₃ |
| Ib1.42 | CH₂ | H | C₂H₅ | NCH₃ |
| Ib1.43 | CH₂ | CH₃ | CH₃ | NCH₃ |
| Ib1.44 | CH(CH₃) | H | CH₃ | NCH₃ |
| Ib1.45 | CH(C₂H₅) | H | CH₃ | NCH₃ |
| Ib1.46 | CH[CH(CH₃)₂] | H | H | NCH₃ |
| Ib1.47 | CH₂ | H | CH(CH₃)₂ | NCH₃ |
| Ib1.48 | CH(C₂H₅) | H | C₂H₅ | NCH₃ |
| Ib1.49 | —CH—(CH₂)₄— | | H | NCH₃ |
| Ib1.50 | CH₂ | H | CH₃ | NC₂H₅ |
| Ib1.51 | CH₂ | H | H | NC₂H₅ |
| Ib1.52 | C(CH₃)₂ | H | H | NC₂H₅ |
| Ib1.53 | CH₂ | H | C₂H₅ | NC₂H₅ |
| Ib1.54 | CH₂ | CH₃ | CH₃ | NC₂H₅ |
| Ib1.55 | CH(CH₃) | H | CH₃ | NC₂H₅ |
| Ib1.56 | CH(C₂H₅) | H | CH₃ | NC₂H₅ |
| Ib1.57 | CH[CH(CH₃)₂] | H | H | NC₂H₅ |
| Ib1.58 | CH₂ | H | CH(CH₃)₂ | NC₂H₅ |
| Ib1.59 | CH(C₂H₅) | H | C₂H₅ | NC₂H₅ |
| Ib1.60 | —CH—(CH₂)₄— | | H | NC₂H₅ |
| Ib1.61 | CH₂ | =O | | S |
| Ib1.62 | CH(CH₃) | =O | | S |
| Ib1.63 | CH(C₂H₅) | =O | | S |
| Ib1.64 | CH[CH(CH₃)₂] | =O | | S |
| Ib1.65 | C(CH₃)₂ | =O | | S |
| Ib1.66 | CCH₃(C₂H₅) | =O | | S |
| Ib1.67 | CCH₃[CH(CH₃)₂] | =O | | S |
| Ib1.68 | CH₂ | =O | | NH |
| Ib1.69 | CH(CH₃) | =O | | NH |
| Ib1.70 | CH(C₂H₅) | =O | | NH |
| Ib1.71 | CH[CH(CH₃)₂] | =O | | NH |
| Ib1.72 | C(CH₃)₂ | =O | | NH |
| Ib1.73 | CCH₃(C₂H₅) | =O | | NH |
| Ib1.74 | CCH₃[CH(CH₃)₂] | =O | | NH |
| Ib1.75 | CH₂ | =O | | NCH₃ |
| Ib1.76 | CH(CH₃) | =O | | NCH₃ |
| Ib1.77 | CH(C₂H₅) | =O | | NCH₃ |
| Ib1.78 | CH[CH(CH₃)₂] | =O | | NCH₃ |
| Ib1.79 | C(CH₃)₂ | =O | | NCH₃ |
| Ib1.80 | CCH₃(C₂H₅) | =O | | NCH₃ |
| Ib1.81 | CCH₃[CH(CH₃)₂] | =O | | NCH₃ |
| Ib1.82 | O | COOCH₃ | H | CH₂ |
| Ib1.83 | O | COOC₂H₅ | H | CH₂ |
| Ib1.84 | O | CONHCH₃ | H | CH₂ |
| Ib1.85 | O | CON(CH₃)₂ | H | CH₂ |
| Ib1.86 | O | CONHC₂H₅ | H | CH₂ |
| Ib1.87 | O | CON(C₂H₅)₂ | H | CH₂ |
| Ib1.88 | O | CH₃ | H | CH₂ |
| Ib1.89 | O | C₂H₅ | H | CH₂ |
| Ib1.90 | O | CH(CH₃)₂ | H | CH₂ |
| Ib1.91 | O | COC₂H₅ | H | CH₂ |
| Ib1.92 | O | CH₂CN | H | CH₂ |
| Ib1.93 | O | CH₂N(CH₃)₂ | H | CH₂ |
| Ib1.94 | O | CH₂CN=C(CH₃)₂ | H | CH₂ |
| Ib1.95 | O | OH(OC₂H₅)₂ | H | CH₂ |
| Ib1.96 | O | OH(OCH₃)₂ | H | CH₂ |
| Ib1.97 | O | CH₃ | CH₃ | CH₂ |
| Ib1.98 | O | CH₃ | C₂H₅ | CH₂ |
| Ib1.99 | O | C₂H₅ | C₂H₅ | CH₂ |
| Ib1.100 | O | —(CH₂)₄— | | CH₂ |
| Ib1.101 | O | —(CH₂)₂—O—(CH₂)₂— | | CH₂ |
| Ib1.102 | O | H | —(CH₂)₃—OH— | |
| Ib1.103 | O | H | —(CH₂)₄—OH— | |
| Ib1.104 | O | CH₃ | H | CHCH₃ |

TABLE 2-continued

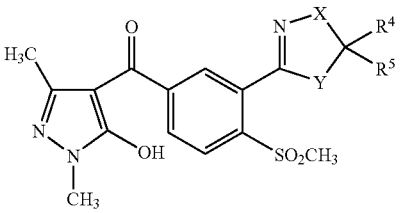

Ib1

| No. | X | R⁴ | R⁵ | Y |
|---|---|---|---|---|
| Ib1.105 | O | H | H | CH₂ |
| Ib1.106 | S | =O | | O |
| Ib1.107 | CH₂ | =S | | S |
| Ib1.108 | CH(CH₃) | =S | | S |
| Ib1.109 | CH(C₂H₅) | =S | | S |
| Ib1.110 | C(CH₃)₂ | =S | | S |
| Ib1.111 | O | =O | | NH |
| Ib1.112 | O | =O | | NCH₃ |
| Ib1.113 | O | CH₃ | H | NH |
| Ib1.114 | O | C₂H₅ | H | NH |
| Ib1.115 | O | CH₃ | CH₃ | NH |
| Ib1.116 | O | C₂H₅ | C₂H₅ | NH |
| Ib1.117 | O | CH₃ | H | NCH₃ |
| Ib1.118 | O | C₂H₅ | H | NCH₃ |
| Ib1.119 | O | CH₃ | CH₃ | NCH₃ |
| Ib1.120 | O | C₂H₅ | C₂H₅ | NCH₃ |
| Ib1.121 | NH | =O | | NH |
| Ib1.122 | NH | =O | | NCH₃ |
| Ib1.123 | NCH₃ | =O | | NH |
| Ib1.124 | NCH₃ | =O | | NCH₃ |
| Ib1.125 | NC₂H₅ | =O | | NH |
| Ib1.126 | NC₂H₅ | =O | | NC₂H₅ |

In addition, the following 3-heterocyclyl-substituted benzoyl derivatives of the formula I are particularly extraordinarily preferred:

The compounds Ib2.1-Ib2.126, which differ from the corresponding compounds Ib1.1-Ib1.126 by the fact that R² is nitro.

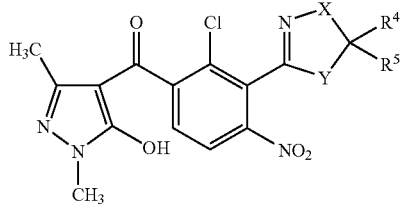

Ib2

The compounds Ib3.1-Ib3.126, which differ from the corresponding compounds Ib1.1-Ib1.126 by the fact that R¹ is methyl and R² is methylsulfonyl.

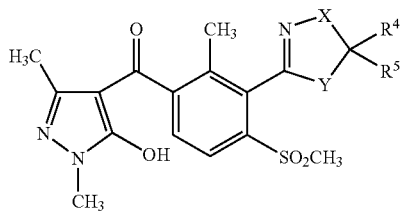

Ib3

The compounds Ib4.1-Ib4.126, which differ from the corresponding compounds Ib1.1-Ib1.126 by the fact R¹ is hydrogen and R² is methylsulfonyl.

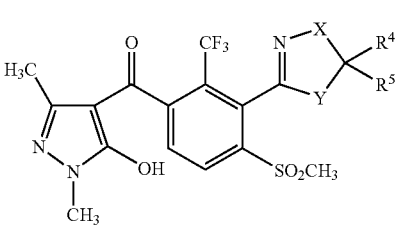

Ib4

The compounds Ib5.1-Ib5.126, which differ from the corresponding compounds Ib1.1-Ib1.126 by the fact that R¹ is trifluoromethyl and R² is methylsulfonyl.

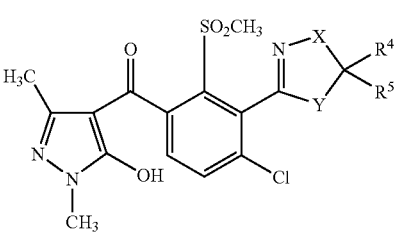

Ib5

The compounds Ib6.1-Ib6.126, which differ from the corresponding compounds Ib1.1-Ib1.126 by the fact that R¹ is methylsulfonyl.

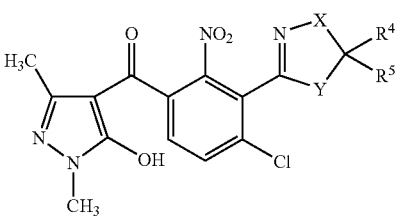

Ib6

The compounds Ib7.1-Ib7.126, which differ from the corresponding compounds Ib1.1-Ib1.126 by the fact that R¹ is nitro.

Ib7

The compounds Ib8.1-Ib8.126, which differ from the corresponding compounds Ib1.1-Ib1.126 by the fact that R² is trifluoromethyl.

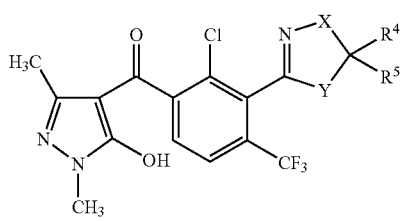
Ib8

The compounds Ib9.1-Ib9.126, which differ from the corresponding compounds Ib1.1-Ib1.126 by the fact that $R^2$ is methylthio.

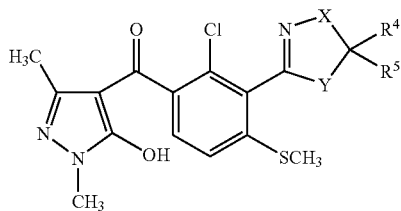
Ib9

The compounds Ib10.1-Ib10.126, which differ from the corresponding compounds Ib1.1-Ib1.126 by the fact that $R^2$ is methylsulfinyl.

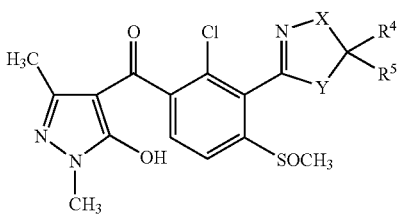
Ib10

The compounds Ib11.1-Ib11.126, which differ from the corresponding compounds Ib1.1-Ib1.126 by the fact that $R^2$ is trifluoromethylsulfonyl.

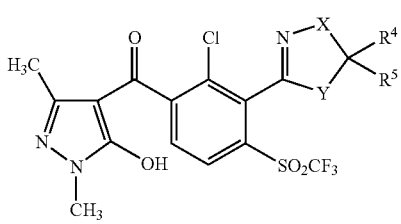
Ib11

The compounds Ib12.1-Ib12.126, which differ from the corresponding compounds Ib1.1-Ib1.126 by the fact that $R^1$ is methoxy and $R^2$ is methylsulfonyl.

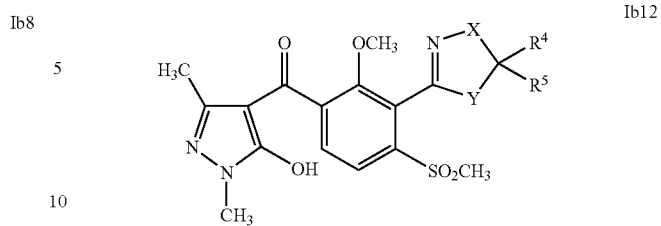
Ib12

The compounds Ib13.1-Ib13.126, which differ from the corresponding compounds Ib1.1-Ib1.126 by the fact that $R^2$ is ethylsulfonyl.

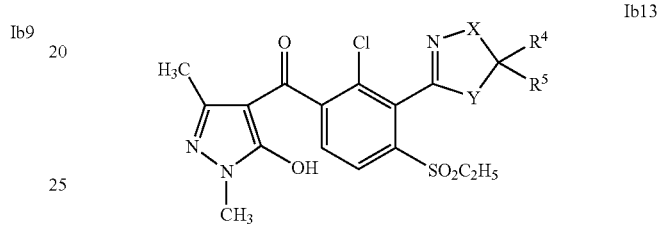
Ib13

The compounds Ib14.1-Ib14.126, which differ from the corresponding compounds Ib1.1-Ib1.126 by the fact $R^2$ is methylsulfonyl and $R^3$ is methyl.

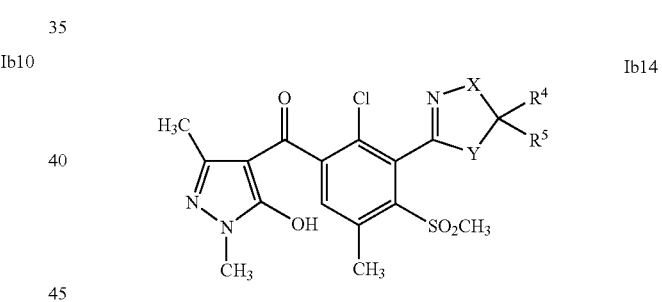
Ib14

The compounds Ib15.1-Ib15.126, which differ from the corresponding compounds Ib1.1-Ib1.126 by the fact that $R^2$ is methylsulfonyl and $R^3$ is chlorine.

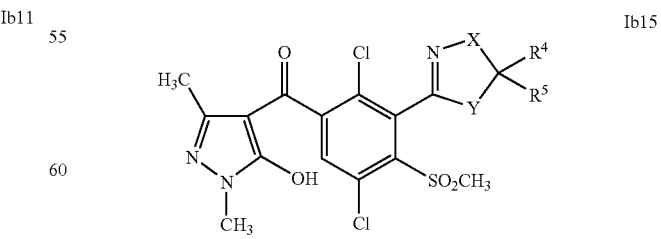
Ib15

The compounds Ib16.1-Ib16.126, which differ from the corresponding compounds Ib1.1-Ib1.126 by the fact that $R^1$ is methyl, $R^2$ is methylsulfonyl and $R^3$ is chlorine.

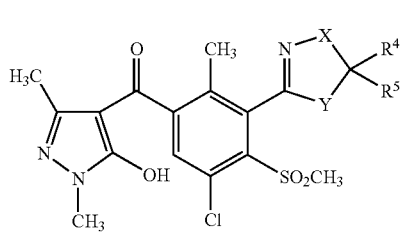

Ib16

The compounds Ib17.1-Ib17.126, which differ from the corresponding compounds Ib1.1-Ib1.126 by the fact that $R^1$ is methyl, $R^2$ is methylsulfonyl and $R^3$ is methyl.

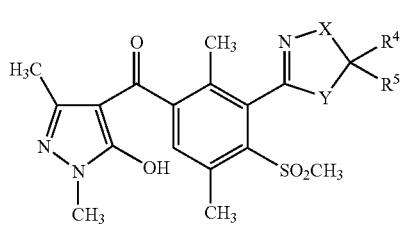

Ib17

The compounds Ib18.1-Ib18.126, which differ from the corresponding compounds Ib1.1-Ib1.126 by the fact that $R^1$ is methyl.

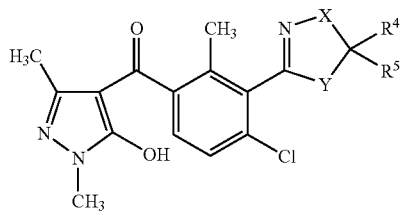

Ib18

The compounds Ib19.1-Ib19.126, which differ from the corresponding compounds Ib1.1-Ib1.126 by the fact that $R^1$ is methyl and $R^2$ is hydrogen.

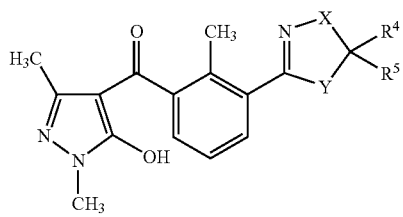

Ib19

The compounds Ib20.1-Ib20.126, which differ from the corresponding compounds Ib1.1-Ib1.126 by the fact $R^1$ is methyl and $R^2$ is nitro.

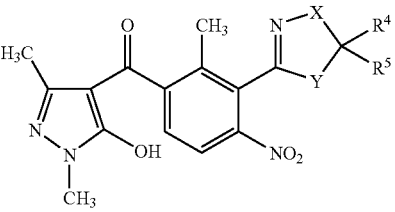

Ib20

The compounds Ib21.1-Ib21.126, which differ from the corresponding compounds Ib1.1-Ib1.126 by the fact that $R^2$ is methylsulfonyl and $R^{18}$ is hydrogen.

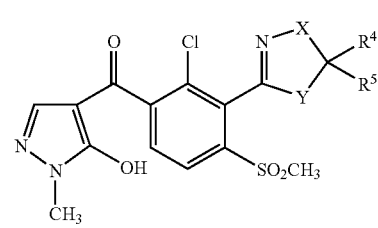

Ib21

The compounds Ib22.1-Ib22.126, which differ from the corresponding compounds Ib1.1-Ib1.126 by the fact that $R^2$ is nitro and $R^{18}$ is hydrogen.

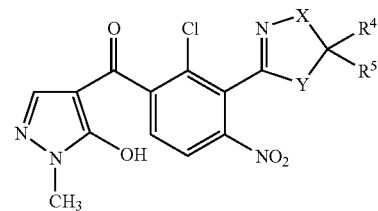

Ib22

The compounds Ib23.1-Ib23.126, which differ from the corresponding compounds Ib1.1-Ib1.126 by the fact that $R^1$ is methyl, $R^2$ is methylsulfonyl and $R^{18}$ is hydrogen.

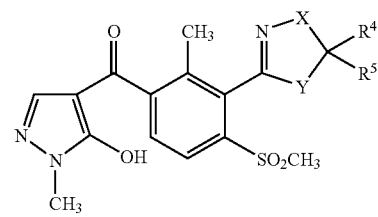

Ib23

The compounds Ib24.1-Ib24.126, which differ from the corresponding compounds Ib1.1-Ib1.126 by the fact that $R^1$ is hydrogen, $R^2$ is methylsulfonyl and $R^{18}$ is hydrogen.

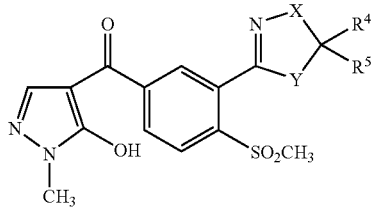

Ib24

The compounds Ib25.1-Ib25.126, which differ from the corresponding compounds Ib1.1-Ib1.126 by the fact that $R^1$ is trifluoromethyl, $R^2$ is methylsulfonyl and $R^{18}$ is hydrogen.

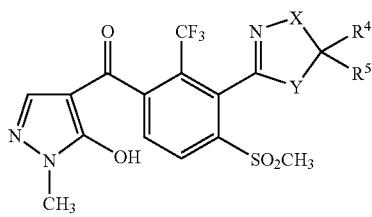

Ib25

The compounds Ib26.1-Ib26.126, which differ from the corresponding compounds Ib1.1-Ib1.126 by the fact that $R^1$ is methylsulfonyl and $R^{18}$ is hydrogen.

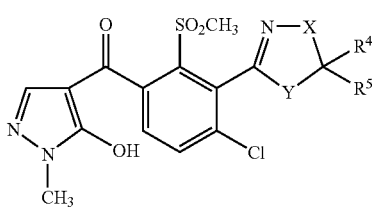

Ib26

The compounds Ib27.1-Ib27.126, which differ from the corresponding compounds Ib1.1-Ib1.126 by the fact $R^1$ is nitro and $R^{18}$ is hydrogen.

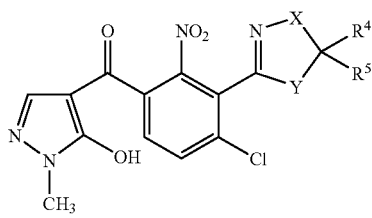

Ib27

The compounds Ib28.1-Ib28.126, which differ from the corresponding compounds Ib1.1-Ib1.126 by the fact that $R^2$ is trifluoromethyl and $R^{18}$ is hydrogen.

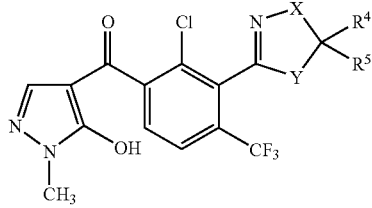

Ib28

The compounds Ib29.1-Ib29.126, which differ from the corresponding compounds Ib1.1-Ib1.126 by the fact that $R^2$ is methylthio and $R^{18}$ is hydrogen.

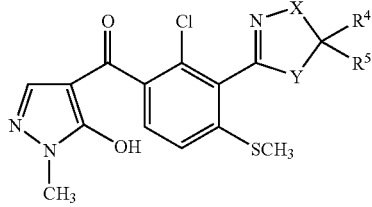

Ib29

The compounds Ib30.1-Ib30.126, which differ from the corresponding compounds Ib1.1-Ib1.126 by the fact that $R^2$ is methylsulfinyl and $R^{18}$ is hydrogen.

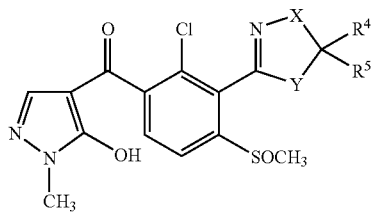

Ib30

The compounds Ib31.1-Ib31.126, which differ from the corresponding compounds Ib1.1-Ib1.126 by the fact that $R^2$ is trifluoromethylsulfonyl and $R^{18}$ is hydrogen.

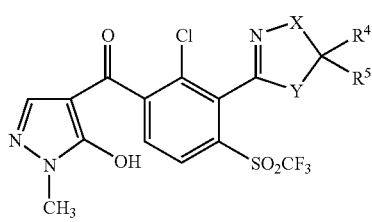

Ib31

The compounds Ib32.1-Ib32.126, which differ from the corresponding compounds Ib1.1-Ib1.126 by the fact that $R^1$ is methoxy, $R^2$ is methylsulfonyl and $R^{18}$ is hydrogen.

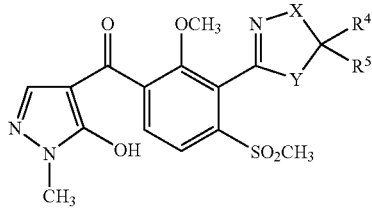
Ib32

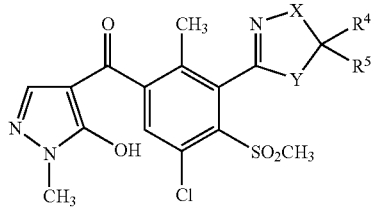
Ib36

The compounds Ib33.1-Ib33.126, which differ from the corresponding compounds Ib1.1-Ib1.126 by the fact that $R^2$ is ethylsulfonyl and $R^{18}$ is hydrogen.

The compounds Ib37.1-Ib37.126, which differ from the corresponding compounds Ib1.1-Ib1.126 by the fact that $R^1$ is methyl, $R^2$ is methylsulfonyl, $R^3$ is methyl and $R^{18}$ is hydrogen.

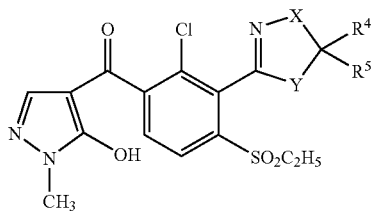
Ib33

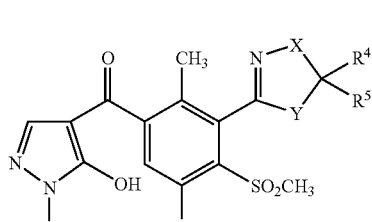
Ib37

The compounds Ib34.1-Ib34.126, which differ from the corresponding compounds Ib1.1-Ib1.126 by the fact that $R^2$ is methylsulfonyl, $R^3$ is methyl and $R^{18}$ is hydrogen.

The compounds Ib38.1-Ib38.126, which differ from the corresponding compounds Ib1.1-Ib1.126 by the fact that $R^1$ is methyl and $R^{18}$ is hydrogen.

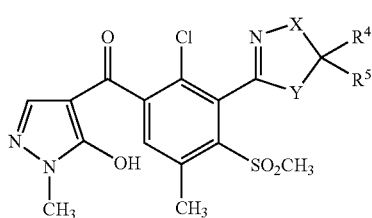
Ib34

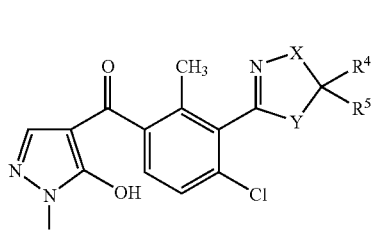
Ib38

The compounds Ib35.1-Ib35.126, which differ from the corresponding compounds Ib1.1-Ib1.126 by the fact that $R^2$ is methylsulfonyl, $R^3$ is chlorine and $R^{18}$ is hydrogen.

The compounds Ib39.1-Ib39.126, which differ from the corresponding compounds Ib1.1-Ib1.126 by the fact that $R^1$ is methyl, $R^2$ is hydrogen and $R^{18}$ is hydrogen.

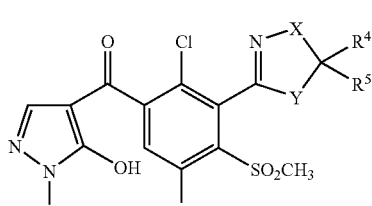
Ib35

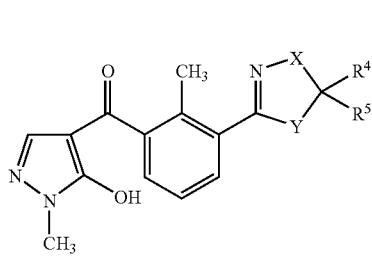
Ib39

The compounds Ib36.1-Ib36.126, which differ from the corresponding compounds Ib1.1-Ib1.126 by the fact that $R^1$ is methyl, $R^2$ is methylsulfonyl, $R^3$ is chlorine and $R^{18}$ is hydrogen.

The compounds Ib40.1-Ib40.126, which differ from the corresponding compounds Ib1.1-Ib1.126 by the fact that $R^1$ is methyl, $R^2$ is nitro and $R^{18}$ is hydrogen.

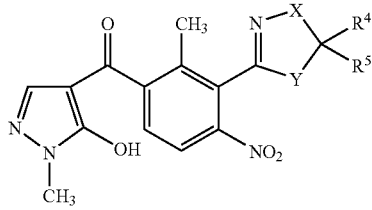

Ib40

The compounds Ib41.1-Ib41.126, which differ from the corresponding compounds Ib1.1-Ib1.126 by the fact that $R^2$ is nitro, $R^{16}$ is ethyl and $R^{18}$ is hydrogen.

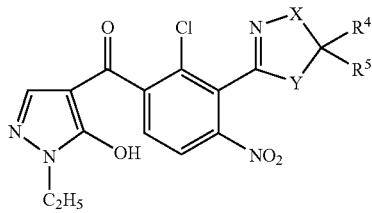

Ib41

The compounds Ib42.1-Ib42.126, which differ from the corresponding compounds Ib1.1-Ib1.126 by the fact that $R^1$ is methyl, $R^2$ is methylsulfonyl, $R^{16}$ is ethyl and $R^{18}$ is hydrogen.

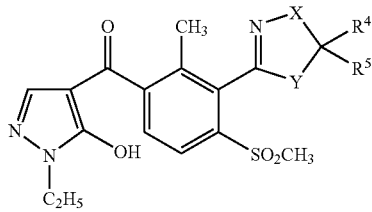

Ib42

The compounds Ib43.1-Ib43.126, which differ from the corresponding compounds Ib1.1-Ib1.126 by the fact that $R^1$ is hydrogen, $R^2$ is methylsulfonyl, $R^{16}$ is ethyl and $R^{18}$ is hydrogen.

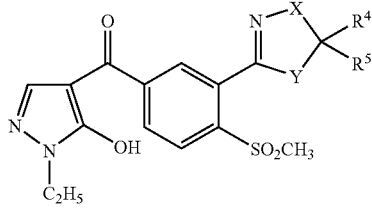

Ib43

The compounds Ib44.1-Ib44.126, which differ from the corresponding compounds Ib1.1-Ib1.126 by the fact that $R^1$ is trifluoromethyl, $R^2$ is methylsulfonyl, $R^{16}$ is ethyl and $R^{18}$ is hydrogen.

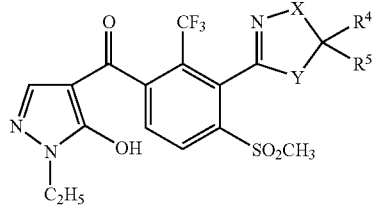

Ib44

The compounds Ib45.1-Ib45.126, which differ from the corresponding compounds Ib1.1-Ib1.126 by the fact that $R^1$ is methylsulfonyl, $R^{16}$ is ethyl and $R^{18}$ is hydrogen.

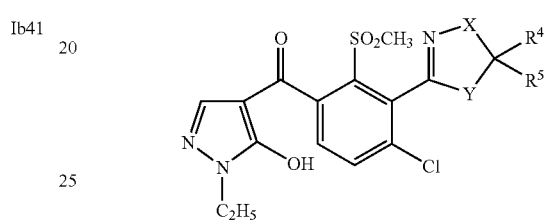

Ib45

The compounds Ib46.1-Ib46.126, which differ from the corresponding compounds Ib1.1-Ib1.126 by the fact that $R^1$ is nitro, $R^{16}$ is ethyl and $R^{18}$ is hydrogen.

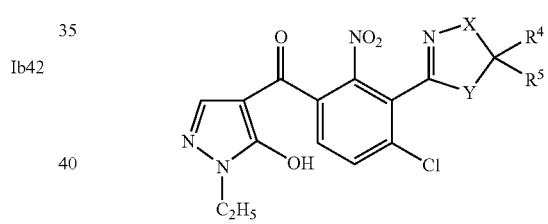

Ib46

The compounds Ib47.1-Ib47.126, which differ from the corresponding compounds Ib1.1-Ib1.126 by the fact that $R^2$ is trifluoromethyl, $R^{16}$ is ethyl and $R^{18}$ is hydrogen.

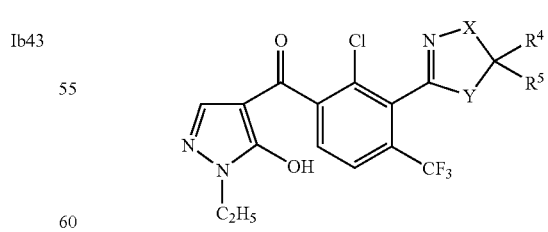

Ib47

The compounds Ib48.1-Ib48.126, which differ from the corresponding compounds Ib1.1-Ib1.126 by the fact that $R^2$ is methylthio, $R^{16}$ is ethyl and $R^{18}$ is hydrogen.

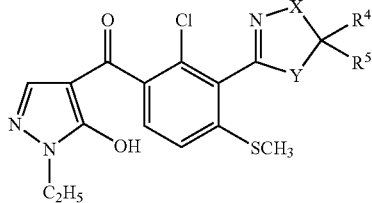

Ib48

The compounds Ib49.1-Ib49.126, which differ from the corresponding compounds Ib1.1-Ib1.126 by the fact that R² is methylsulfinyl, R¹⁶ is ethyl and R¹⁸ is hydrogen.

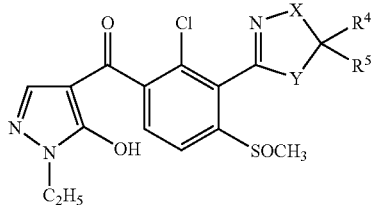

Ib49

The compounds Ib50.1-Ib50.126, which differ from the corresponding compounds Ib1.1-Ib1.126 by the fact that R² is trifluoromethylsulfonyl, R¹⁶ is ethyl and R¹⁸ is hydrogen.

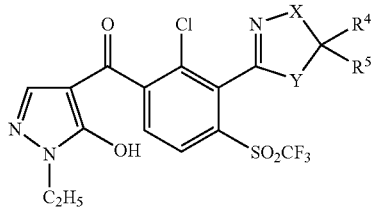

Ib50

The compounds Ib51.1-Ib51.126, which differ from the corresponding compounds Ib1.1-Ib1.126 by the fact that R¹ is methoxy, R² is methylsulfonyl, R¹⁶ is ethyl and R¹⁸ is hydrogen.

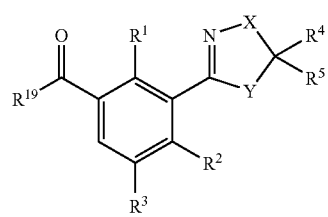

III wherein

R¹⁹ is hydroxyl or $C_1$-$C_6$-alkoxy;
R¹ is $C_1$-$C_6$-alkyl;
R² is $C_1$-$C_6$-alkylthio or $C_1$-$C_6$-alkylsulfonyl;
R³ is hydrogen;
R⁴ and R⁵ are hydrogen or $C_1$-$C_4$-alkyl;

X is $CR^{10}R^{11}$, wherein R¹⁰ and R¹¹ are hydrogen or $C_1$-$C_4$-alkyl, and Y is oxygen.

29. A process for the preparation of the 3-heterocyclyl-substituted benzoyl compound of the formula I defined in claim 28, which comprises acylating a pyrazole of the formula II

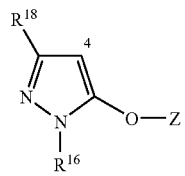

II with an activated carboxylic acid IIIα or with a carboxylic acid IIIβ

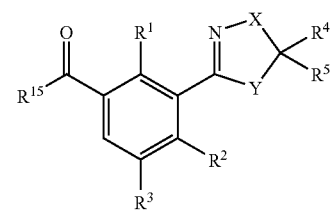

IIIα

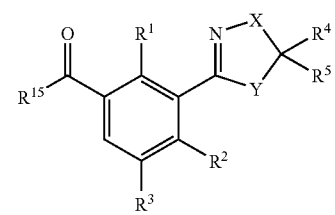

IIIβ

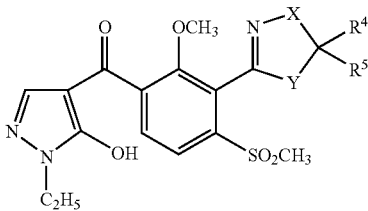

Ib51

The compounds Ib52.1-Ib52.126, which differ from the corresponding compounds Ib1.1-Ib1.126 by the fact that R² is ethylsulfonyl, R¹⁶ is ethyl and R¹⁸ is hydrogen.

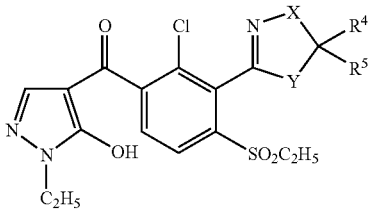

Ib52

The compounds Ib53.1-Ib53.126, which differ from the corresponding compounds Ib1.1-Ib1.126 by the fact that $R^2$ is methylsulfonyl, $R^3$ is methyl, $R^{16}$ is ethyl and $R^{18}$ is hydrogen.

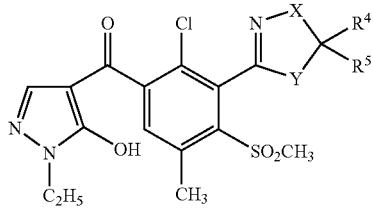

Ib53

The compounds Ib54.1-Ib54.126, which differ from the corresponding compounds Ib1.1-Ib1.126 by the fact that $R^2$ is methylsulfonyl, $R^3$ is chlorine, $R^{16}$ is ethyl and $R^{18}$ is hydrogen.

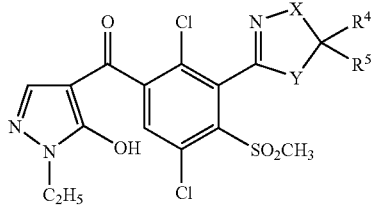

Ib54

The compounds Ib55.1-Ib55.126, which differ from the corresponding compounds Ib1.1-Ib1.126 by the fact that $R^1$ is methyl, $R^2$ is methylsulfonyl, $R^3$ is chlorine, $R^{16}$ is ethyl and $R^{18}$ is hydrogen.

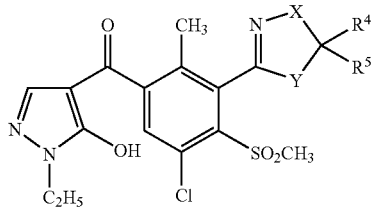

Ib55

The compounds Ib56.1-Ib56.126, which differ from the corresponding compounds Ib1.1-Ib1.126 by the fact that $R^1$ is methyl, $R^2$ is methylsulfonyl, $R^3$ is methyl, $R^{16}$ is ethyl and $R^{18}$ is hydrogen.

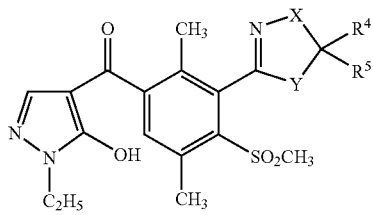

Ib56

The compounds Ib57.1-Ib57.126, which differ from the corresponding compounds Ib1.1-Ib1.126 by the fact that $R^1$ is methyl, $R^{16}$ is ethyl and $R^{18}$ is hydrogen.

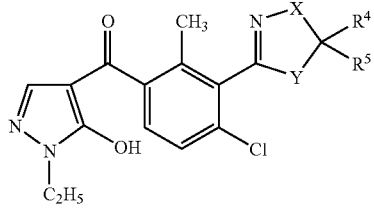

Ib57

The compounds Ib58.1-Ib58.126, which differ from the corresponding compounds Ib1.1-Ib1.126 by the fact that $R^1$ is methyl, $R^2$ is hydrogen, $R^{16}$ is ethyl and $R^{18}$ is hydrogen.

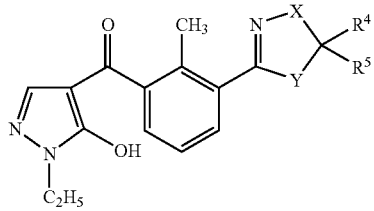

Ib58

The compounds Ib59.1-Ib59.126, which differ from the corresponding compounds Ib1.1-Ib1.126 by the fact that $R^1$ is methyl, $R^2$ is nitro, $R^{16}$ is ethyl and $R^{18}$ is hydrogen.

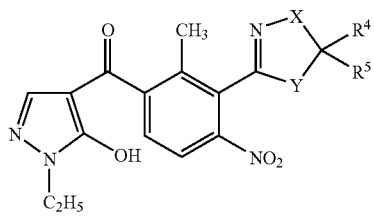

Ib59

The compounds Ib61.1-Ib61.126 [sic], which differ from the corresponding compounds Ib1.1-Ib1.126 by the fact that $R^2$ is methylsulfonyl, $R^{16}$ is n-propyl and $R^{18}$ is hydrogen.

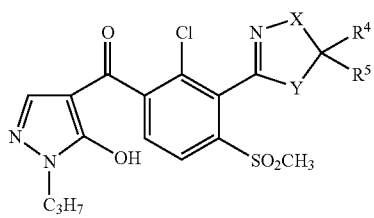

Ib60

The compounds Ib61.1-Ib61.126, which differ from the corresponding compounds Ib1.1-Ib1.126 by the fact that $R^2$ is nitro, $R^{16}$ is n-propyl and $R^{18}$ is hydrogen.

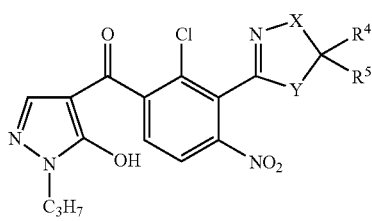
Ib61

The compounds Ib62.1-Ib62.126, which differ from the corresponding compounds Ib1.1-Ib1.126 by the fact that $R^1$ is methyl, $R^2$ is methylsulfonyl, $R^{16}$ is n-propyl and $R^{18}$ is hydrogen.

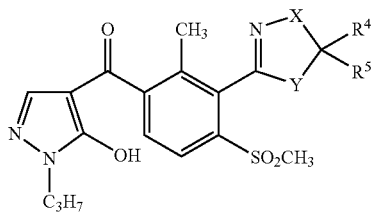
Ib62

The compounds Ib63.1-Ib63.126, which differ from the corresponding compounds Ib1.1-Ib1.126 by the fact that $R^1$ is hydrogen, $R^2$ is methylsulfonyl, $R^{16}$ is n-propyl and $R^{18}$ is hydrogen.

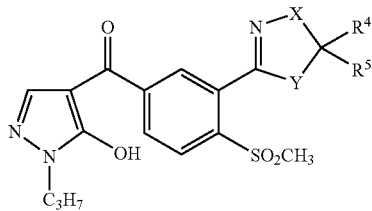
Ib63

The compounds Ib64.1-Ib64.126, which differ from the corresponding compounds Ib1.1-Ib1.126 by the fact that $R^1$ is trifluoromethyl, $R^2$ is methylsulfonyl, $R^{16}$ is n-propyl and $R^{18}$ is hydrogen.

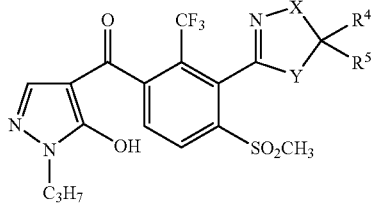
Ib64

The compounds Ib65.1-Ib65.126, which differ from the corresponding compounds Ib1.1-Ib1.126 by the fact that $R^1$ is methylsulfonyl, $R^{16}$ is n-propyl and $R^{18}$ is hydrogen.

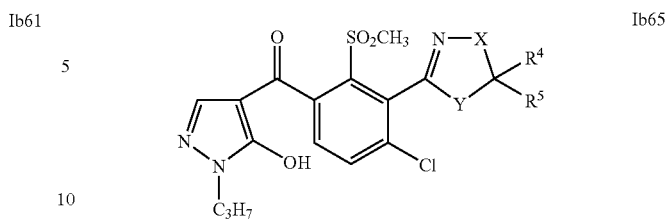
Ib65

The compounds Ib66.1-Ib66.126, which differ from the corresponding compounds Ib1.1-Ib1.126 by the fact that $R^1$ is nitro, $R^{16}$ is n-propyl and $R^{18}$ is hydrogen.

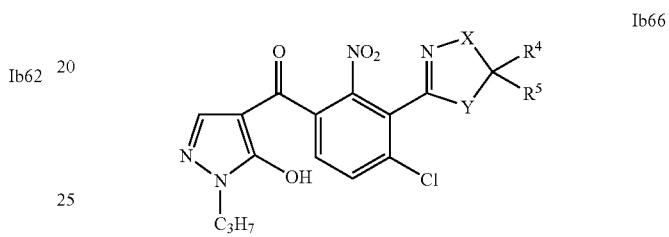
Ib66

The compounds Ib67.1-Ib67.126, which differ from the corresponding compounds Ib1.1-Ib1.126 by the fact that $R^2$ is trifluoromethyl, $R^{16}$ is n-propyl and $R^{18}$ is hydrogen.

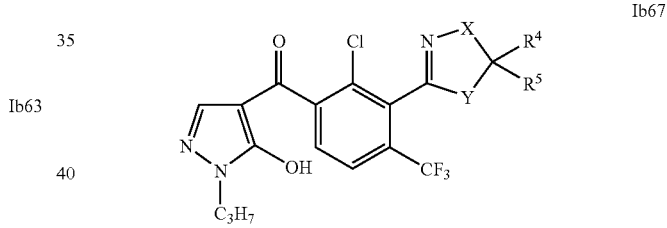
Ib67

The compounds Ib68.1-Ib68.126, which differ from the corresponding compounds Ib1.1-Ib1.126 by the fact that $R^2$ is methylthio, $R^{16}$ is n-propyl and $R^{18}$ is hydrogen.

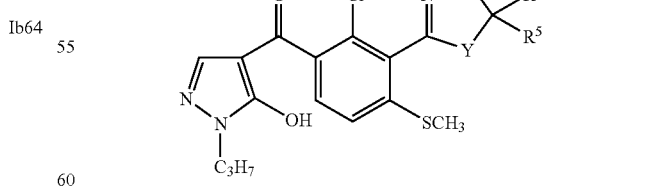
Ib68

The compounds Ib69.1-Ib69.126, which differ from the corresponding compounds Ib1.1-Ib1.126 by the fact that $R^2$ is methylsulfinyl, $R^{16}$ is n-propyl and $R^{18}$ is hydrogen.

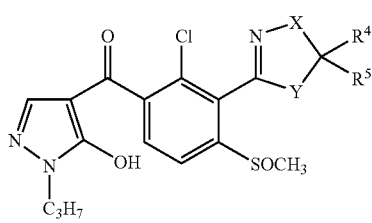
Ib69

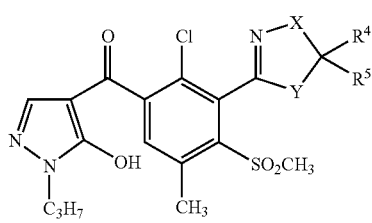
Ib73

The compounds Ib70.1-Ib70.126, which differ from the corresponding compounds Ib1.1-Ib1.126 by the fact that $R^2$ is trifluoromethylsulfonyl, $R^{16}$ is n-propyl and $R^{18}$ is hydrogen.

The compounds Ib74.1-Ib74.126, which differ from the corresponding compounds Ib1.1-Ib1.126 by the fact that $R^2$ is methylsulfonyl, $R^3$ is chlorine, $R^{16}$ is n-propyl and $R^{18}$ is hydrogen.

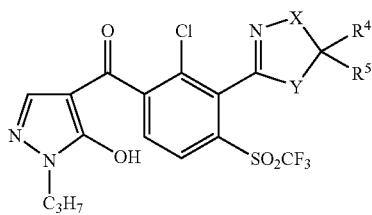
Ib70

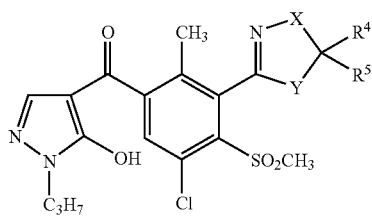
Ib74

The compounds Ib71.1-Ib71.126, which differ from the corresponding compounds Ib1.1-Ib1.126 by the fact that $R^1$ is methoxy, $R^2$ is methylsulfonyl, $R^{16}$ is n-propyl and $R^{18}$ is hydrogen.

The compounds Ib75.1-Ib75.126, which differ from the corresponding compounds Ib1.1-Ib1.126 by the fact that $R^1$ is methyl, $R^2$ is methylsulfonyl, $R^3$ is chlorine, $R^{16}$ is n-propyl and $R^8$ is hydrogen.

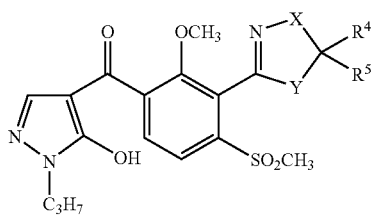
Ib71

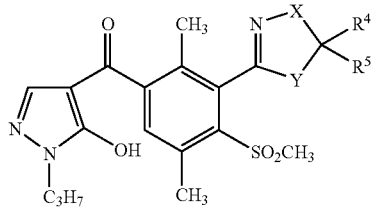
Ib75

The compounds Ib72.1-Ib72.126, which differ from the corresponding compounds Ib1.1-Ib1.126 by the fact that $R^2$ is ethylsulfonyl, $R^{16}$ is n-propyl and $R^{18}$ is hydrogen.

The compounds Ib76.1-Ib76.126, which differ from the corresponding compounds Ib1.1-Ib1.126 by the fact that $R^1$ is methyl, $R^2$ is methylsulfonyl, $R^3$ is methyl, $R^6$ is n-propyl and $R^{18}$ is hydrogen.

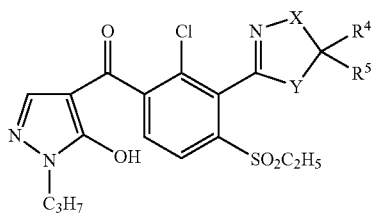
Ib72

Ib76

The compounds Ib73.1-Ib73.126, which differ from the corresponding compounds Ib1.1-Ib1.126 by the fact that $R^2$ is methylsulfonyl, $R^3$ is methyl, $R^{16}$ is n-propyl and $R^{18}$ is hydrogen.

The compounds Ib77.1-Ib77.126, which differ from the corresponding compounds Ib1.1-Ib1.126 by the fact that $R^1$ is methyl, $R^{16}$ is n-propyl and $R^{18}$ is hydrogen.

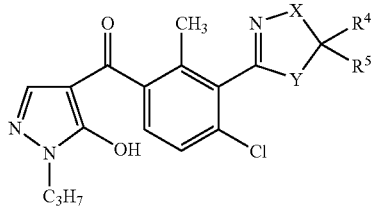

Ib77

The compounds Ib78.1-Ib78.126, which differ from the corresponding compounds Ib1.1-Ib1.126 by the fact that $R^1$ is methyl, $R^2$ is hydrogen, $R^{16}$ is n-propyl and $R^{18}$ is hydrogen.

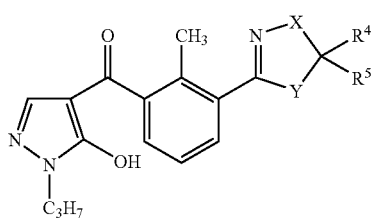

Ib78

The compounds Ib79.1-Ib79.126, which differ from the corresponding compounds Ib1.1-Ib1.126 by the fact that $R^1$ is methyl, $R^2$ is nitro, $R^{16}$ is n-propyl and $R^{18}$ is hydrogen.

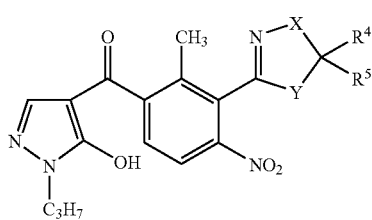

Ib79

The compounds Ib80.1-Ib80.126, which differ from the corresponding compounds Ib1.1-Ib1.126 by the fact that $R^{16}$ is n-propyl and $R^{18}$ is hydrogen.

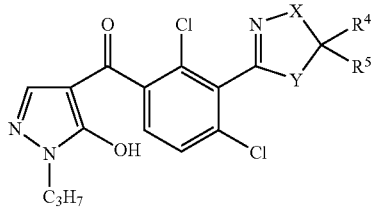

Ib80

The compounds Ib81.1-Ib81.126, which differ from the corresponding compounds Ib1.1-Ib1.126 by the fact that $R^2$ is methylsulfonyl, $R^{16}$ is n-butyl and $R^{18}$ is hydrogen.

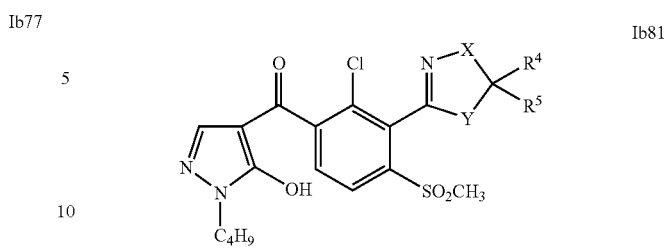

Ib81

The compounds Ib82.1-Ib82.126, which differ from the corresponding compounds Ib1.1-Ib1.126 by the fact that $R^2$ is nitro, $R^{16}$ is n-butyl and $R^{18}$ is hydrogen.

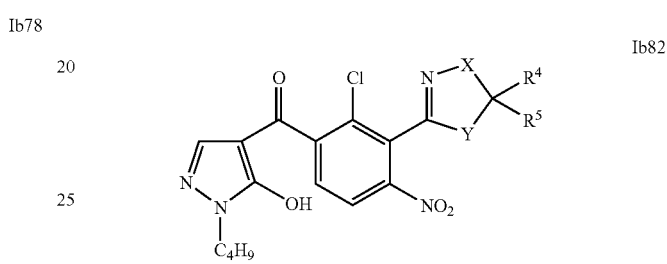

Ib82

The compounds Ib83.1-Ib83.126, which differ from the corresponding compounds Ib1.1-Ib1.126 by the fact that $R^1$ is methyl, $R^2$ is methylsulfonyl, $R^{16}$ is n-butyl and $R^{18}$ is hydrogen.

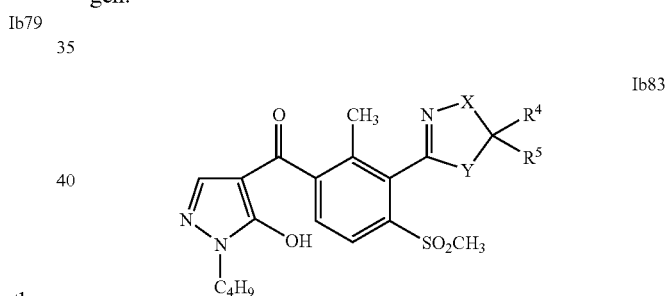

Ib83

The compounds Ib84.1-Ib84.126, which differ from the corresponding compounds Ib1.1-Ib1.126 by the fact that $R^1$ is hydrogen, $R^2$ is methylsulfonyl, $R^{16}$ is n-butyl and $R^{18}$ is hydrogen.

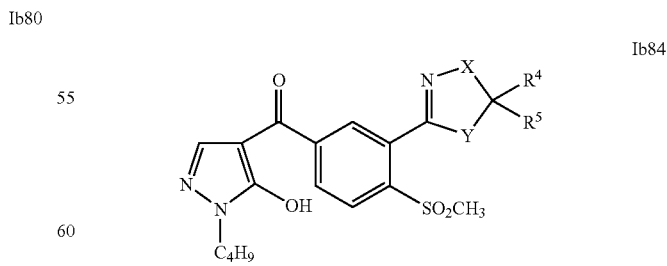

Ib84

The compounds Ib85.1-Ib85.126, which differ from the corresponding compounds Ib1.1-Ib1.126 by the fact that $R^1$ is trifluoromethyl, $R^2$ is methylsulfonyl, $R^{16}$ is n-butyl and $R^{18}$ is hydrogen.

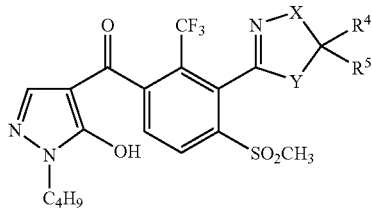

Ib85

The compounds Ib86.1-Ib86.126, which differ from the corresponding compounds Ib1.1-Ib1.126 by the fact that $R^1$ is methylsulfonyl, $R^{16}$ is n-butyl and $R^{18}$ is hydrogen.

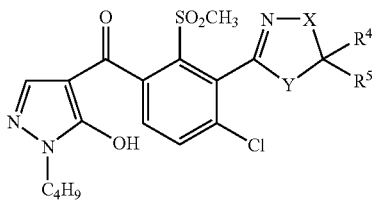

Ib86

The compounds Ib87.1-Ib87.126, which differ from the corresponding compounds Ib1.1-Ib1.126 by the fact that $R^1$ is nitro, $R^{16}$ is n-butyl and $R^{18}$ is hydrogen.

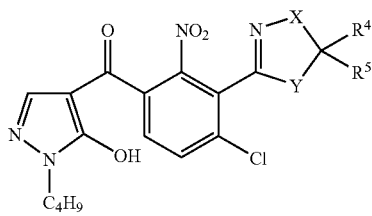

Ib87

The compounds Ib88.1-Ib88.126, which differ from the corresponding compounds Ib1.1-Ib1.126 by the fact that $R^2$ is trifluoromethyl, $R^{16}$ is n-butyl and $R^{18}$ is hydrogen.

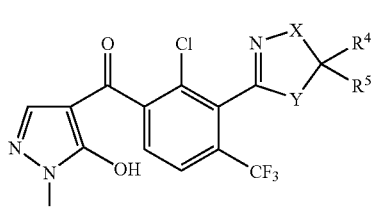

Ib88

The compounds Ib89.1-Ib89.126, which differ from the corresponding compounds Ib1.1-Ib1.126 by the fact that $R^2$ is methylthio, $R^{16}$ is n-butyl and $R^{18}$ is hydrogen.

Ib89

The compounds Ib90.1-Ib90.126, which differ from the corresponding compounds Ib1.1-Ib1.126 by the fact that $R^2$ is methylsulfinyl, $R^{16}$ is n-butyl and $R^{18}$ is hydrogen.

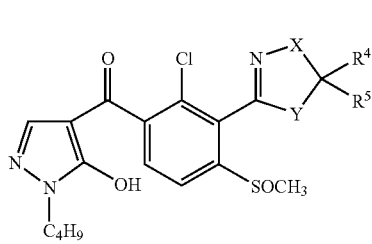

Ib90

The compounds Ib91.1-Ib91.126, which differ from the corresponding compounds Ib1.1-Ib1.126 by the fact that $R^2$ is trifluoromethylsulfonyl, $R^{16}$ is n-butyl and $R^{18}$ is hydrogen.

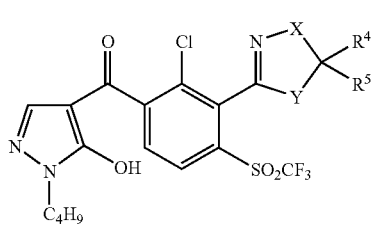

Ib91

The compounds Ib92.1-Ib92.126, which differ from the corresponding compounds Ib1.1-Ib1.126 by the fact that $R^1$ is methoxy, $R^2$ is methylsulfonyl, $R^{16}$ is n-butyl and $R^{18}$ is hydrogen.

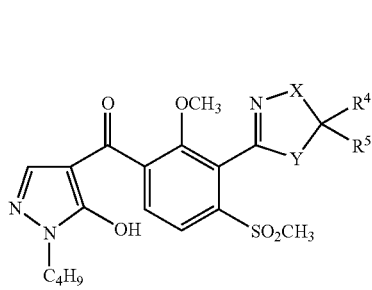

Ib92

The compounds Ib93.1-Ib93.126, which differ from the corresponding compounds Ib1.1-Ib1.126 by the fact that $R^2$ is ethylsulfonyl, $R^{16}$ is n-butyl and $R^{18}$ is hydrogen.

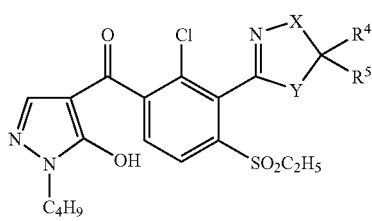
Ib93

The compounds Ib94.1-Ib94.126, which differ from the corresponding compounds Ib1.1-Ib1.126 by the fact that $R^2$ is methylsulfonyl, $R^3$ is methyl, $R^{16}$ is n-butyl and $R^{18}$ is hydrogen.

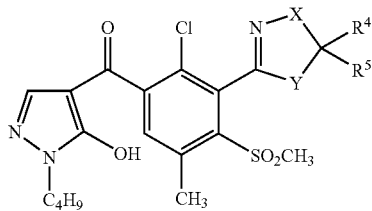
Ib94

The compounds Ib95.1-Ib95.126, which differ from the corresponding compounds Ib1.1-Ib1.126 by the fact that $R^2$ is methylsulfonyl, $R^3$ is chlorine, $R^{16}$ is n-butyl and $R^{18}$ is hydrogen.

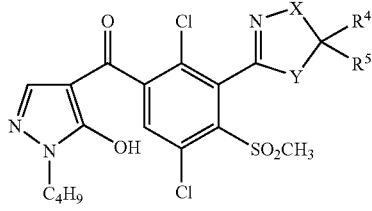
Ib95

The compounds Ib96.1-Ib96.126, which differ from the corresponding compounds Ib1.1-Ib1.126 by the fact that $R^1$ is methyl, $R^2$ is methylsulfonyl, $R^3$ is chlorine, $R^{16}$ is n-butyl and $R^{18}$ is hydrogen.

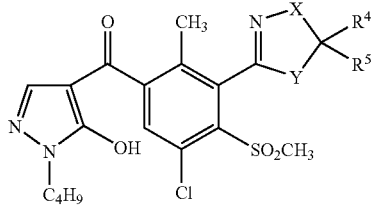
Ib96

The compounds Ib97.1-Ib97.126, which differ from the corresponding compounds Ib1.1-Ib1.126 by the fact that $R^1$ is methyl, $R^2$ is methylsulfonyl, $R^3$ is methyl, $R^{16}$ is n-butyl and $R^{18}$ is hydrogen.

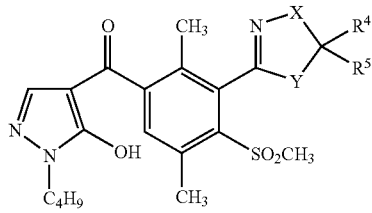
Ib97

The compounds Ib98.1-Ib98.126, which differ from the corresponding compounds Ib1.1-Ib1.126 by the fact that $R^1$ is methyl, $R^{16}$ is n-butyl and $R^{18}$ is hydrogen.

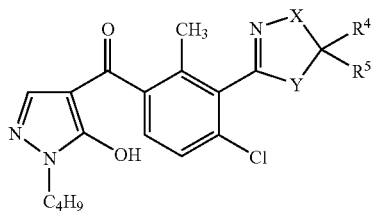
Ib98

The compounds Ib99.1-Ib99.126, which differ from the corresponding compounds Ib1.1-Ib1.126 by the fact that $R^1$ is methyl, $R^2$ is hydrogen, $R^{16}$ is n-butyl and $R^{18}$ is hydrogen.

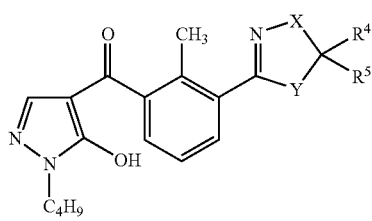
Ib99

The compounds Ib100.1-Ib100.126, which differ from the corresponding compounds Ib1.1-Ib1.126 by the fact that $R^1$ is methyl, $R^2$ is nitro, $R^{16}$ is n-butyl and $R^{18}$ is hydrogen.

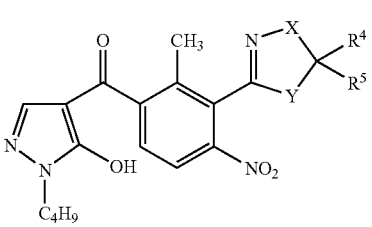
Ib100

The compounds Ib101.1-Ib101.126, which differ from the corresponding compounds Ib1.1-Ib1.126 by the fact that $R^{16}$ is n-butyl and $R^{18}$ is hydrogen.

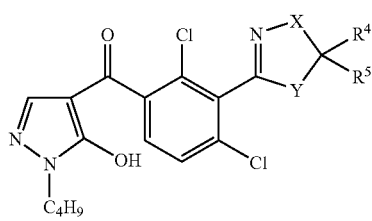
Ib101

The compounds Ib102.1-Ib102.126, which differ from the corresponding compounds Ib1.1-Ib1.126 by the fact that $R^2$ is methylsulfonyl, $R^{16}$ is iso-butyl and $R^{18}$ is hydrogen.

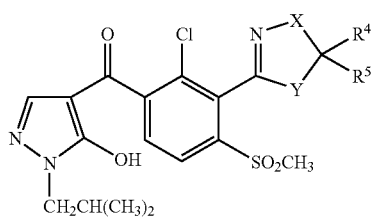
Ib102

The compounds Ib103.11-b103.126, which differ from the corresponding compounds Ib1.1-Ib1.126 by the fact that $R^2$ is nitro, $R^{16}$ is iso butyl and $R^{18}$ is hydrogen.

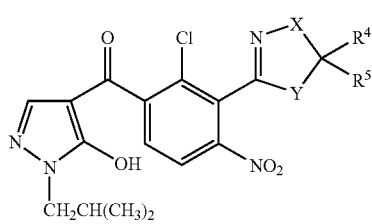
Ib103

The compounds Ib104.1-b104.126, which differ from the corresponding compounds Ib1.1-Ib1.126 by the fact that $R^1$ is methyl, $R^2$ is methylsulfonyl, $R^{16}$ is iso-butyl and $R^{18}$ is hydrogen.

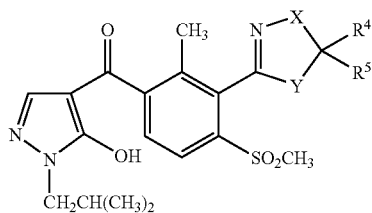
Ib104

The compounds Ib105.1-Ib105.126, which differ from the corresponding compounds Ib1.1-Ib1.126 by the fact that $R^1$ is hydrogen, $R^2$ is methylsulfonyl, $R^{16}$ is iso-butyl and $R^{18}$ is hydrogen.

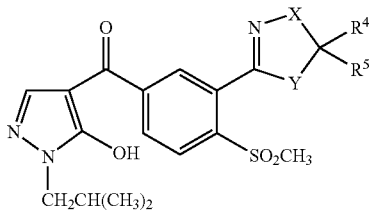
Ib105

The compounds Ib106.1-Ib106.126, which differ from the corresponding compounds Tb1.1-Ib1.126 by the fact that $R^1$ is trifluoromethyl, $R^2$ is methylsulfonyl, $R^{16}$ is iso-butyl and $R^{18}$ is hydrogen.

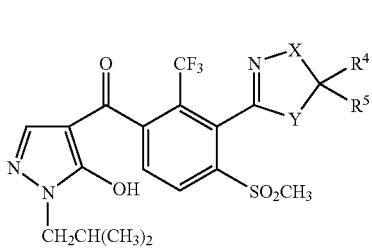
Ib106

The compounds Ib107.1-Ib107.126, which differ from the corresponding compounds Ib1.1Ib1.126 by the fact that $R^1$ is methylsulfonyl, $R^{16}$ is iso-butyl and $R^{18}$ is hydrogen.

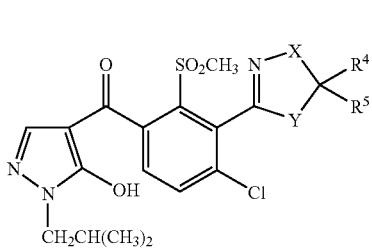
Ib107

The compounds Ib108.1-Ib108.126, which differ from the corresponding compounds Ib1.1-Ib1.126 by the fact that $R^1$ is nitro, $R^{16}$ is iso-butyl and $R^{18}$ is hydrogen.

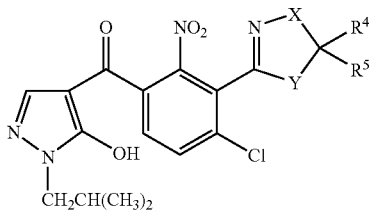
Ib108

The compounds Ib109.1-Ib109.126, which differ from the corresponding compounds Ib1.1-Ibl1.126 by the fact that $R^2$ is trifluoromethyl, $R^{16}$ is iso-butyl and $R^{18}$ is hydrogen.

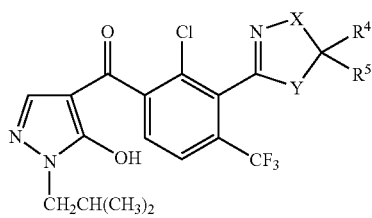
Ib109

The compounds Ib110.1Ib110.126, which differ from the corresponding compounds Ib1.1-Ib1.126 by the fact that $R^2$ is methylthio, $R^6$ is iso-butyl and $R^{18}$ is hydrogen.

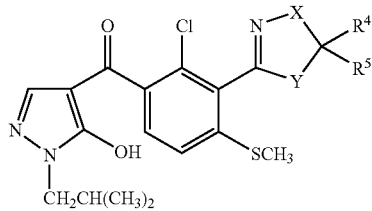
Ib110

The compounds Ib111.1-Ib111.126, which differ from the corresponding compounds Ib1.1-Ib1.126 by the fact that $R^2$ is methylsulfinyl, $R^{16}$ is iso-butyl and $R^{18}$ is hydrogen.

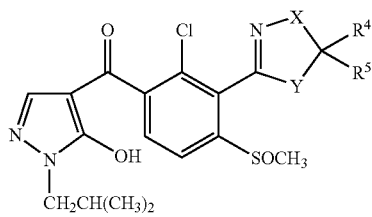
Ib111

The compounds Ib112.1-Ib112.126, which differ from the corresponding compounds Ib1.1-Ib1.126 by the fact that $R^2$ is trifluoromethylsulfonyl, $R^{16}$ is iso-butyl and $R^{18}$ is hydrogen.

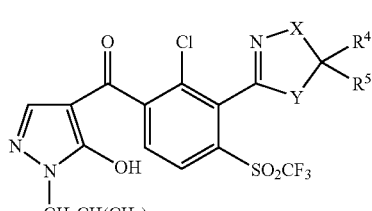
Ib112

The compounds Ib114.1-Ib114.126, which differ from the corresponding compounds Ib1.1-Ib1.126 by the fact that $R^1$ is methoxy, $R^2$ is methylsulfonyl, $R^{16}$ is iso-butyl and $R^{18}$ is hydrogen.

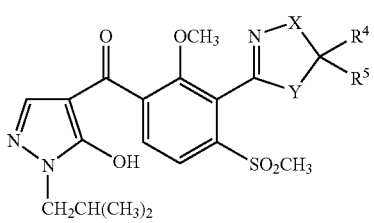
Ib113

The compounds Ib114.1Ib114.126, which differ from the corresponding compounds Ib1.1-Ib1.126 by the fact that $R^2$ is ethylsulfonyl, $R^{16}$ is iso-butyl and $R^{18}$ is hydrogen.

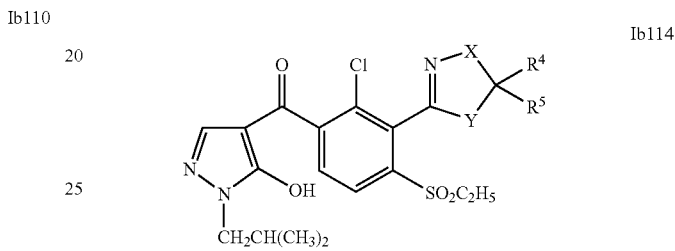
Ib114

The compounds Ib115.1-Ib115.126, which differ from the corresponding compounds Ib1.1-Ib1.126 by the fact that $R^2$ is methylsulfonyl, $R^3$ is methyl, $R^{16}$ is iso-butyl and $R^{18}$ is hydrogen.

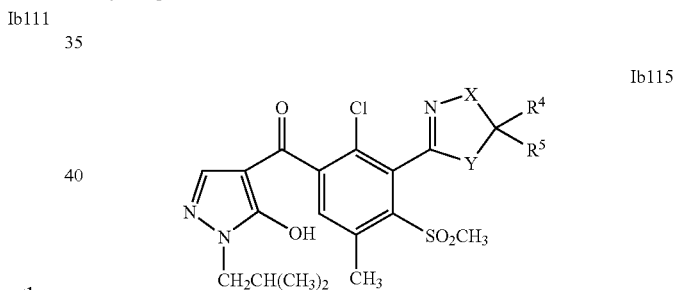
Ib115

The compounds Ib116.1-Ib116.126, which differ from the corresponding compounds Ib1.1-Ib1.126 by the fact that $R^2$ is methylsulfonyl, $R^3$ is chlorine, $R^{16}$ is iso-butyl and $R^{18}$ is hydrogen.

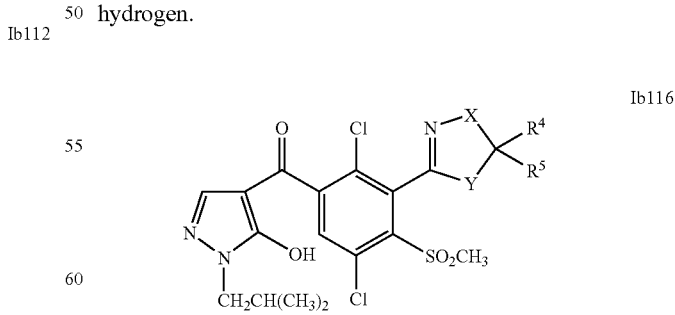
Ib116

The compounds Ib117.1-Ib117.126, which differ from the corresponding compounds Ib1.1-Ib1.126 by the fact that $R^1$ is methyl, $R^2$ is methylsulfonyl, $R^3$ is chlorine, $R^{16}$ is iso-butyl and $R^{18}$ is hydrogen.

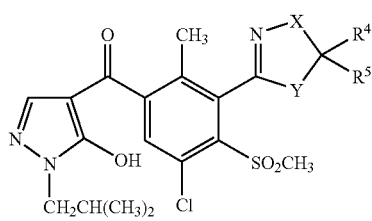
Ib117

The compounds Ib118.1-Ib118.126, which differ from the corresponding compounds Ib1.1-Ib1.126 by the fact that $R^1$ is methyl, $R^2$ is methylsulfonyl, $R^3$ is methyl, $R^{16}$ is iso-butyl and $R^{18}$ is hydrogen.

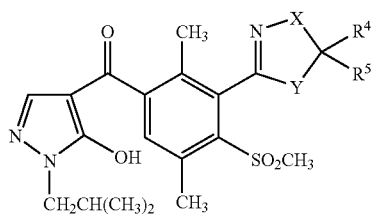
Ib118

The compounds Ib119.1-Ib119.126, which differ from the corresponding compounds Ib1.1-Ib1.126 by the fact that $R^1$ is methyl, $R^{16}$ is iso-butyl and $R^{18}$ is hydrogen.

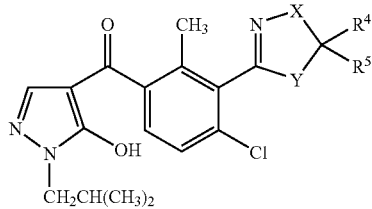
Ib119

The compounds Ib120.1-Ib120.126, which differ from the corresponding compounds Ib1.1-Ib1.126 by the fact that $R^1$ is methyl, $R^2$ is hydrogen, $R^{16}$ is iso-butyl and $R^{18}$ is hydrogen.

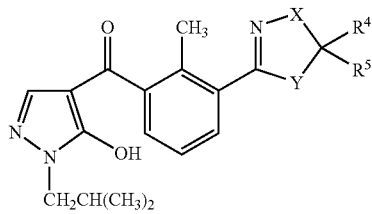
Ib120

The compounds Ib121.1-Ib121.126, which differ from the corresponding compounds Ib1.1-Ib1.126 by the fact that $R^1$ is methyl, $R^2$ is nitro, $R^{16}$ is iso-butyl and $R^{18}$ is hydrogen.

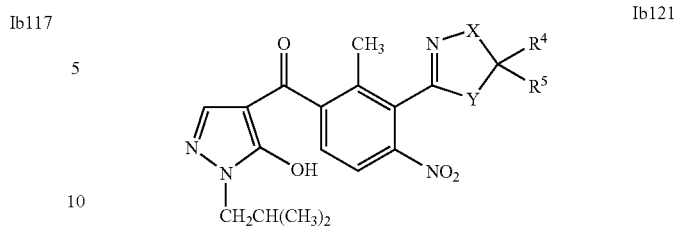
Ib121

The compounds Ib122.1-Ib122.126, which differ from the corresponding compounds Ib1.1-Ib1.126 by the fact that $R^{16}$ is iso-butyl and $R^{18}$ is hydrogen.

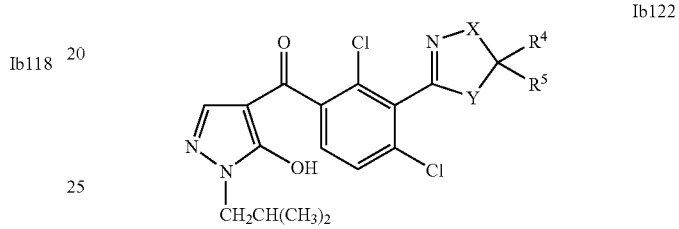
Ib122

The compounds Ib123.1-Ib123.126, which differ from the corresponding compounds Ib1.1-Ib1.126 by the fact $R^1$ is methylsulfonyl and $R^2$ is trifluoromethyl.

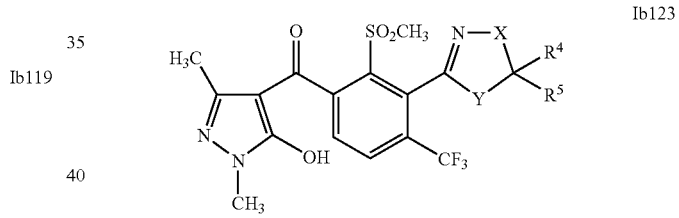
Ib123

The compounds Ib124.1-Ib124.126, which differ from the corresponding compounds Ib1.1-Ib1.126 by the fact that $R^1$ is methylsulfonyl, $R^2$ is trifluoromethyl, and $R^{18}$ is hydrogen.

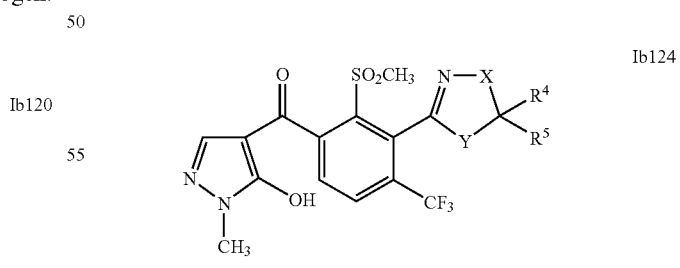
Ib124

The compounds Ib125.1-Ib125.126, which differ from the corresponding compounds Ib1.1-Ib1.126 by the fact that $R^1$ is methylsulfonyl, $R^2$ is trifluoromethyl, $R^{16}$ is n-propyl and $R^{18}$ is hydrogen.

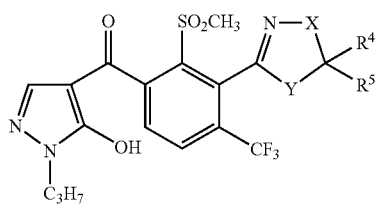
Ib125

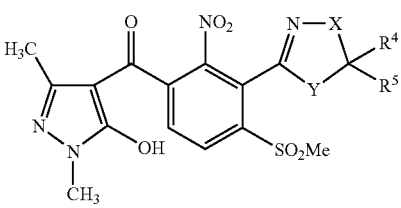
Ib129

The compounds Ib126.1-Ib126.126, which differ from the corresponding compounds Ib1.1-Ib1.126 by the fact that $R^1$ is methylsulfonyl, $R^2$ is trifluoromethyl, $R^{16}$ is n-butyl and $R^{18}$ is hydrogen.

The compounds Ib130.1-Ib130.126, which differ from the corresponding compounds Ib1.1-Ib1.126 by the fact that $R^1$ is nitro, $R^2$ is methylsulfonyl and $R^{18}$ is hydrogen.

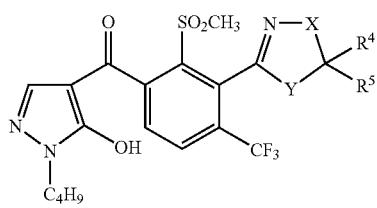
Ib126

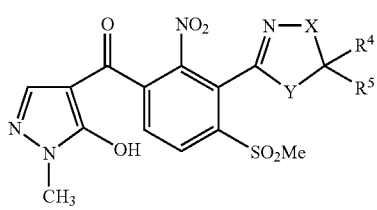
Ib130

The compounds Ib127.1-Ib127.126, which differ from the corresponding compounds Ib1.1-Ib1.126 by the fact that $R^1$ is methylsulfonyl, $R^2$ is trifluoromethyl, $R^{16}$ is iso-butyl and $R^{18}$ is hydrogen.

The compounds Ib131.1-Ib131.126, which differ from the corresponding compounds Ib1.1-Ib1.126 by the fact that $R^1$ is nitro, $R^2$ is methylsulfonyl, $R^{16}$ is n-propyl and $R^{18}$ is hydrogen.

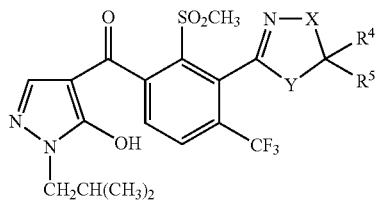
Ib127

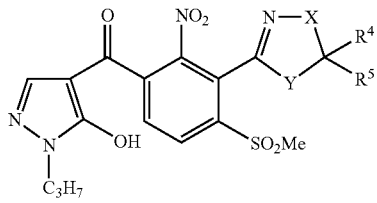
Ib131

The compounds Ib128.1-Ib128.126, which differ from the corresponding compounds Ib1.1-Ib1.126 by the fact that $R^1$ is methylsulfonyl, $R^2$ is trifluoromethyl, $R^{16}$ is ethyl and $R^{18}$ is hydrogen.

The compounds Ib132.1-Ib132.126, which differ from the corresponding compounds Ib1.1-Ib1.126 by the fact that $R^1$ is nitro, $R^2$ is methylsulfonyl, $R^{16}$ is n-butyl and $R^{18}$ is hydrogen.

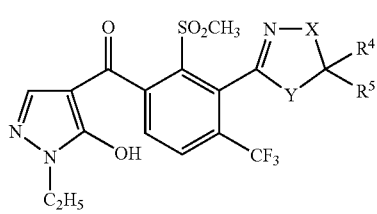
Ib128

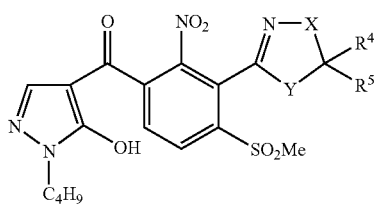
Ib132

The compounds Ib129.1-Ib129.126, which differ from the corresponding compounds Ib1.1-Ib1.126 by the fact that $R^1$ is nitro and $R^2$ is methylsulfonyl.

The compounds Ib133.1-Ib133.126, which differ from the corresponding compounds Ib1.1-Ib1.126 by the fact that $R^1$ is nitro, $R^2$ is methylsulfonyl, $R^{16}$ is iso-butyl and $R^{18}$ is hydrogen.

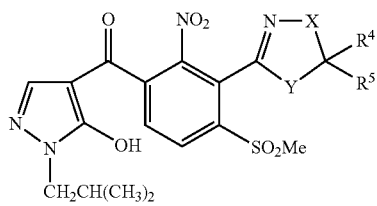
Ib133

The compounds Ib134.1-Ib134.126, which differ from the corresponding compounds Ib1.1-Ib1.126 by the fact that $R^1$ is nitro, $R^2$ is methylsulfonyl, $R^{16}$ is ethyl and $R^{18}$ is hydrogen.

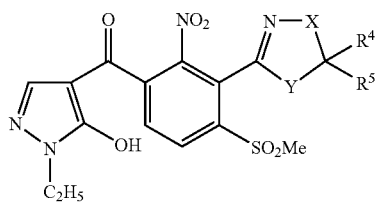
Ib134

The compounds Ib135.1-Ib135.126, which differ from the corresponding compounds Ib1.1-Ib1.126 by the fact that $R^{18}$ is hydrogen.

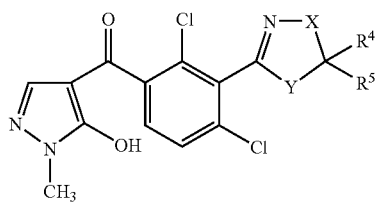
Ib135

The compounds Ib136.1-Ib136.126, which differ from the corresponding compounds Ib1.1-Ib1.126 by the fact that $R^{16}$ is ethyl and $R^{18}$ is hydrogen.

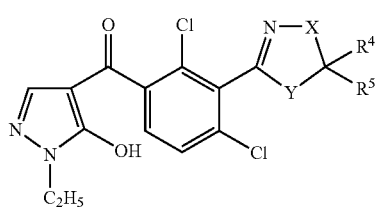
Ib136

The compounds Ib137.1-Ib137.126 which differ from the corresponding compounds Ib1.1-Ib1.126 by the fact that Z is methylsulfonyl and $R^{18}$ is hydrogen.

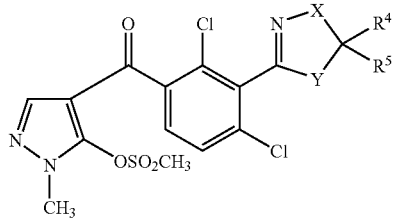
Ib137

The compounds Ib138.1-Ib138.126, which differ from the corresponding compounds Ib1.1-Ib1.126 by the fact that $R^2$ is methylsulfonyl, Z is methylsulfonyl and $R^{18}$ is hydrogen.

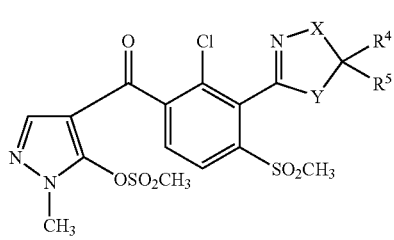
Ib138

The compounds Ib139.1-Ib139.126, which differ from the corresponding compounds Ib1.1-Ib1.126 by the fact that $R^2$ is nitro, Z is methylsulfonyl and $R^{18}$ is hydrogen.

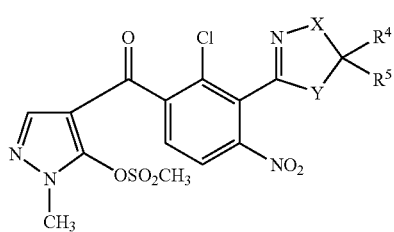
Ib139

The compounds Ib140.1-Ib140.126, which differ from the corresponding compounds Ib1.1-Ib1.126 by the fact that $R^1$ is methyl, $R^2$ is methylsulfonyl, Z is methylsulfonyl and $R^{18}$ is hydrogen.

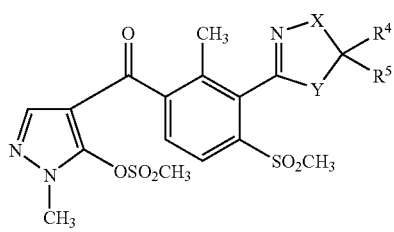
Ib140

The compounds Ib141.1-Ib141.126 which differ from the corresponding compounds Ib1.1-Ib1.126 by the fact that $R^1$ is methylsulfonyl, Z is methylsulfonyl and $R^{18}$ is hydrogen.

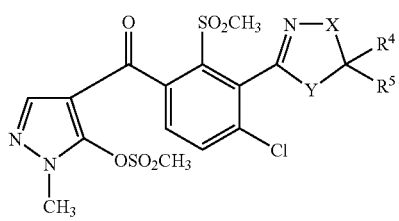

Ib141

The compounds Ib142.1-Ib142.126 which differ from the corresponding compounds Ib1.1-Ib1.126 by the fact that $R^1$ is nitro, Z is methylsulfonyl and $R^{18}$ is hydrogen.

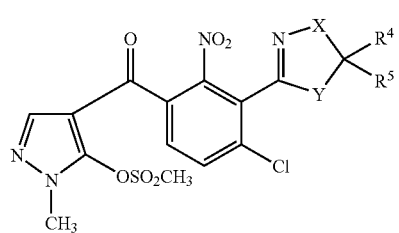

Ib142

The compounds Ib143.1-Ib143.126, which differ from the corresponding compounds Ib1.1-Ib1.126 by the fact $R^1$ is methoxy, $R^2$ and Z are methylsulfonyl and $R^{18}$ is hydrogen.

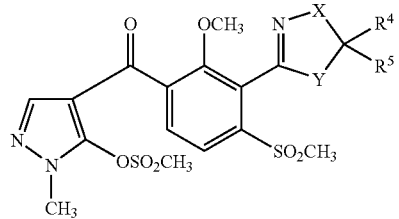

Ib143

The compounds Ib144.1-Ib144.126, which differ from the corresponding compounds Ib1.1-Ib1.126 by the fact that $R^2$ is ethylsulfonyl, Z is methylsulfonyl and $R^{18}$ is hydrogen.

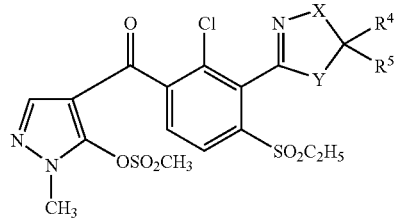

Ib144

The compounds Ib145.1-Ib145.126, which differ from the corresponding compounds Ib1.1-Ib1.126 by the fact that $R^{16}$ is ethyl, Z is methylsulfonyl and $R^{18}$ is hydrogen.

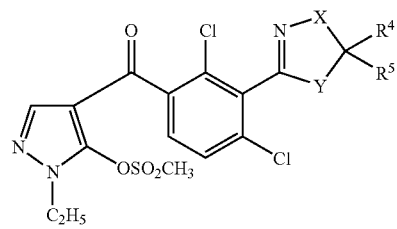

Ib145

The compounds Ib146.1-Ib146.126, which differ from the corresponding compounds Ib1.1-Ib1.126 by the fact that $R^2$ is methylsulfonyl, $R^{16}$ is ethyl, Z is methylsulfonyl and $R^{18}$ is hydrogen.

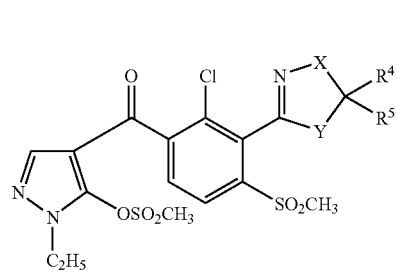

Ib146

The compounds Ib147.1-Ib147.126, which differ from the corresponding compounds Ib1.1-Ib1.126 by the fact that $R^2$ is nitro, $R^{16}$ is ethyl, Z is methylsulfonyl and $R^{18}$ is hydrogen.

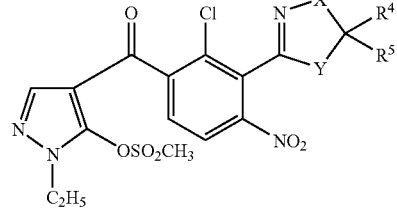

Ib147

The compounds Ib148.1-Ib148.126, which differ from the corresponding compounds Ib1.1-Ib1.126 by the fact that $R^1$ is methyl, $R^2$ is methylsulfonyl, $R^{16}$ is ethyl, Z is methylsulfonyl and $R^{18}$ is hydrogen.

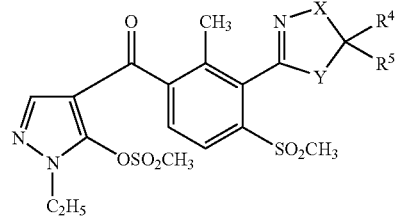

Ib148

The compounds Ib149.1-Ib149.126, which differ from the corresponding compounds Ib1.1-Ib1.126 by the fact that $R^1$ is methylsulfonyl, $R^{16}$ is ethyl, Z is methylsulfonyl and $R^{18}$ is hydrogen.

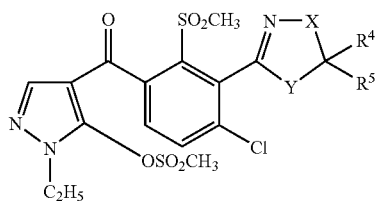

Ib149

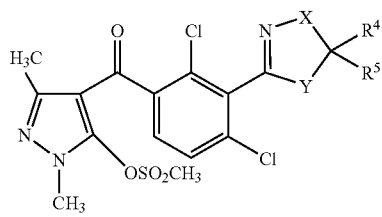

Ib153

The compounds Ib150.1-Ib150.126, which differ from the corresponding compounds Ib1.1-Ib1.126 by the fact that $R^1$ is nitro, $R^{16}$ is ethyl, Z is methylsulfonyl and $R^{18}$ is hydrogen.

The compounds Ib154.1-Ib154.126, which differ from the corresponding compounds Ib1.1-Ib1.126 by the fact that $R^2$ and Z are methylsulfonyl.

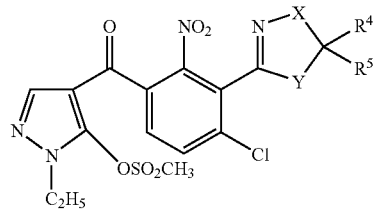

Ib150

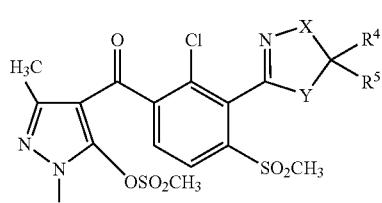

Ib154

The compounds Ib151.1-Ib151.126, which differ from the corresponding compounds Ib1.1-Ib1.126 by the fact that $R^1$ is methoxy, $R^2$ is methylsulfonyl, $R^{16}$ is ethyl, Z is methylsulfonyl and $R^{18}$ is hydrogen.

The compounds Ib155.1-Ib155.126, which differ from the corresponding compounds Ib1.1-Ib1.126 by the fact that $R^2$ is nitro and Z is methylsulfonyl.

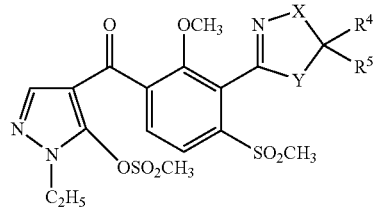

Ib151

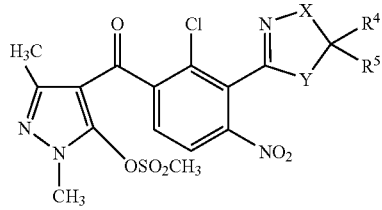

Ib155

The compounds Ib152.1-Ib152.126, which differ from the corresponding compounds Ib1.1-Ib1.126 by the fact that $R^2$ is ethylsulfonyl, $R^{16}$ is ethyl, Z is methylsulfonyl and $R^{18}$ is hydrogen.

The compounds Ib156.1-Ib156.126, which differ from the corresponding compounds Ib1.1-Ib1.126 by the fact that $R^1$ is methyl, $R^2$ and Z are methylsulfonyl.

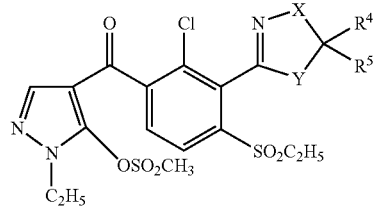

Ib152

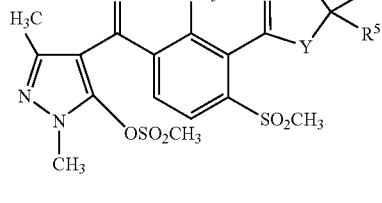

Ib156

The compounds Ib153.1-Ib153.126, which differ from the corresponding compounds Ib1.1-Ib1.126 by the fact that Z is methylsulfonyl.

The compounds Ib157.1-Ib157.126, which differ from the corresponding compounds Ib1.1-Ib1.126 by the fact that $R^1$ and Z are methylsulfonyl.

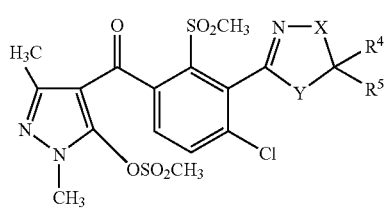
Ib157

The compounds Ib158.1-Ib158.126, which differ from the corresponding compounds Ib1.1-Ib1.126 by the fact that $R^1$ is nitro and Z is methylsulfonyl.

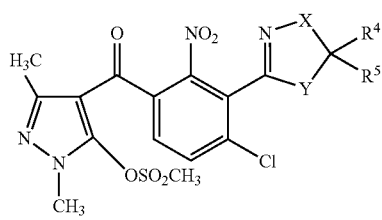
Ib158

The compounds Ib159.1-Ib159.126, which differ from the corresponding compounds Ib1.1-Ib1.126 by the fact that $R^1$ is methoxy, $R^2$ and Z are methylsulfonyl.

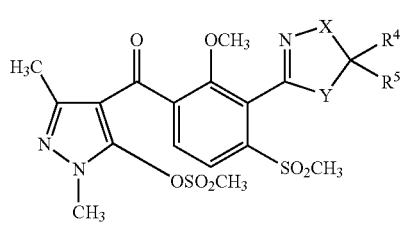
Ib159

The compounds Ib160.1-Ib160.126, which differ from the corresponding compounds Ib1.1-Ib1.126 by the fact that $R^2$ is ethylsulfonyl and Z is methylsulfonyl.

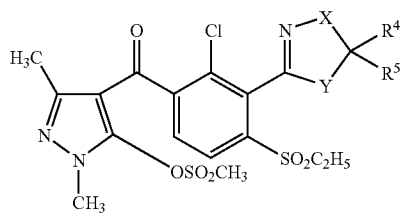
Ib160

The compounds Ib161.1-Ib161.126, which differ from the corresponding compounds Ib1.1-Ib1.126 by the fact that Z is ethylsulfonyl and $R^{18}$ is hydrogen.

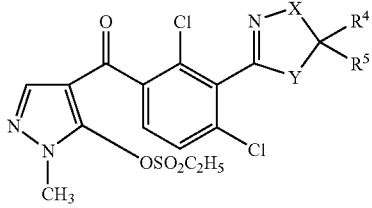
Ib161

The compounds Ib162.1-Ib162.126, which differ from the corresponding compounds Ib1.1-Ib1.126 by the fact that $R^2$ is methylsulfonyl, Z is ethylsulfonyl and $R^{18}$ is hydrogen.

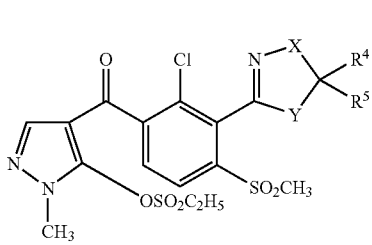
Ib162

The compounds Ib163.1-Ib163.126, which differ from the corresponding compounds Ib1.1-Ib1.126 by the fact that $R^2$ is nitro, Z is ethylsulfonyl and $R^{18}$ is hydrogen.

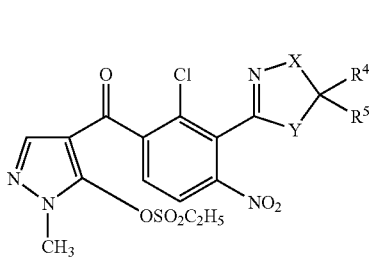
Ib163

The compounds Ib164.1-Ib164.126, which differ from the corresponding compounds Ib1.1-Ib1.126 by the fact that $R^1$ is methyl, $R^2$ is methylsulfonyl, Z is ethylsulfonyl and $R^{18}$ is hydrogen.

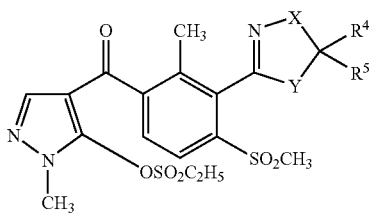
Ib164

The compounds Ib165.1-Ib165.126, which differ from the corresponding compounds Ib1.1-Ib1.126 by the fact that $R^1$ is methylsulfonyl, Z is ethylsulfonyl and $R^{18}$ is hydrogen.

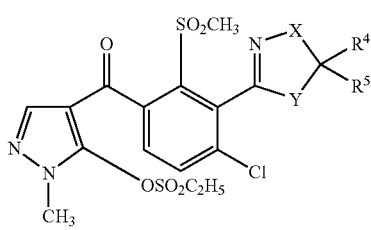

Ib165

The compounds Ib166.1-Ib166.126, which differ from the corresponding compounds Ib1.1-Ib1.126 by the fact that $R^1$ is nitro, Z is ethylsulfonyl and $R^{18}$ is hydrogen.

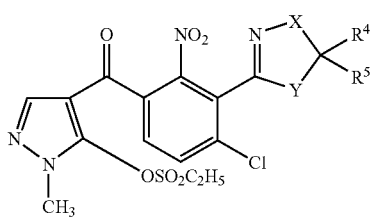

Ib166

The compounds Ib167.1-Ib167.126, which differ from the corresponding compounds Ib1.1-Ib1.126 by the fact that $R^1$ is methoxy, $R^2$ is methylsulfonyl, Z is ethylsulfonyl and $R^{18}$ is hydrogen.

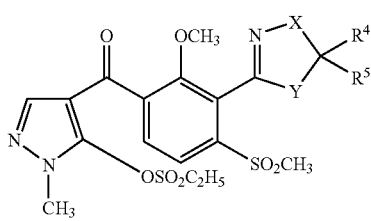

Ib167

The compounds Ib168.1-Ib168.126, which differ from the corresponding compounds Ib1.1-Ib1.126 by the fact that $R^2$ and Z are ethylsulfonyl and $R^{18}$ is hydrogen.

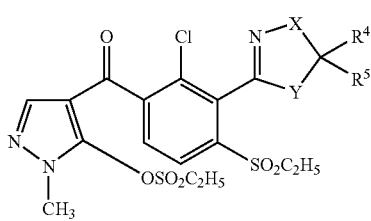

Ib168

The compounds Ib169.1-Ib169.126, which differ from the corresponding compounds Ib1.1-Ib1.126 by the fact that $R^{16}$ is ethyl, Z is ethylsulfonyl and $R^{18}$ is hydrogen.

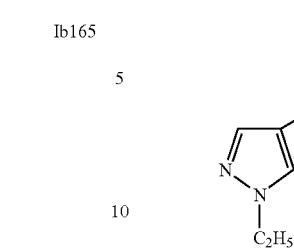

Ib169

The compounds Ib170.1-Ib170.126, which differ from the corresponding compounds Ib1.1-Ib1.126 by the fact that $R^2$ is methylsulfonyl, $R^{16}$ is ethyl, Z is ethylsulfonyl and $R^{18}$ is hydrogen.

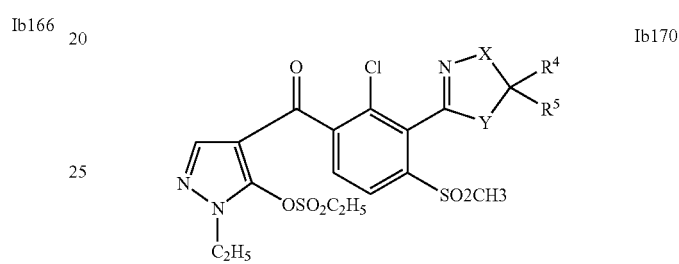

Ib170

The compounds Ib171.1-Ib171.126, which differ from the corresponding compounds Ib1.1-Ib1.126 by the fact that $R^2$ is nitro, $R^{16}$ is ethyl, Z is ethylsulfonyl and $R^{18}$ is hydrogen.

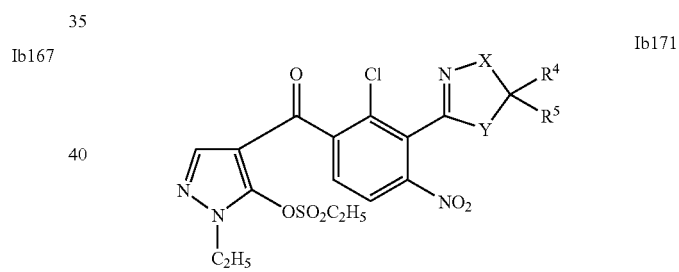

Ib171

The compounds Ib172.1-Ib172.126, which differ from the corresponding compounds Ib1.1-Ib1.126 by the fact that $R^1$ is methyl, $R^2$ is methylsulfonyl, $R^{16}$ is ethyl, Z is ethylsulfonyl and $R^{18}$ is hydrogen.

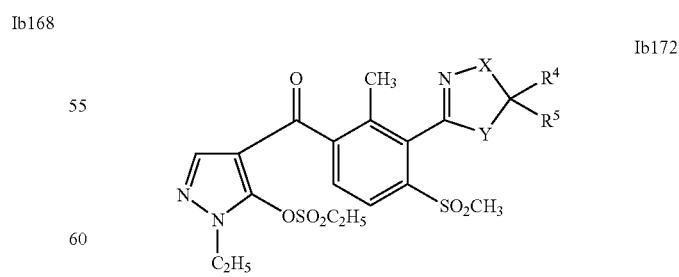

Ib172

The compounds Ib173.1-Ib173.126, which differ from the corresponding compounds Ib1.1-Ib1.126 by the fact that $R^1$ is methylsulfonyl, $R^{16}$ is ethyl, Z is ethylsulfonyl and $R^{18}$ is hydrogen.

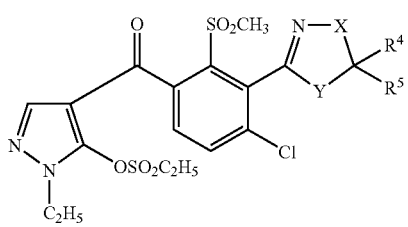
Ib173

The compounds Ib174.1-Ib174.126, which differ from the corresponding compounds Ib1.1-Ib1.126 by the fact that $R^1$ is nitro, $R^{16}$ is ethyl, Z is ethylsulfonyl and $R^{18}$ is hydrogen.

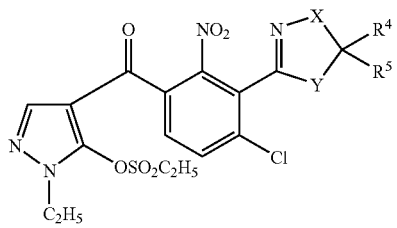
Ib174

The compounds Ib175.1-Ib175.126, which differ from the corresponding compounds Ib1.1-Ib1.126 by the fact that $R^1$ is methoxy, $R^2$ is methylsulfonyl, $R^{16}$ is ethyl, Z is ethylsulfonyl and $R^{18}$ is hydrogen.

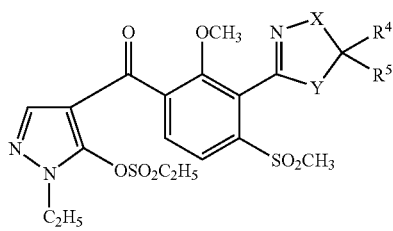
Ib175

The compounds Ib176.1-Ib176.126, which differ from the corresponding compounds Ib1.1-Ib1.126 by the fact that $R^2$ is ethylsulfonyl, $R^{16}$ is ethyl, Z is ethylsulfonyl and $R^{18}$ is hydrogen.

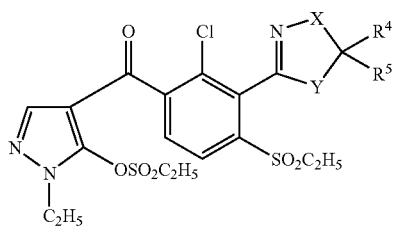
Ib176

The compounds Ib177.1-Ib177.126, which differ from the corresponding compounds Ib1.1-Ib1.126 by the fact that Z is ethylsulfonyl.

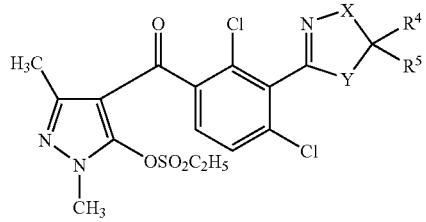
Ib177

The compounds Ib178.1-Ib178.126, which differ from the corresponding compounds Ib1.1-Ib1.126 by the fact that $R^2$ is methylsulfonyl and Z is ethylsulfonyl.

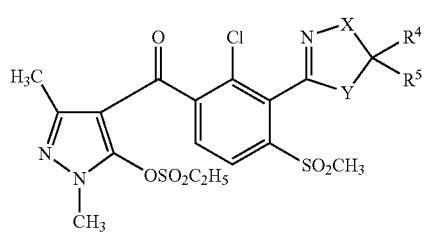
Ib178

The compounds Ib179.1-Ib179.126, which differ from the corresponding compounds Ib1.1-Ib1.126 by the fact that $R^2$ is nitro and Z is ethylsulfonyl.

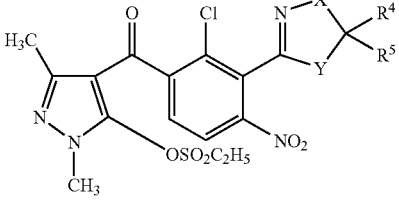
Ib179

The compounds Ib180.1-Ib180.126, which differ from the corresponding compounds Ib1.1-Ib1.126 by the fact that $R^1$ is methyl, $R^2$ is methylsulfonyl and Z is ethylsulfonyl.

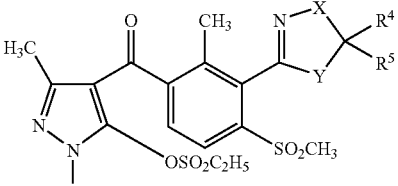
Ib180

The compounds Ib181.1-Ib181.126, which differ from the corresponding compounds Ib1.1-Ib1.126 by the fact that $R^1$ is methylsulfonyl and Z is ethylsulfonyl.

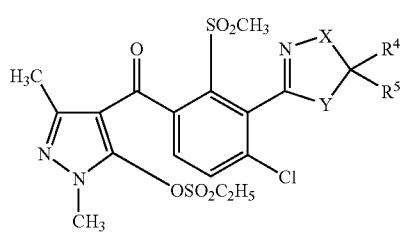
Ib181

The compounds Ib182.1-Ib182.126, which differ from the corresponding compounds Ib1.1-Ib1.126 by the fact that R¹ is nitro and Z is ethylsulfonyl.

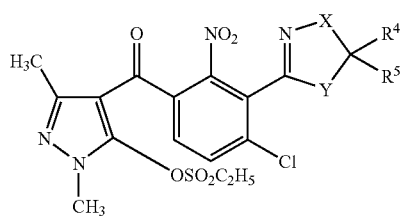
Ib182

The compounds Ib183.1-Ib183.126, which differ from the corresponding compounds Ib1.1-Ib1.126 by the fact that R¹ is methoxy, R² is methylsulfonyl and Z is ethylsulfonyl.

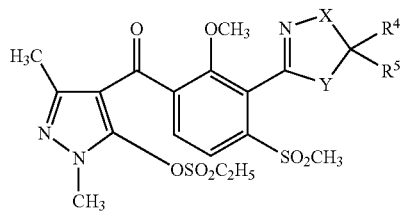
Ib183

The compounds Ib184.1-Ib184.126, which differ from the corresponding compounds Ib1.1-Ib1.126 by the fact that R² and Z are ethylsulfonyl.

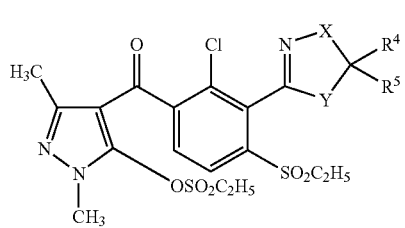
Ib184

The compounds Ib185.1-Ib185.126 which differ from the corresponding compounds Ib1.1-Ib1.126 by the fact that Z is iso-propylsulfonyl and $R^{18}$ is hydrogen.

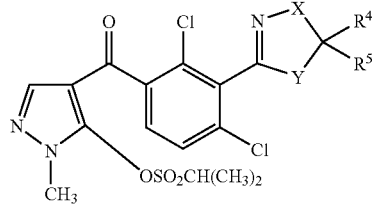
Ib185

The compounds Ib186.1-Ib186.126, which differ from the corresponding compounds Ib1.1-Ib1.126 by the fact that R² is methylsulfonyl, Z is iso-propylsulfonyl and $R^{18}$ is hydrogen.

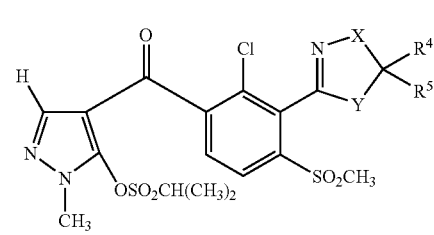
Ib186

The compounds Ib187.1-Ib187.126, which differ from the corresponding compounds Ib1.1-Ib1.126 by the fact that R² is nitro, Z is iso-propylsulfonyl and $R^{18}$ is hydrogen.

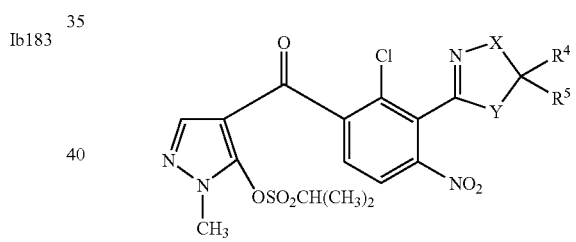
Ib187

The compounds Ib188.1-Ib188.126, which differ from the corresponding compounds Ib1.1-Ib1.126 by the fact that R¹ is methyl, R² is methylsulfonyl, Z is iso-propylsulfonyl and $R^{18}$ is hydrogen.

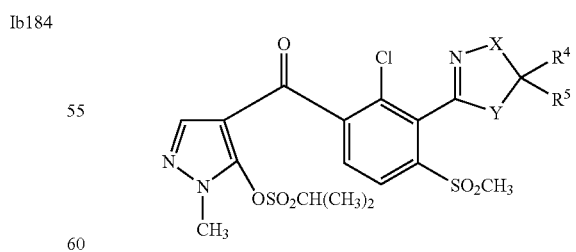
Ib188

The compounds Ib189.1-Ib189.126, which differ from the corresponding compounds Ib1.1-Ib1.126 by the fact that R¹ is methylsulfonyl, Z is iso-propylsulfonyl and $R^{18}$ is hydrogen.

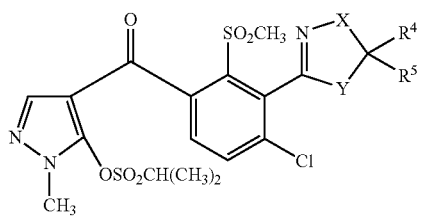

Ib189

The compounds Ib190.1-Ib190.126, which differ from the corresponding compounds Ib1.1-Ib1.126 by the fact that $R^1$ is nitro, Z is iso-propylsulfonyl and $R^{18}$ is hydrogen.

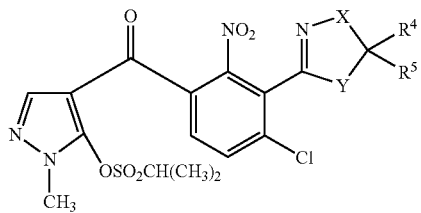

Ib190

The compounds Ib191.1-Ib191.126, which differ from the corresponding compounds Ib1.1-Ib1.126 by the fact that $R^1$ is methoxy, $R^2$ is methylsulfonyl, Z is iso-propylsulfonyl and $R^{18}$ is hydrogen.

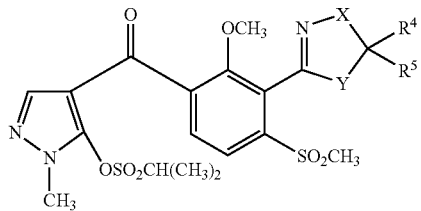

Ib191

The compounds Ib192.1-Ib192.126, which differ from the corresponding compounds Ib1.1-Ib1.126 by the fact that $R^2$ is ethylsulfonyl, Z is isopropylsulfonyl and $R^{18}$ is hydrogen.

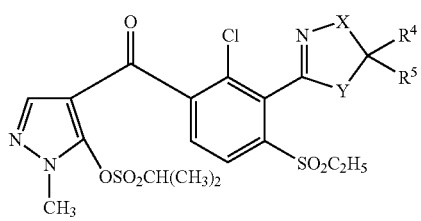

Ib192

The compounds Ib193.1-Ib193.126, which differ from the corresponding compounds Ib1.1-Ib1.126 by the fact that $R^{16}$ is ethyl, Z is iso-propylsulfonyl and $R^{18}$ is hydrogen.

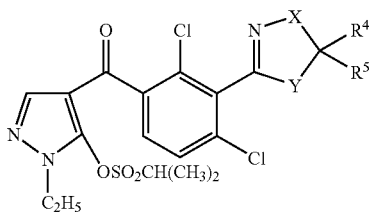

Ib193

The compounds Ib194.1-Ib194.126, which differ from the corresponding compounds Ib1.1-Ib1.126 by the fact that $R^2$ is methylsulfonyl, $R^{16}$ is ethyl, Z is iso-propylsulfonyl and $R^{18}$ is hydrogen.

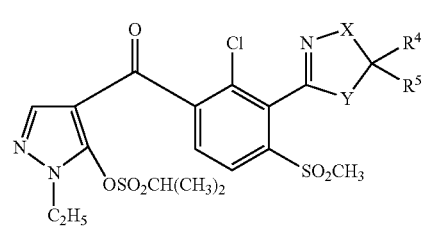

Ib194

The compounds Ib195.1-Ib195.126, which differ from the corresponding compounds Ib1.1-Ib1.126 by the fact that $R^2$ is nitro, $R^{16}$ is ethyl, Z is iso-propylsulfonyl and $R^{18}$ is hydrogen.

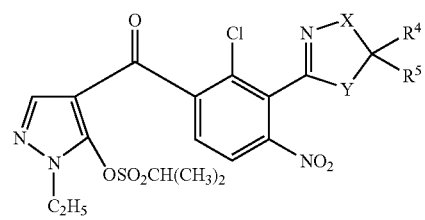

Ib195

The compounds Ib196.1-Ib196.126, which differ from the corresponding compounds Ib1.1-Ib1.126 by the fact that $R^1$ is methyl, $R^2$ is methylsulfonyl, $R^{16}$ is ethyl, Z is iso-propylsulfonyl and $R^{18}$ is hydrogen.

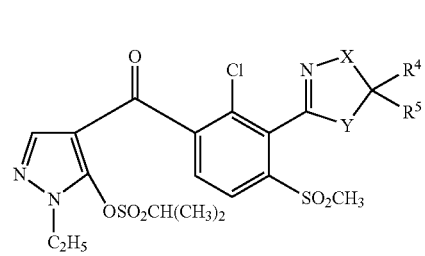

Ib196

The compounds Ib197.1-Ib197.126, which differ from the corresponding compounds Ib1.1-Ib1.126 by the fact that $R^1$ is methylsulfonyl, $R^{16}$ is ethyl, Z is iso-propylsulfonyl and $R^{18}$ is hydrogen.

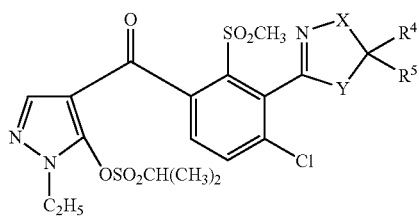
Ib197

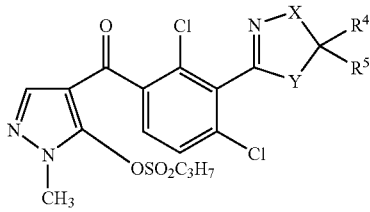
Ib201

The compounds Ib198.1-Ib198.126, which differ from the corresponding compounds Ib1.1-Ib1.126 by the fact that $R^1$ is nitro, $R^{16}$ is ethyl, Z is iso-propylsulfonyl and $R^{18}$ is hydrogen.

The compounds Ib202.1-Ib202.126, which differ from the corresponding compounds Ib1.1-Ib1.126 by the fact that $R^2$ is methylsulfonyl, Z is n-propylsulfonyl and $R^{18}$ is hydrogen.

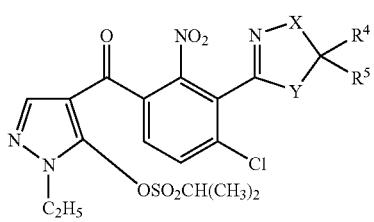
Ib198

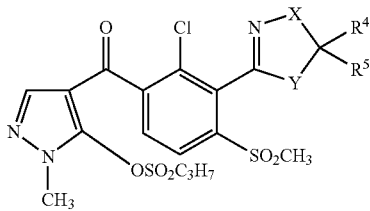
Ib202

The compounds Ib199.1-Ib199.126, which differ from the corresponding compounds Ib1.1-Ib1.126 by the fact that $R^1$ is methoxy, $R^2$ is methylsulfonyl, $R^{16}$ is ethyl, Z is iso-propylsulfonyl and $R^{18}$ is hydrogen.

The compounds Ib203.1-Ib203.126, which differ from the corresponding compounds Ib1.1-Ib1.126 by the fact that $R^2$ is nitro, Z is n-propylsulfonyl and $R^{18}$ is hydrogen.

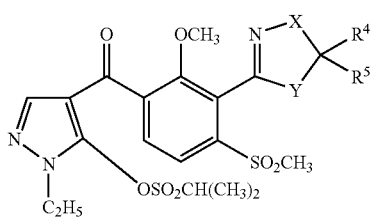
Ib199

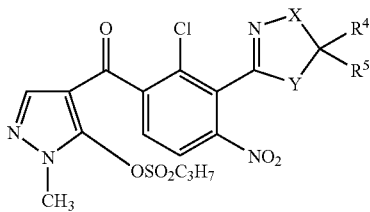
Ib203

The compounds Ib200.1-Ib200.126, which differ from the corresponding compounds Ib1.1-Ib1.126 by the fact that $R^2$ is ethylsulfonyl, $R^{16}$ is ethyl, Z is iso-propylsulfonyl and $R^{18}$ is hydrogen.

The compounds Ib204.1-Ib204.126, which differ from the corresponding compounds Ib1.1-Ib1.126 by the fact that $R^1$ is methyl, $R^2$ is methylsulfonyl, Z is n-propylsulfonyl and $R^{18}$ is hydrogen.

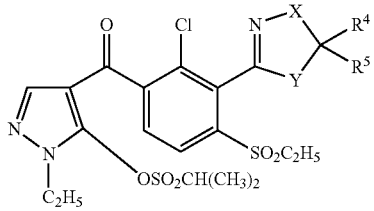
Ib200

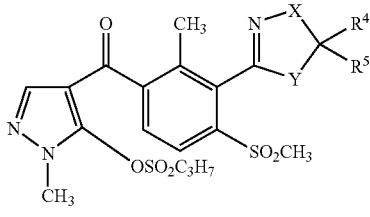
Ib204

The compounds Ib201.1-Ib201.126, which differ from the corresponding compounds Ib1.1-Ib1.126 by the fact that Z is n-propylsulfonyl and $R^{18}$ is hydrogen.

The compounds Ib205.1-Ib205.126, which differ from the corresponding compounds Ib1.1-Ib1.126 by the fact that $R^1$ is methylsulfonyl, Z is n-propylsulfonyl and $R^{18}$ is hydrogen.

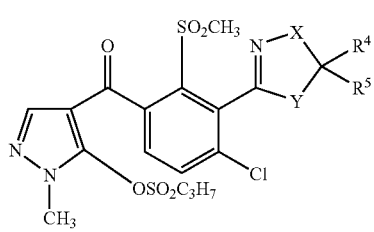

Ib205

The compounds Ib206.1-Ib206.126, which differ from the corresponding compounds Ib1.1-Ib1.126 by the fact that $R^1$ is nitro, Z is n-propylsulfonyl and $R^{18}$ is hydrogen.

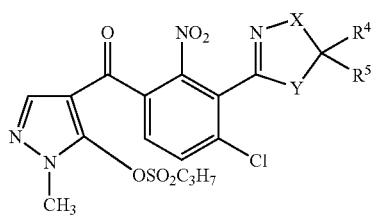

Ib206

The compounds Ib207.1-Ib207.126, which differ from the corresponding compounds Ib1.1-Ib1.126 by the fact that $R^1$ is methoxy, $R^2$ is methylsulfonyl, Z is n-propylsulfonyl and $R^{18}$ is hydrogen.

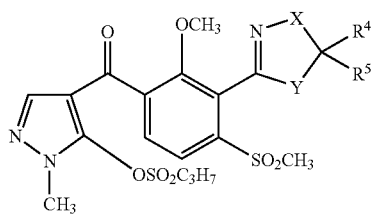

Ib207

The compounds Ib.208.1-Ib208.126, which differ from the corresponding compounds Ib1.1-Ib1.126 by the fact that $R^2$ is ethylsulfonyl, Z is n-propylsulfonyl and $R^{18}$ is hydrogen.

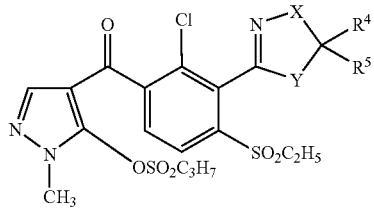

Ib208

The compounds Ib209.1-Ib209.126, which differ from the corresponding compounds Ib1.1-Ib1.126 by the fact that $R^{16}$ is ethyl, Z is n-propylsulfonyl and $R^{18}$ is hydrogen.

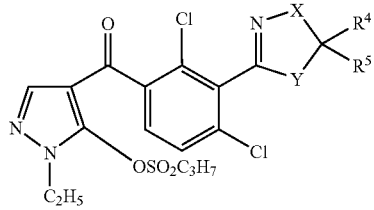

Ib209

The compounds Ib210.1-Ib210.126, which differ from the corresponding compounds Ib1.1-Ib1.126 by the fact that $R^2$ is methylsulfonyl, $R^{16}$ is ethyl, Z is n-propylsulfonyl and $R^{18}$ is hydrogen.

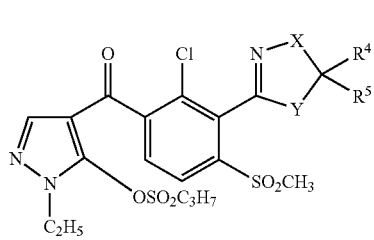

Ib210

The compounds Ib211.1-211.126, which differ from the corresponding compounds Ib1.1-Ib1.126 by the fact that $R^2$ is nitro, $R^{16}$ is ethyl, Z is n-propylsulfonyl and $R^{18}$ is hydrogen.

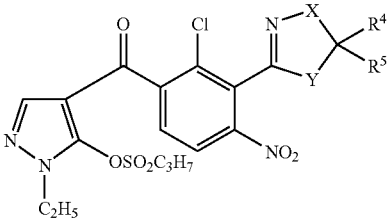

Ib211

The compounds Ib212.1-Ib212.126, which differ from the corresponding compounds Ib1.1-Ib1.126 by the fact that $R^1$ is methyl, $R^2$ is methylsulfonyl, $R^{16}$ is ethyl, Z is n-propylsulfonyl and $R^{18}$ is hydrogen.

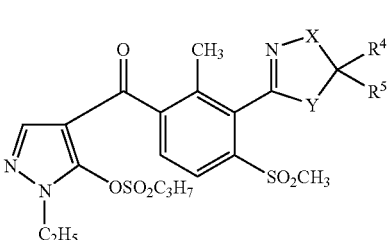

Ib212

The compounds Ib213.1-Ib213.126, which differ from the corresponding compounds Ib1.1-Ib1.126 by the fact that $R^1$ is methylsulfonyl, $R^{16}$ is ethyl, Z is n-propylsulfonyl and $R^{18}$ is hydrogen.

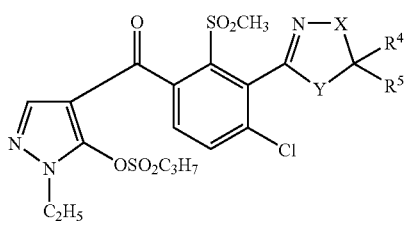
Ib213

The compounds Ib214.1-Ib214.126, which differ from the corresponding compounds Ib1.1-Ib1.126 by the fact that $R^1$ is nitro, $R^{16}$ is ethyl, Z is n-propylsulfonyl and $R^{18}$ is hydrogen.

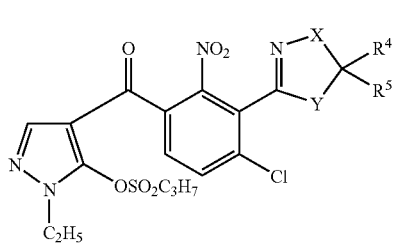
Ib214

The compounds Ib215.1-Ib215.126, which differ from the corresponding compounds Ib1.1-Ib1.126 by the fact that $R^1$ is methoxy, $R^2$ is methylsulfonyl, $R^{16}$ is ethyl, Z is n-propylsulfonyl and $R^{18}$ is hydrogen.

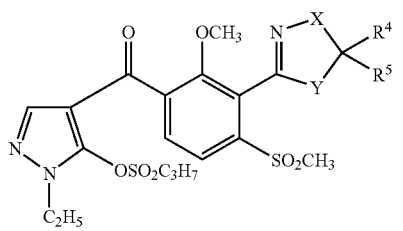
Ib215

The compounds Ib216.1-Ib216.126, which differ from the corresponding compounds Ib1.1-Ib1.126 by the fact that $R^2$ is ethylsulfonyl, $R^{16}$ is ethyl, Z is n-propylsulfonyl and $R^{18}$ is hydrogen.

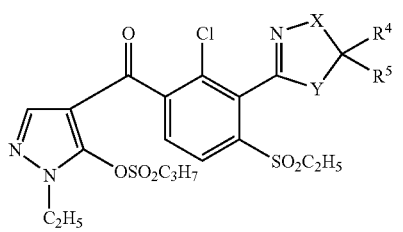
Ib216

The compounds Ib217.1-Ib217.126, which differ from the corresponding compounds Ib1.1-Ib1.126 by the fact that Z is n-butylsulfonyl and $R^{18}$ is hydrogen.

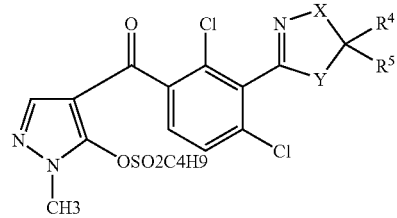
Ib217

The compounds Ib218.1-Ib218.126, which differ from the corresponding compounds Ib1.1-Ib1.126 by the fact that $R^2$ is methylsulfonyl, Z is n-butylsulfonyl and $R^{18}$ is hydrogen.

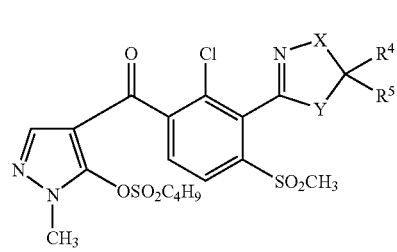
Ib218

The compounds Ib219.1-Ib219.126, which differ from the corresponding compounds Ib1.1-Ib1.126 by the fact that $R^2$ is nitro, Z is n-butylsulfonyl and $R^{18}$ is hydrogen.

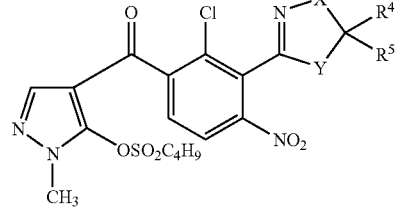
Ib219

The compounds Ib220.1-Ib220.126, which differ from the corresponding compounds Ib1.1-Ib1.126 by the fact that $R^1$ is methyl, $R^2$ is methylsulfonyl, Z is n-butylsulfonyl and $R^{18}$ is hydrogen.

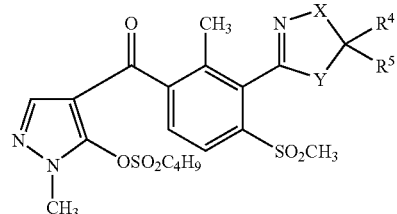
Ib220

The compounds Ib221.1-Ib221.126, which differ from the corresponding compounds Ib1.1-Ib1.126 by the fact that $R^1$ is methylsulfonyl, Z is n-butylsulfonyl and $R^{18}$ is hydrogen.

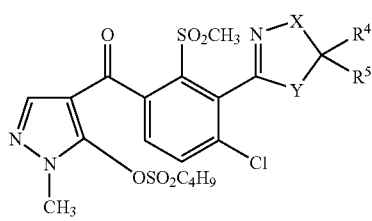

Ib221

The compounds Ib222.1-Ib222.126, which differ from the corresponding compounds Ib1.1-Ib1.126 by the fact that $R^1$ is nitro, Z is n-butylsulfonyl and $R^{18}$ is hydrogen.

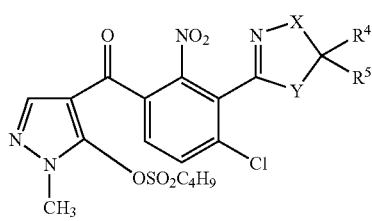

Ib222

The compounds Ib223.1-Ib223.126, which differ from the corresponding compounds Ib1.1-Ib1.126 by the fact that $R^1$ is methoxy, $R^2$ is methylsulfonyl, Z is n-butylsulfonyl and $R^{18}$ is hydrogen.

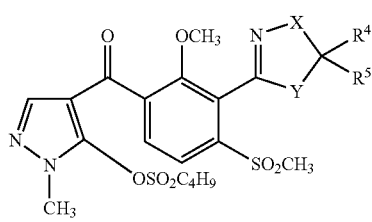

Ib223

The compounds Ib224.1-Ib224.126, which differ from the corresponding compounds Ib1.1-Ib1.126 by the fact that $R^2$ is ethylsulfonyl, Z is n-butylsulfonyl and $R^{18}$ is hydrogen.

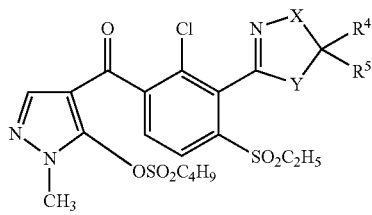

Ib224

The compounds Ib225.1-Ib225.126, which differ from the corresponding compounds Ib1.1-Ib1.126 by the fact that $R^{16}$ is ethyl, Z is n-butylsulfonyl and $R^{18}$ is hydrogen.

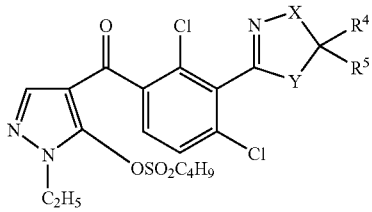

Ib225

The compounds Ib226.1-Ib226.126, which differ from the corresponding compounds Ib1.1-Ib1.126 by the fact that $R^2$ is methylsulfonyl, $R^{16}$ is ethyl, Z is n-butylsulfonyl and $R^{18}$ is hydrogen.

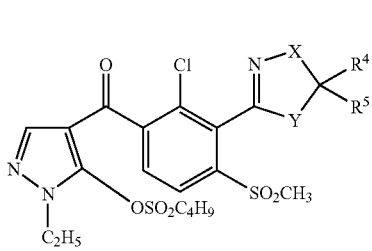

Ib226

The compounds Ib227.1-Ib227.126, which differ from the corresponding compounds Ib1.1-Ib1.126 by the fact that $R^2$ is nitro, $R^{16}$ is ethyl, Z is n-butylsulfonyl and $R^{18}$ is hydrogen.

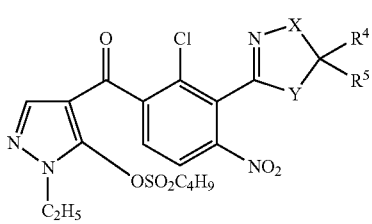

Ib227

The compounds Ib228.1-Ib228.126, which differ from the corresponding compounds Ib1.1-Ib1.126 by the fact that $R^1$ is methyl, $R^2$ is methylsulfonyl, $R^{16}$ is ethyl, Z is n-butylsulfonyl and $R^{18}$ is hydrogen.

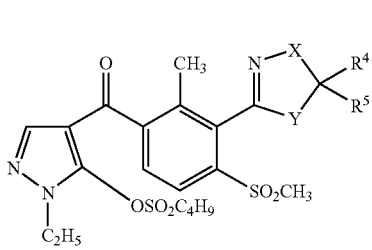

Ib228

The compounds Ib229.1-Ib229.126, which differ from the corresponding compounds Ib1.1-Ib1.126 by the fact that $R^1$ is methylsulfonyl, $R^{16}$ is ethyl, Z is n-butylsulfonyl and $R^{18}$ is hydrogen.

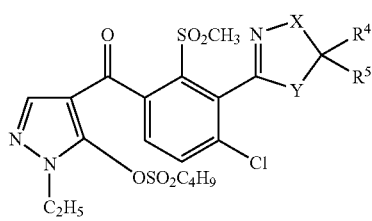

Ib229

The compounds Ib230.1-Ib230.126, which differ from the corresponding compounds Ib1.1-Ib1.126 by the fact that $R^1$ is nitro, $R^{16}$ is ethyl, Z is n-butylsulfonyl and $R^{18}$ is hydrogen.

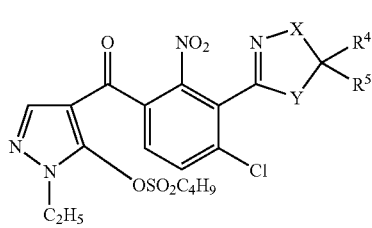

Ib230

The compounds Ib231.1-Ib231.126, which differ from the corresponding compounds Ib1.1-Ib1.126 by the fact that $R^1$ is methoxy, $R^2$ is methylsulfonyl, $R^{16}$ is ethyl, Z is n-butylsulfonyl and $R^{18}$ is hydrogen.

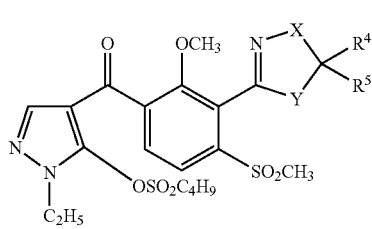

Ib231

The compounds Ib232.1-Ib232.126, which differ from the corresponding compounds Ib1.1-Ib1.126 by the fact that $R^2$ is ethylsulfonyl, $R^{16}$ is ethyl, Z is n-butylsulfonyl and $R^{18}$ is hydrogen.

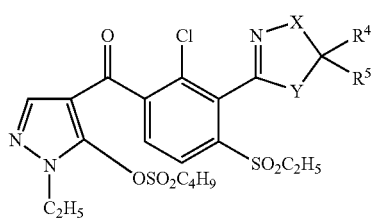

Ib232

The compounds Ib233.1-Ib233.126, which differ from the corresponding compounds Ib1.1-Ib1.126 by the fact that Z is iso-butylsulfonyl and $R^{18}$ is hydrogen.

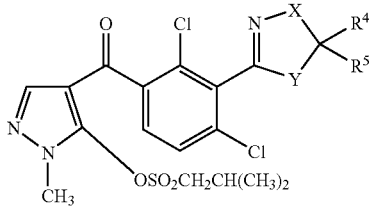

Ib233

The compounds Ib234.1-Ib234.126, which differ from the corresponding compounds Ib1.1-Ib1.126 by the fact that $R^2$ is methylsulfonyl, Z is iso-butylsulfonyl and $R^{18}$ is hydrogen.

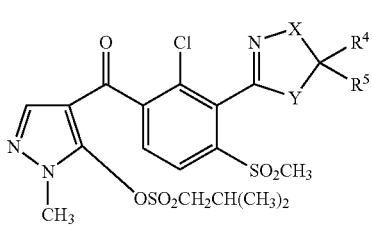

Ib234

The compounds Ib235.1-Ib235.126, which differ from the corresponding compounds Ib1.1-Ib1.126 by the fact that $R^2$ is nitro, Z is iso-butylsulfonyl and $R^{18}$ is hydrogen.

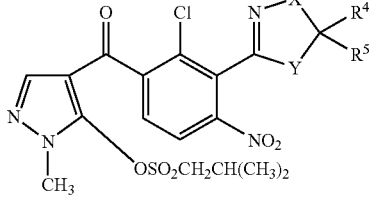

Ib235

The compounds Ib236.1-Ib236.126, which differ from the corresponding compounds Ib1.1-Ib1.126 by the fact that $R^1$ is methyl, $R^2$ is methylsulfonyl, Z is iso-butylsulfonyl and $R^{18}$ is hydrogen.

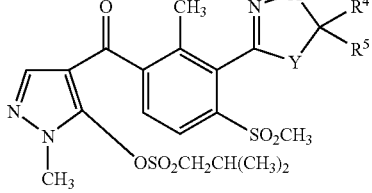

Ib236

The compounds Ib237.1-Ib237.126, which differ from the corresponding compounds Ib1.1-Ib1.126 by the fact that $R^1$ is methylsulfonyl, Z is iso-butylsulfonyl and $R^{18}$ is hydrogen.

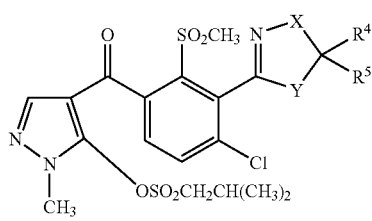

Ib237

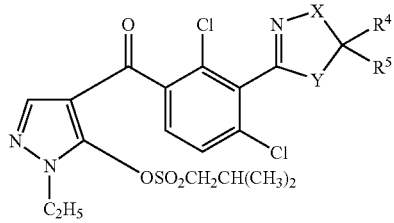

Ib241

The compounds Ib238.1-Ib238.126, which differ from the corresponding compounds Ib1.1-Ib1.126 by the fact that $R^1$ is nitro, Z is iso-butylsulfonyl and $R^{18}$ is hydrogen.

The compounds Ib242.1-Ib242.126, which differ from the corresponding compounds Ib1.1-Ib1.126 by the fact that $R^2$ is methylsulfonyl, $R^{16}$ is ethyl, Z is iso-butylsulfonyl and $R^{18}$ is hydrogen.

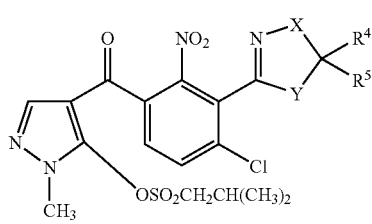

Ib238

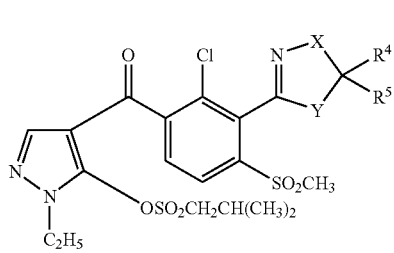

Ib242

The compounds Ib239.1-Ib239.126, which differ from the corresponding compounds Ib1.1-Ib1.126 by the fact that $R^1$ is methoxy, $R^2$ is methylsulfonyl, Z is iso-butylsulfonyl and $R^{18}$ is hydrogen.

The compounds Ib243.1-Ib243.126, which differ from the corresponding compounds Ib1.1-Ib1.126 by the fact that $R^2$ is nitro, $R^{16}$ is ethyl, Z is iso-butylsulfonyl and $R^{18}$ is hydrogen.

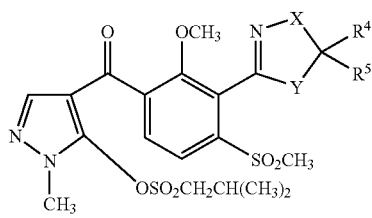

Ib239

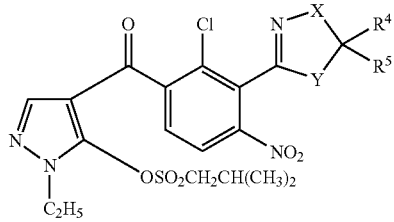

Ib243

The compounds Ib240.1-Ib240.126, which differ from the corresponding compounds Ib1.1-Ib1.126 by the fact that $R^2$ is ethylsulfonyl, Z is iso-butylsulfonyl and $R^{18}$ is hydrogen.

The compounds Ib244.1-Ib244.126, which differ from the corresponding compounds Ib1.1-Ib1.126 by the fact that $R^1$ is methyl, $R^2$ is methylsulfonyl, $R^{16}$ is ethyl, Z is iso-butylsulfonyl and $R^{18}$ is hydrogen.

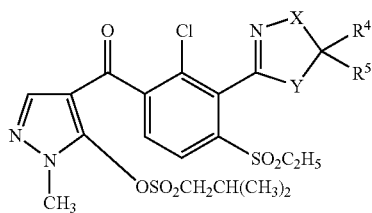

Ib240

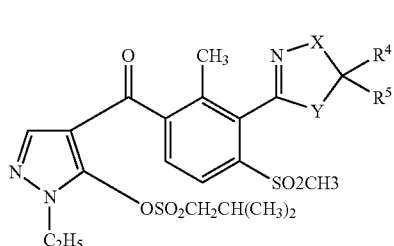

Ib244

The compounds Ib241.1-Ib241.126, which differ from the corresponding compounds Ib1.1-Ib1.126 by the fact that $R^{16}$ is ethyl, Z is iso-butylsulfonyl and $R^{18}$ is hydrogen.

The compounds Ib245.1-Ib245.126, which differ from the corresponding compounds Ib1.1-Ib1.126 by the fact that $R^1$ is methylsulfonyl, $R^{16}$ is ethyl, Z is iso-butylsulfonyl and $R^{18}$ is hydrogen.

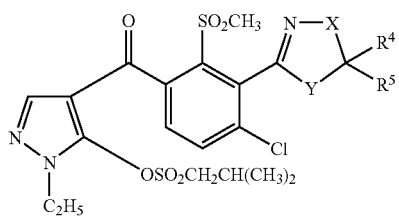
Ib245

The compounds Ib246.1-Ib246.126, which differ from the corresponding compounds Ib1.1-Ib1.126 by the fact that $R^1$ is nitro, $R^{16}$ is ethyl, Z is iso-butylsulfonyl and $R^{18}$ is hydrogen.

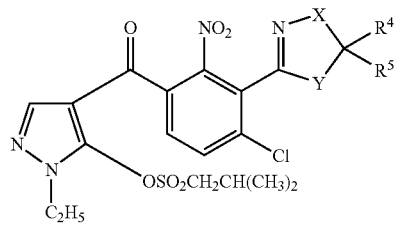
Ib246

The compounds Ib247.1-Ib247.126, which differ from the corresponding compounds Ib1.1-Ib1.126 by the fact that $R^1$ is methoxy, $R^2$ is methylsulfonyl, $R^{16}$ is ethyl, Z is iso-butylsulfonyl and $R^{18}$ is hydrogen.

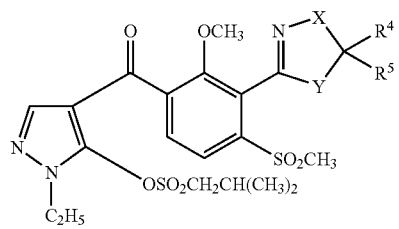
Ib247

The compounds Ib248.1-Ib248.126, which differ from the corresponding compounds Ib1.1-Ib1.126 by the fact that $R^2$ is methylsulfonyl, $R^{16}$ is ethyl, Z is iso-butylsulfonyl and $R^{18}$ is hydrogen.

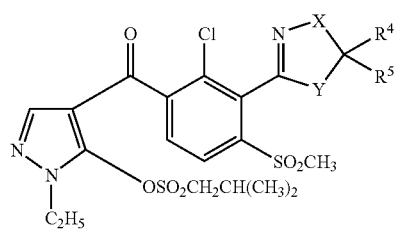
Ib248

The compounds Ib249.1-Ib249.126, which differ from the corresponding compounds Ib1.1-Ib1.126 by the fact that Z is phenylsulfonyl and $R^{18}$ is hydrogen.

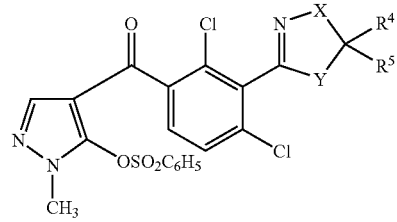
Ib249

The compounds Ib250.1-Ib250.126, which differ from the corresponding compounds Ib1.1-Ib1.126 by the fact that $R^2$ is methylsulfonyl, Z is phenylsulfonyl and $R^{18}$ is hydrogen.

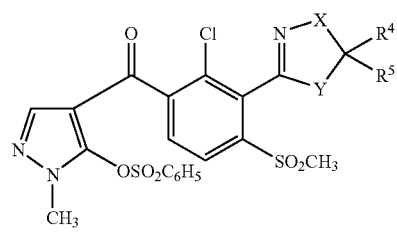
Ib250

The compounds Ib251.1-Ib251.126 which differ from the corresponding compounds Ib1.1-Ib1.126 by the fact that $R^1$ is methyl, $R^2$ is methylsulfonyl, Z is phenylsulfonyl and $R^{18}$ is hydrogen.

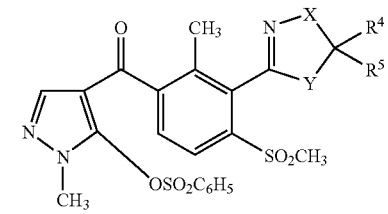
Ib251

The compounds Ib252.1-Ib252.126, which differ from the corresponding compounds Ib1.1-Ib1.126 by the fact that $R^2$ is ethylsulfonyl, Z is phenylsulfonyl and $R^{18}$ is hydrogen.

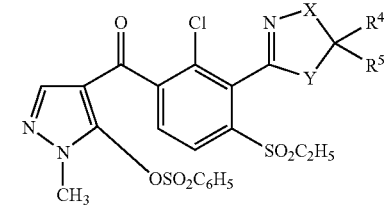
Ib252

The compounds Ib253.1-Ib253.126, which differ from the corresponding compounds Ib1.1-Ib1.126 by the fact that $R^{16}$ is ethyl, Z is phenylsulfonyl and $R^{18}$ is hydrogen.

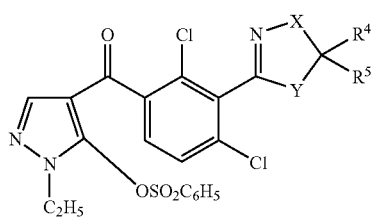
Ib253

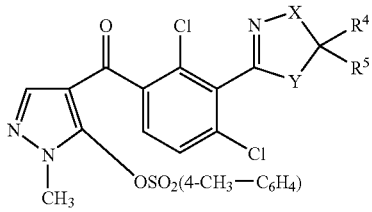
Ib257

The compounds Ib254.1-Ib254.126, which differ from the corresponding compounds Ib1.1-Ib1.126 by the fact that R² is methylsulfonyl, R¹⁶ is ethyl, Z is phenylsulfonyl and R¹⁸ is hydrogen.

The compounds Ib258.1-Ib258.126, which differ from the corresponding compounds Ib1.1-Ib1.126 by the fact that R² is methylsulfonyl, Z is p-toluenesulfonyl and R¹⁸ is hydrogen.

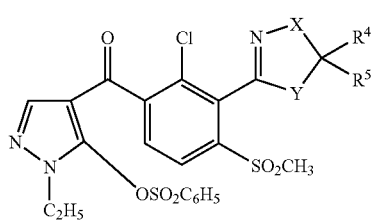
Ib254

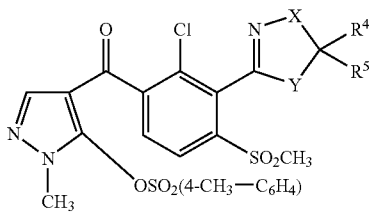
Ib258

The compounds Ib255.1-Ib255.126, which differ from the corresponding compounds Ib1.1-Ib1.126 by the fact that R¹ is methyl, R² is methylsulfonyl, R¹⁶ is ethyl, Z is phenylsulfonyl and R¹⁸ is hydrogen.

The compounds Ib259.1-Ib259.126, which differ from the corresponding compounds Ib1.1-Ib1.126 by the fact that R¹ is methyl, R² is methylsulfonyl, Z is p-toluenesulfonyl and R¹⁸ is hydrogen.

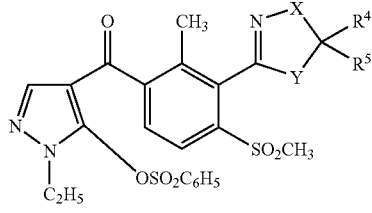
Ib255

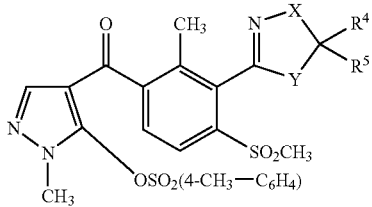
Ib259

The compounds Ib256.1-Ib256.126, which differ from the corresponding compounds Ib1.1-Ib1.126 by the fact that R² is ethylsulfonyl, R¹⁶ is ethyl, Z is phenylsulfonyl and R¹⁸ is hydrogen.

The compounds Ib260.1-Ib260.126, which differ from the corresponding compounds Ib1.1-Ib1.126 by the fact that R² is ethylsulfonyl, Z is p-toluenesulfonyl and R¹⁸ is hydrogen.

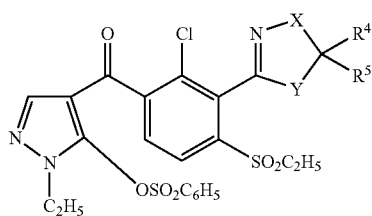
Ib256

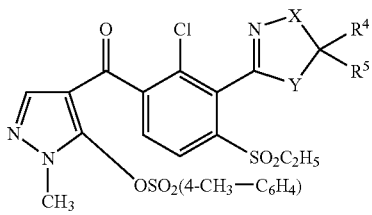
Ib260

The compounds Ib257.1-Ib257.126, which differ from the corresponding compounds Ib1.1-Ib1.126 by the fact that Z is p-toluenesulfonyl and R¹⁸ is hydrogen.

The compounds Ib261.1-Ib261.126, which differ from the corresponding compounds Ib1.1-Ib1.126 by the fact that R¹⁶ is ethyl, Z is p-toluenesulfonyl and R¹⁸ is hydrogen.

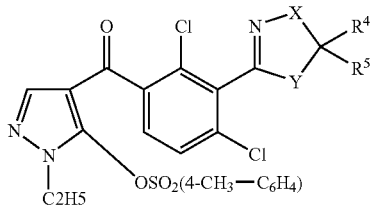

The compounds Ib262.1-Ib262.126, which differ from the corresponding compounds Ib1.1-Ib1.126 by the fact that $R^2$ is methylsulfonyl, $R^{16}$ is ethyl, Z is p-toluenesulfonyl and $R^{18}$ is hydrogen.

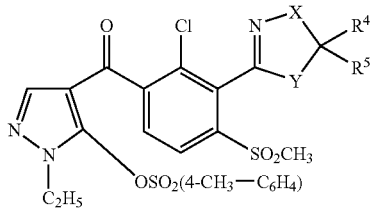

The compounds Ib263.1-Ib263.126, which differ from the corresponding compounds Ib1.1-Ib1.126 by the fact that $R^1$ is methyl, $R^2$ is methylsulfonyl, $R^{16}$ is ethyl, Z is p-toluenesulfonyl and $R^{18}$ is hydrogen.

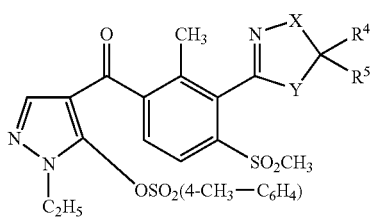

The compounds Ib264-Ib264.126, which differ from the corresponding compounds Ib1.1-Ib1.126 by the fact that $R^2$ is ethylsulfonyl, $R^{16}$ is ethyl, Z is p-toluenesulfonyl and $R^{18}$ is hydrogen.

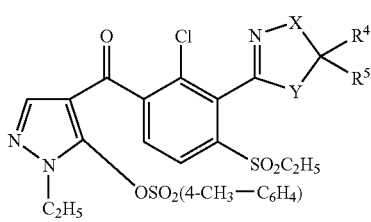

Also particularly preferred are 3-heterocyclyl-substituted benzoyl derivatives of the formula I where:

$R^1$ is halogen, $C_1$-$C_6$-alkyl, $C_1$-$C_6$-alkylthio or $C_1$-$C_6$-alkylsulfonyl;

in particular chlorine, methyl, methylthio or methylsulfonyl;

$R^2$ is hydrogen, nitro, halogen, $C_1$-$C_6$-alkylthio, $C_1$-$C_6$-alkylsulfinyl or $C_1$-$C_6$-alkylsulfonyl;

in particular hydrogen, nitro, chlorine, methylthio, methylsulfinyl, methylsulfonyl, ethylsulfonyl or propylsulfonyl;

$R^3$ is hydrogen;

$R^4$, $R^5$ are hydrogen, halogen, $C_1$-$C_4$-alkyl, $C_1$-$C_4$-haloalkyl, $C_1$-$C_4$-alkoxy, $C_1$-$C_4$-alkylthio or $COR^6$;

in particular hydrogen, fluorine, methyl, ethyl, propyl, trifluoromethyl, chloromethyl, 1-chloroeth-1-yl, methoxy, ethoxy, ethylthio or ethoxycarbonyl;

or $R^4$ and $R^5$ together form a $C_2$-$C_6$-alkanediyl chain which can be mono- to polysubstituted by $C_1$-$C_4$-alkyl and/or which can be interrupted by oxygen or by a nitrogen which is unsubstituted or substituted [lacuna] $C_1$-$C_4$-alkyl;

$R^6$ is $C_1$-$C_4$-alkoxy;

in particular ethyl;

X is O or $CR^{10}R^{11}$;

Y is O, S or $CR^{13}R^{14}$;

$R^{10}$, $R^{11}$, $R^{13}$, $R^{14}$ are hydrogen, $C_1$-$C_4$-alkyl or $C_1$-$C_4$-haloalkyl; in particular hydrogen, methyl or chloromethyl;

or $R^5$ and $R^{13}$ together form a $C_2$-$C_6$-alkanediyl chain which can be mono- to polysubstituted by $C_1$-$C_4$-alkyl and/or which can be interrupted by oxygen or by a nitrogen which is unsubstituted or substituted [lacuna] $C_1$-$C_4$-alkyl; in particular 1,3-propdiyl [sic];

$R^{16}$ is $C_1$-$C_6$-alkyl;

in particular methyl, ethyl, propyl, 2-methylpropyl or butyl;

Z is H or $SO_2R^{17}$;

$R^{17}$ is $C_1$-$C_4$-alkyl;

in particular methyl, ethyl, propyl or 2-methylpropyl;

with the exception of 4-[2-chloro-3-(4,5-dihydroisoxazol-3-yl)-4-methylsulfonylbenzoyl]-1-ethyl-5-hydroxy-1H-pyrazole, 4-[2-chloro-3-(4,5-dihydroisoxazol-3-yl)-4-methylsulfonyl-benzoyl]-1,3-dimethyl-5-hydroxy-1H-pyrazole, 4-[2-chloro-3-(5-cyano-4,5-dihydroisoxazol-3-yl)-4-methylsulfonylbenzoyl]-1,3-dimethyl-5-hydroxy-1H-pyrazole and 4-[2-chloro-3-(4,5-dihydrothiazol-2-yl)-4-methylsulfonylbenzoyl]-1,3-dimethyl-5-hydroxy-1H-pyrazole;

and the agriculturally useful salts thereof;

in particular alkali metal salts and ammonium salts.

The 3-heterocyclyl-substituted benzoyl derivatives of the formula I are obtainable by various routes, for example by the following process:

Process A:

Reaction of pyrazoles of the formula II (where Z=H) with an activated benzoic acid IIIα or a benxoic acid IIIβ, which is preferably activated in situ to give the acylating product and subsequently subjecting the latter to a rearrangement reaction.

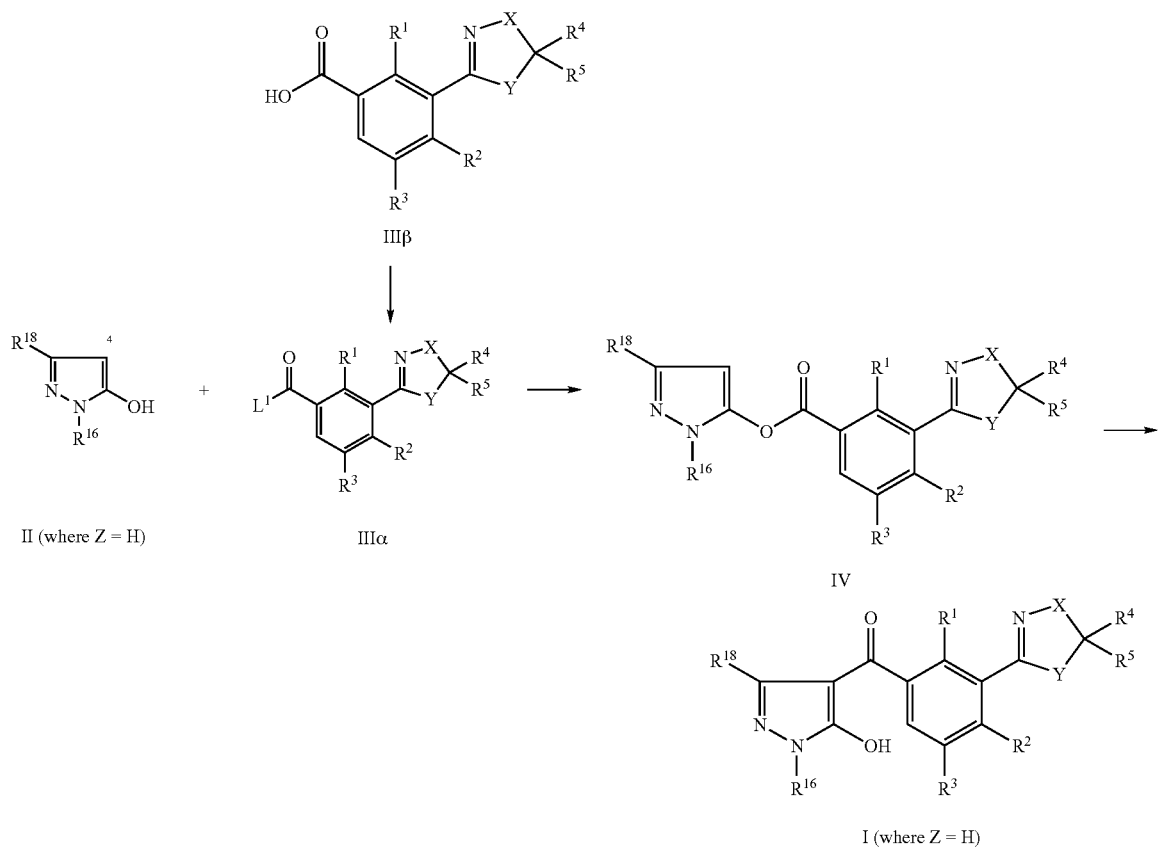

L¹ is a nucleophilically displaceable leaving group such as halogen, eg. bromine, chlorine, hetaryl, eg. imidazolyl, pyridyl, carboxylate, eg. acetate, trifluoroacetate, and the like.

The activated benzoic acid can be employed directly, as in the case of the benzoyl halides, or it can be prepared in situ, for example with dicyclohexylcarbodiimide, triphenylphosphine/azodicarboxylic ester, 2-pyridine disulfide/triphenylphosphine, carbonyldiimidazole and the like.

It may be advantageous to carry out the acylation reaction in the presence of a base. The reactants and the auxiliary base are expediently employed in equimolar amounts. A small excess of the auxiliary base, for example 1.2 to 1.5 mol equivalents based on II, may be advantageous under certain circumstances.

Suitable auxiliary bases are tertiary alkylamines, pyridine or alkali metal carbonates. Examples of solvents which can be used are chlorinated hydrocarbons such as methylene chloride, 1,2-dichloroethane, aromatic hydrocarbons such as toluene, xylene, chlorobenzene, ethers such as diethyl ether, methyl tert-butyl ether, tetrahydrofuran, dioxane, polar aprotic solvents such as acetonitrile, dimethylformamide, dimethyl sulfoxide, or esters such as ethyl acetate, or mixtures of these.

If benzoyl halides are employed as activated carboxylic acid component, it may be expedient to cool the reaction mixture to 0-10° C. when adding this reactant. The mixture is subsequently stirred at 20-100° C., preferably at 25-50° C., until the reaction is complete. Work-up is carried out in the customary manner, for example the reaction mixture is poured into water and the product of value is extracted. Especially suitable solvents for this purpose are methylene chloride, diethyl ether and ethyl acetate. After the organic phase has been dried and the solvent removed, the crude ester can be employed without further purification for the rearrangement reaction.

Rearrangement of the esters to give the compounds of the formula I is expediently carried out at from 20 to 40° C. in a solvent and in the presence of a base and, if appropriate, with the aid of a cyano compound as catalyst.

Examples of solvents which can be used are acetonitrile, methylene chloride, 1,2-dichlorethane, dioxane, ethyl acetate, toluene or mixtures of these. Preferred solvents are acetonitrile and dioxane.

Suitable bases are tertiary amines such triethylamine, pyridine, or alkali metal carbonates such as sodium carbonate, potassium carbonate, all of which are preferably employed in equimolar amounts or up to a fourfold excess, based on the ester. Triethylamine or alkali metal carbonate are preferably used, but by preference in a ratio of twice the equimolar amount based on the ester.

Suitable cyano compounds are inorganic cyanides such as sodium cyanide, potassium cyanide, and organic cyano compounds such as acetone cyanohydrin, trimethylsily cyanide. They are employed in an amount of from 1 to 50 mol percent, based on the ester. Substances which are preferably employed are acetone cyanohydrin or trimethylsilyl cyanide, for example in an amount of from 5 to 15, preferably 10, mol percent, based on the ester.

Work-up can be effected in a manner known per se. For example, the reaction mixture is acidified with dilute mineral acid, such as 5% strength hydrochloric acid or sulfuric acid, and extracted with an organic solvent, eg. methylene chloride or ethyl acetate. The organic extract can be extracted with 5-10% strength alkali metal carbonate solution, eg. sodium carbonate or potassium carbonate solution. The aqueous phase is acidified, and the precipitate which forms is filtered off with suction and/or extracted with methylene chloride or ethyl acetate, dried and concentrated. (Examples of the synthesis of esters from hydroxypyrazoles and of the rearrangement of the esters are mentioned, for example, in EP-A 282 944 and U.S. Pat. No. 4,643,757).

Process B:

Reaction of 3-heterocyclyl-substituted benzoyl derivatives of the formula I (where Z=H) with a compound of the formula V (where Z=$SO_2R^{17}$)

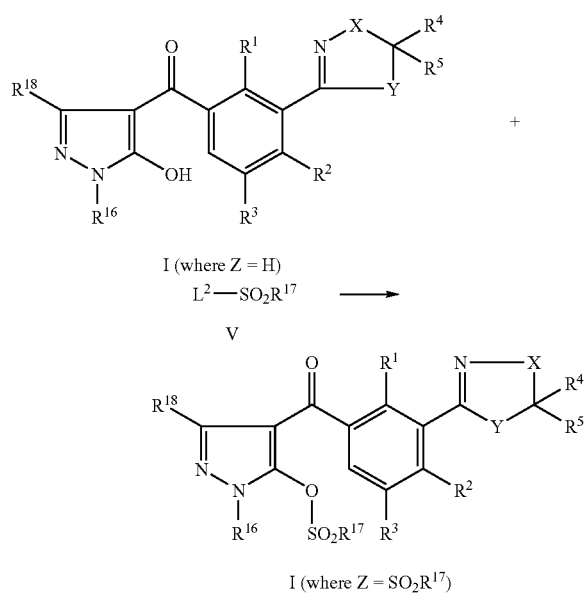

$L^2$ is a nucleophilically displaceable leaving group, such as halogen, eg. bromine, chlorine, hetaryl, eg. imidazolyl, pyridyl, sulfonate, eg. $OSO_2R^{17}$.

The compounds of the formula V can be employed directly such as, for example, in the case of the sulfonyl halides or sulfonic anhydrides, or they can be prepared in situ, for example activated sulfonic acids (by means of sulfonic acid and dicyclohexylcarbodiimide, carbonyldiimidazole and the like).

As a rule, the starting compounds are employed in an equimolar ratio. However, it may also be advantageous to employ an excess of one or the other component.

It may be advantageous to carry out the reaction in the presence of a base. The reactants and the auxiliary base are expediently employed in equimolar ratios. An excess of the auxiliary base, for example 1.5 to 3 mol equivalents, based on II, may be advantageous under certain circumstances.

Suitable auxiliary bases are tertiary alkylamines such as triethylamine or pyridine, alkali metal carbonates, eg. sodium carbonate or potassium carbonate, and alkali metal hydrides, eg. sodium hydride. Triethylamine and pyridine are preferably used.

Examples of suitable solvents are chlorinated hydrocarbons such as methylene chloride or 1,2-dichlorethane, aromatic hydrocarbons, eg. toluene, xylene or chlorobenzene, ethers such as diethyl ether, methyl tert-butyl ether, tetrahydrofuran or dioxane, polar aprotic solvents such as acetonitrile, dimethylformamide or dimethyl sulfoxide, or esters such as ethyl acetate, or mixtures of these.

As a rule, the reaction temperature is in the range of from 0° C. to the boiling point of the reaction mixture.

Work-up can be effected in a manner known per se to give the product.

Those pyrazoles of the formula II (where Z=H) which are used as starting materials and which are not already known can be prepared by processes known per se (for example EP-A 240 001 and J. Prakt. Chem. 315, 383 (1973)).

Novel 3-heterocyclyl-substituted benzoic acid derivatives of the formula III

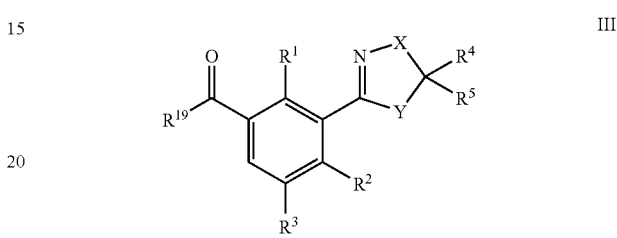

are those where the variables have the following meanings:

$R^1$, $R^2$ are hydrogen, nitro, halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl or $C_1$-$C_6$-haloalkylsulfonyl;

$R^3$ is hydrogen, halogen or $C_1$-$C_6$-alkyl;

$R^4$, $R^5$ are hydrogen, halogen, cyano, nitro, $C_1$-$C_4$-alkyl, $C_1$-$C_4$-alkoxy-$C_1$-$C_4$-alkyl, di($C_1$-$C_4$-alkoxy)-$C_1$-$C_4$-alkyl, di($C_1$-$C_4$-alkyl)amino-$C_1$-$C_4$-alkyl, [2,2-di($C_1$-$C_4$-alkyl)hydrazino-1]-$C_1$-$C_4$-alkyl, $C_1$-$C_6$-alkyliminooxy-$C_1$-$C_4$-alkyl, $C_1$-$C_4$-alkoxycarbonyl-$C_1$-$C_4$-alkyl, $C_1$-$C_4$-alkylthio-$C_1$-$C_4$-alkyl, $C_1$-$C_4$-haloalkyl, $C_1$-$C_4$-cyanoalkyl, $C_3$-$C_8$-cycloalkyl, $C_1$-$C_4$-alkoxy, $C_1$-$C_4$-alkoxy-$C_2$-$C_4$-alkoxy, $C_1$-$C_4$-haloalkoxy, hydroxyl, $C_1$-$C_4$-alkylcarbonyloxy, $C_1$-$C_4$-alkylthio, $C_1$-$C_4$-haloalkylthio, di($C_1$-$C_4$-alkyl)amino, $COR^6$, phenyl or benzyl, it being possible for the two last-mentioned substituents to be partially or fully halogenated and/or to have attached to them one to three of the following groups: nitro, cyano, $C_1$-$C_4$-alkyl, $C_1$-$C_4$-haloalkyl, $C_1$-$C_4$-alkoxy or $C1$-$C4$-haloalkoxy;

or $R^4$ and $R^5$ together form a $C_2$-$C_6$-alkanediyl chain which can be mono- to tetrasubstituted by $C_1$-$C_4$-alkyl and/or which can be interrupted by oxygen or by a nitrogen which is unsubstituted or substituted by $C_1$-$C_4$-alkyl;

or $R^4$ and $R^5$ together with the corresponding carbon form a carbonyl or a thiocarbonyl group;

$R^6$ is hydrogen, $C_1$-$C_4$-alkyl, $C_1$-$C_4$-haloalkyl, $C_1$-$C_4$-alkoxy, $C_1$-$C_4$-alkoxy-$C_2$-$C_4$-alkoxy, $C_1$-$C_4$-haloalkoxy, $C_3$-$C_6$-alkenyloxy, $C_3$-$C_6$-alkynyloxy or $NR^7R^8$;

$R^7$ is hydrogen or $C_1$-$C_4$-alkyl;

$R^8$ is $C_1$-$C_4$-alkyl;

X is O, S, $NR^9$, CO or $CR^{10}R^{11}$;

Y Y is O, S, $NR^{12}$, CO or $CR^{13}R^{14}$;

$R^9$, $R^{12}$ are hydrogen or $C_1$-$C_4$-alkyl;

$R^{10}$, $R^{11}$, $R^{13}$, $R^{14}$ are hydrogen, $C_1$-$C_4$-alkyl, $C_1$-$C_4$-haloalkyl, $C_1$-$C_4$-alkoxycarbonyl, $C_1$-$C_4$-haloalkoxycarbonyl or $CONR^7R^8$;

or $R^4$ and $R^9$ or $R^4$ and $R^{10}$ or $R^5$ and $R^{12}$ or $R^5$ and $R^{13}$ together form a $C_2$-$C_6$-alkanediyl chain which can be mono- to tetrasubstituted by $C_1$-$C_4$-alkyl and/or which can be interrupted by oxygen or by a nitrogen which is unsubstituted or substituted by $C_1$-$C_4$-alkyl;

$R^{19}$ is hydroxyl or a radical which can be removed by hydrolysis;

with the exception of methyl 2-chloro-3-(4,5-dihydroisoxazol-3-yl)-4-methylsulfonylbenzoate, methyl 2-chloro-3-(4,5-dihydrooxazol-2-yl)-4-methylsulfonylbenzoate and methyl 2,4-dichloro-3-(5-methylcarbonyloxy-4,5-dihydroisoxazol-3-yl)-benzoate.

Examples of radicals which can be removed by hydrolysis are alkoxy, phenoxy, alkylthio and phenylthio radicals which are unsubstituted or substituted, halides, hetaryl radicals which are bonded via nitrogen; amino, imino radicals which are unsubstituted or substituted, and the like.

Preferred are 3-heterocyclyl-substituted benzoic acid halides of the formula IIIα', where $L^{1'}$=halogen ($\hat{=}$III where $R^{19}$=halogen)

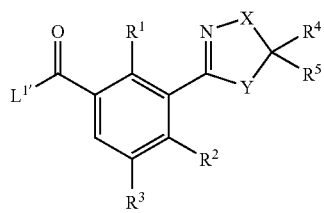

IIIα' where the variables $R^1$ to $R^5$, X and Y have the meanings given under the formula III and $L^{1'}$ is halogen, in particular chlorine or bromine.

Equally preferred are 3-heterocyclyl-substituted benzoic acids of the formula IIIβ ($\hat{=}$III where $R^{19}$=hydroxyl)

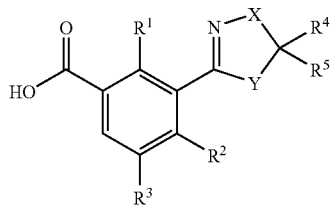

IIIβ where the variables $R^1$ to $R^5$, X and Y have the meanings given under the formula III.

Equally preferred are 3-heterocyclyl-substituted benzoic esters of the formula IIIγ ($\hat{=}$III where $R^{19}$=$C_1$-$C_6$-alkoxy)

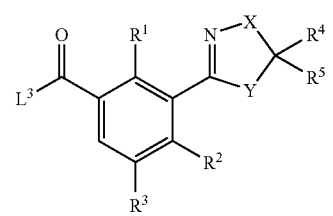

IIIγ where the variables $R^1$ to $R^5$, X and Y have the meanings given under formula III and $L^3$ is $C_1$-$C_6$-alkoxy.

The specially preferred embodiments of the 3-heteroacyclyl-substituted benzoic acid derivatives of the formula III with regard to the variables $R^1$ to $R^5$, X and Y correspond to those of the 3-heterocyclyl-substituted benzoyl derivatives of the formula I.

Also preferred are 3-heterocyclyl-substituted benzoic acid derivatives of the formula III, where:

$R^1$ is halogen, $C_1$-$C_6$-alkyl, $C_1$-$C_6$-alkylthio or $C_1$-$C_6$-alkylsulfonyl;

in particular chlorine, methyl, methylthio or methylsulfonyl;

extraordinarily preferably chlorine;

$R^2$ is hydrogen, nitro, halogen, $C_1$-$C_6$-alkylthio, $C_1$-$C_6$-alkylsulfinyl or $C_1$-$C_6$-alkylsulfonyl;

in particular hydrogen, nitro, chlorine, methylthio, methylsulfinyl, methylsulfonyl, ethylsulfonyl or propylsulfonyl;

extraordinarily preferably hydrogen, chlorine, methylthio, methylsulfonyl, ethylsulfonyl or propylsulfonyl;

$R^3$ is hydrogen;

$R^4$, $R^5$ are hydrogen, halogen, $C_1$-$C_4$-alkyl, $C_1$-$C_4$-haloalkyl, $C_1$-$C_4$-alkoxy, hydroxyl, $C_1$-$C_4$-alkylcarbonyloxy, $C_1$-$C_4$-alkylthio or $COR^6$;

in particular hydrogen, fluorine, methyl, ethyl, propyl, trifluoromethyl, chloromethyl, 2-chloroeth-1-yl, methoxy, ethoxy, 2-methylprop-1-oxy, hydroxyl, methylcarbonyloxy, ethylthio, formyl, methylcarbonyl, methoxycarbonyl or ethoxycarbonyl;

extraordinarily preferably hydrogen, fluorine, methyl, ethyl, trifluoromethyl, chloromethyl, 2-chloroeth-1-yl, methoxy, ethoxy, 2-methylprop-1-oxy, hydroxyl, methylcarbonyloxy, ethylthio, formyl, methylcarbonyl, methoxycarbonyl or ethoxycarbonyl;

or $R^4$ and $R^5$ together form a $C_2$-$C_6$-alkanediyl chain which can be mono- to polysubstituted by $C_1$-$C_4$-alkyl and/or which can be interrupted by oxygen or by a nitrogen which is unsubstituted or substituted by $C_1$-$C_4$-alkyl;

in particular 1,4-butdiyl, 2-oxo-1,5-pentdiyl;

or $R^4$ and $R^5$ together with the corresponding carbon atoms form a carbonyl group $R^6$ is hydrogen, $C_1$-$C_4$-alkyl or $C_1$-$C_4$-alkoxy;

in particular hydrogen, methyl, methoxy or ethoxy;

X is O, S, CO, $CR^{10}R^{11}$;

Y is O, S, $CR^{13}R^{14}$;

$R^{10}$, $R^{11}$, $R^{13}$, $R^{14}$ are hydrogen, $C_1$-$C_4$-alkyl, $C_1$-$C_4$-haloalkyl or $C_1$-$C_4$-alkoxycarbonyl;

in particular hydrogen, methyl, chloromethyl or methoxycarbonyl;

or $R^5$ and $R^{13}$ together form a $C_2$-$C_6$-alkanediyl chain which can be mono- to polysubstituted by $C_1$-$C_4$-alkyl and/or which can be interrupted by oxygen or by a nitrogen which is unsubstituted or substituted by $C_1$-$C_4$-alkyl;

in particular 1,3-propdiyl;

$R^{19}$ is hydroxyl, halogen or $C_1$-$C_6$-alkoxy;

in particular hydroxyl, chlorine, methoxy or ethoxy;

with the exception of methyl 2-chloro-3-(4,5-dihydroisoxazol-3-yl)-4-methylsulfonylbenzoate, methyl 2-chloro-3-(4, 5-dihydro-oxazol-2-yl)-4-methylsulfonylbenzoate and methyl 2,4-dichloro-3-(5-methylcarbonyloxy-4,5-dihydroisoxazol-3-yl)benzoate.

The benzoyl halides of the formula IIIα' (where $L^{1'}$=Cl, Br) can be prepared in a manner known per se by reacting the benzoic acids of the formula IIIβ with halogenating reagents such as thionyl chloride, thionyl bromide, phosgene, diphosgene, triphosgene, oxalyl chloride or oxalyl bromide.

The benzoic acids of the formula IIIβ can be prepared in a known manner from the corresponding esters of the formula IIIγ ($L^3=C_1-C_6$-alkoxy) by means of acid or basic hydrolysis.

Equally, the benzoic acids of the formula IIIβ can be obtained by reacting corresponding bromine- or iodine-substituted compounds of the formula V, with carbon monoxide and water under elevated pressure in the presence of a palladium, nickel, cobalt or rhodium transition metal catalyst and a base.

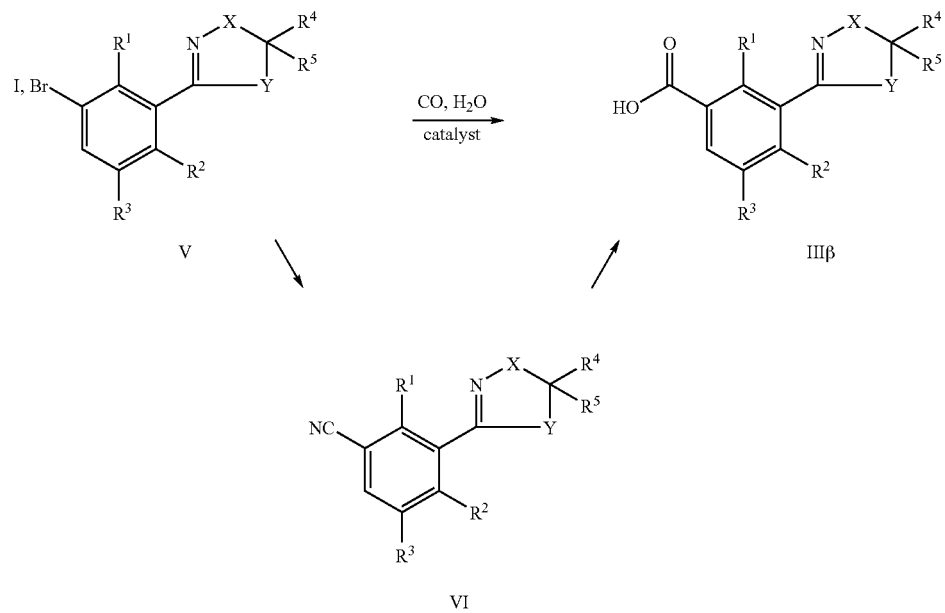

Furthermore, it is possible to convert compounds of the formula V into the corresponding nitrites of the formula VI by a Rosenmund-von Braun reaction (cf., for example, Org. Synth. Vol III (1955), 212) and to convert these nitrites into the compounds of the formula IIIβ by subsequent hydrolysis.

The esters of the formula IIIγ can be obtained by reacting arylhalogen compounds or arylsulfonates of the formula VII, where $L^4$ is a leaving group such as bromine, iodine, triflate, fluorosulfonyloxy and the like with heterocyclyl stannates (Stille couplings), heterocyclyl-boron compounds (Suzuki couplings) or heterocyclyl-zinc compounds (Negishi reaction) VIII, where M is $Sn(C_1-C_4\text{-alkyl})_3$, $B(OH)_2$, ZnHal (where Hal=chlorine, bromine) and the like, respectively, in a manner known per se (cf., for example, Tetrahedron Lett. 27 (1986), 5269) in the presence of a palladium or nickel transition metal catalyst and in the presence or absence of a base.

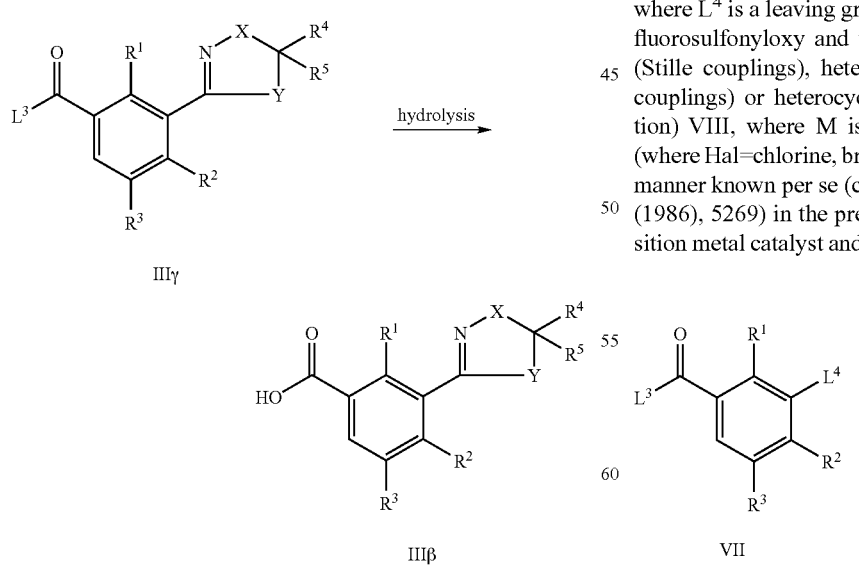

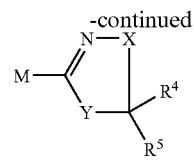

VIII (where M = Sn(C$_1$-C$_4$-Alkyl)$_3$,
B(OH)$_2$, ZnHal,
where Hal is Cl or Br)

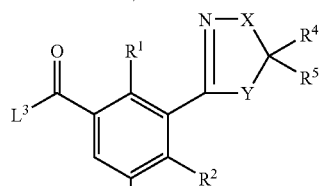

IIIγ

Equally, it is possible to obtain esters of the formula IIIγ by synthesizing the heterocycle which is bonded in the 3-position.

For example, 1,2,4-oxadiazolin-3-yl derivatives (IIIγ where X=O, Y=NH) can be prepared from amidoximes of the formula IX by condensation with aldehydes or ketones (cf., for example, Arch. Phar. 326 (1993), 383-389).

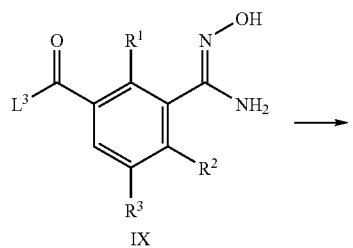

IX

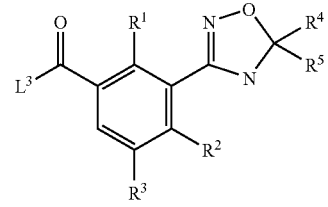

IIIγ
(where X = O, Y = NH)

Thioamides of the formula X are suitable precursors for 2-thiazolinyl derivatives I (where X=CR$^{10}$R$^{11}$, Y=S) (cf., for example, Tetrahedron 42 (1986), 1449-1460).

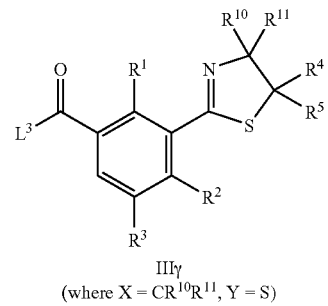

X

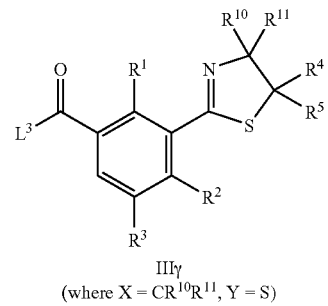

IIIγ
(where X = CR$^{10}$R$^{11}$, Y = S)

2-Oxazolinyl, 2-thiazolinyl and 2-imidazolinyl derivatives (IIIγ where X=CR$^{10}$R$^{11}$, Y=O or Y=S or Y=NH) are accessible from the carboxylic acids of the formula XI (cf., for example, Tetrahedron Let. 22 (1981), 4471-4474).

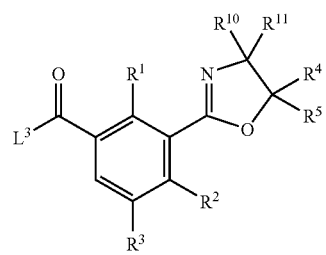

IIIγ
(where X = CR$^{10}$R$^{11}$, Y = O)

-continued

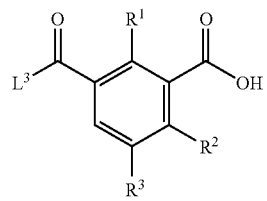

XI

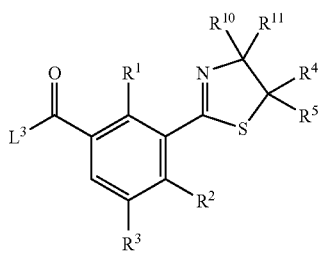

IIIγ
(where X = CR$^{10}$R$^{11}$, Y = S)

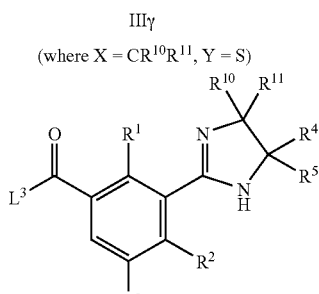

IIIγ
(where X = CR$^{10}$R$^{11}$, Y = NH)

1,3-Thiazol-5(4H)-thion-2-yl (cf., for example, Helv. Chim. Acta 69 (1986), 374-388) and 5-oxo-2-imidazolin-2-yl derivatives (cf., for example, Heterocycles 29 (1989), 1185-1189) (III where X=CR$^{10}$R$^{11}$, Y=S or Y=NH) can be prepared by processes known from the literature from carboxylic acid halides of the formula XII where Hal is halogen, in particular from carboxylic acid chlorides.

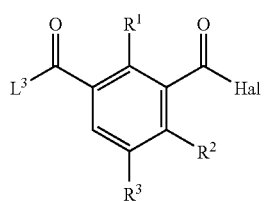

XII

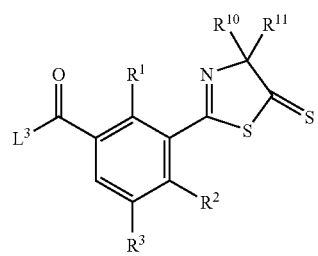

IIIγ
(where X = CR$^{10}$R$^{11}$, Y = S)

-continued

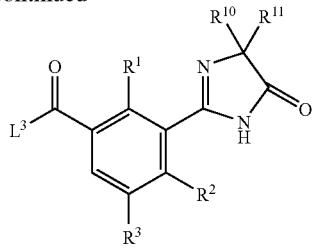

IIIγ

(where X = CR¹⁰R¹¹, Y = NH)

The oximes of the formula XIII can be converted into 4,5-dihydroisoxazol-3-yl derivatives (IIIγ where X=O, Y=CR¹³R¹⁴) in a manner known per se via the hydroxamic acid chlorides XIV as intermediates. From the latter, nitrile oxides are prepared in situ, and these nitrile oxides react with alkenes to give the desired products (cf., for example, Chem. Ber. 106 (1973), 3258-3274). 1,3-Dipolar cycloaddition reactions of chlorosulfonyl isocyanate with nitrile oxides yield 1,2,4-oxadiazolin-5-on-3-yl derivatives (IIIγ where X=O, Y=NH) (cf., for example, Heterocycles 27 (1988), 683-685).

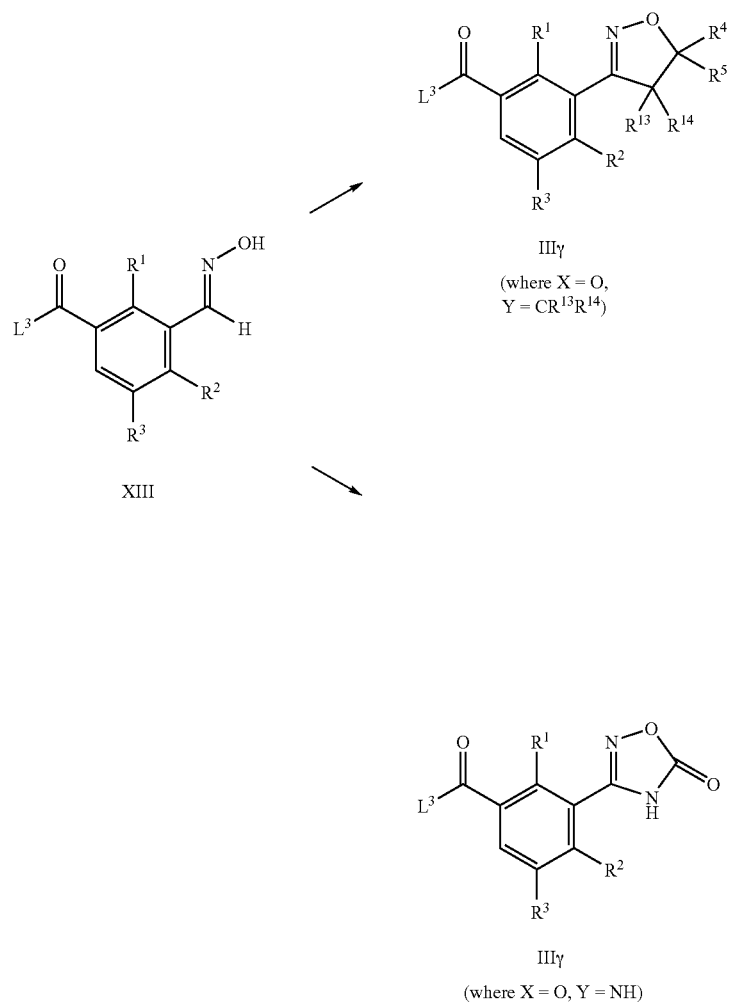

The aldehydes of the formula XIV can be converted into 2,4-dihydro-1,2,4-triazol-3-on-5-yl derivatives (IIIγ where X=NR⁹, X=NR¹²) via the semicarbazones as intermediates (cf., for example, J. Heterocyclic Chem. 23 (1986), 881-883).

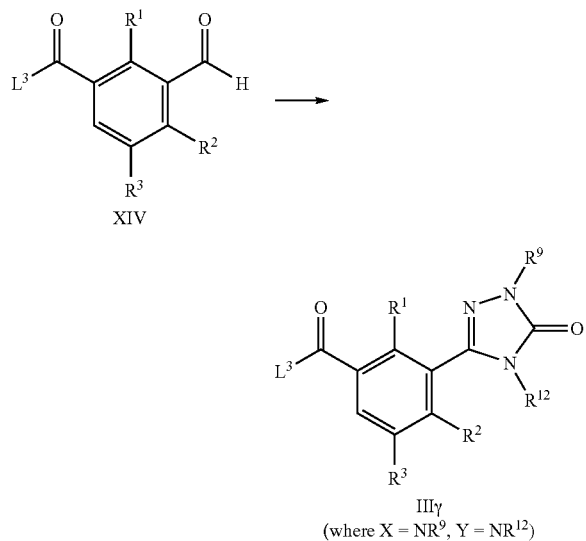

2-Imidazolinyl derivatives (IIIγ where X=CR¹⁰R¹¹, Y=NH) can also be prepared from benzonitriles of the formula XV using known methods (cf., for example, J. Org. Chem. 52 (1987), 1017-1021).\

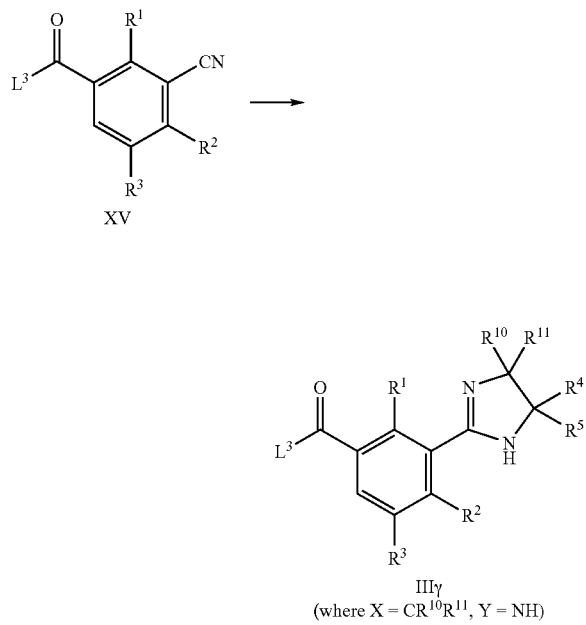

1,3-Dipolar cycloaddition reactions of diazoalkanes or nitriloimines with arylalkenes of the formula XVI can be used for synthesizing 3-pyrazolinyl derivatives (IIIγ where X=NH, Y=CHR¹³)

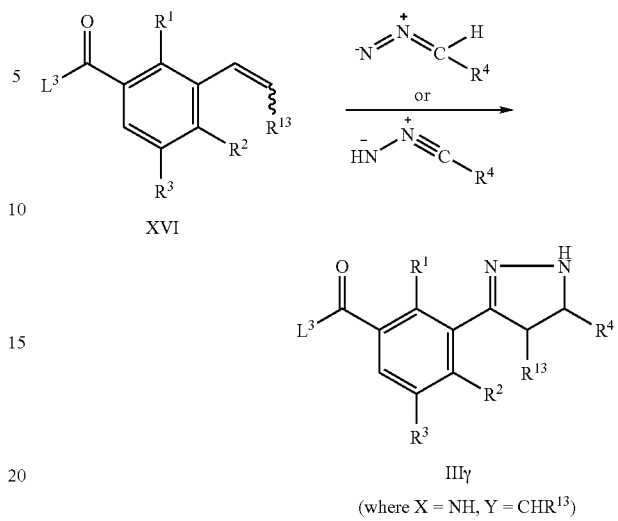

The bromine- or iodine-substituted compounds of the formula V which are used as starting compounds can be obtained from corresponding anilines by method similar to those known from the literature, for example by Sandmeyer reaction, and the anilines, in turn, are synthesized by reducing suitable nitro compounds. The bromine-substituted compounds of the formula V can additionally be obtained by direct bromination of suitable starting materials (cf. Monatsh. Chem. 99 (1968), 815-822).

The nitriles of the formula VI can be obtained as described above. Equally, it is possible to synthesize them from corresponding anilines by means of a Sandmeyer reaction.

The starting compounds of the formula VII are known (cf., for example, Coll. Czech. Chem. Commun. 40 (1975), 3009-3019) or can be prepared readily by a suitable combination of known syntheses.

For example, the sulfonates VII ($L^4$=OSO$_2$CF$_3$, OSO$_2$F) can be obtained from the corresponding phenols, which, in turn, are known (cf., for example, EP-A 195 247) or can be prepared by known methods (cf., for example, Synthesis 1993, 735-762).

The halogen compounds VII ($L^4$=Cl, Br or I) can be obtained, for example, from the corresponding anilines of the formula XIX by a Sandmeyer reaction.

The amidoximes of the formula IX, the thioamides of the formula X and the carboxylic acids of the formula XI can be synthesized from the nitriles of the formula XV in a manner known per se.

Furthermore, it is possible to prepare the carboxylic acids of the formula XI from the aldehydes of the formula XIV by known processes (cf., for example, J. March, Advanced Organic Chemistry, 3rd edition (1985), p. 629 et seq., Wiley-Interscience Publication).

The carboxylic acid halides of the formula XII can be obtained from the corresponding carboxylic acids of the formula XI by methods similar to standard processes.

The oximes of the formula XIII are advantageously obtained by reacting aldehydes of the formula XIV with hydroxylamine in a manner known per se (cf., for example, J. March, Advanced Organic Chemistry, 3rd ed. (1985), pp. 805-806, Wiley-Interscience Publication).

Those aldehydes of the formula XIV which are not already known can be prepared by methods similar to known processes. Thus, they can be synthesized from methyl compounds of the formula XVII by means of bromination, for example with N-bromosuccinimide or 1,3-dibromo-5,5-dimethylhydantoin, followed by oxidation (cf. Synth. Commun. 22 (1992), 1967-1971).

The oximes of the formula XIII can also be converted into nitrites of the formula XV by processes which are known per se (cf., for example, J. March, Advanced Organic Chemistry, 3rd ed. (1985), pp. 931-932, Wiley-Interscience Publication).

Arylalkenes of the formula XVI can be synthesized starting from the halogen compounds or sulfonates of the formula VII ($L^4$=Br, Cl, $OSO_2CF_3$, $OSO_2F$) by, inter alia, Heck reaction with olefins in the presence of a palladium catalyst (cf., for example, Heck, Palladium Reagents in Organic Synthesis, Academic Press, London 1985; Synthesis 1993, 735-762).

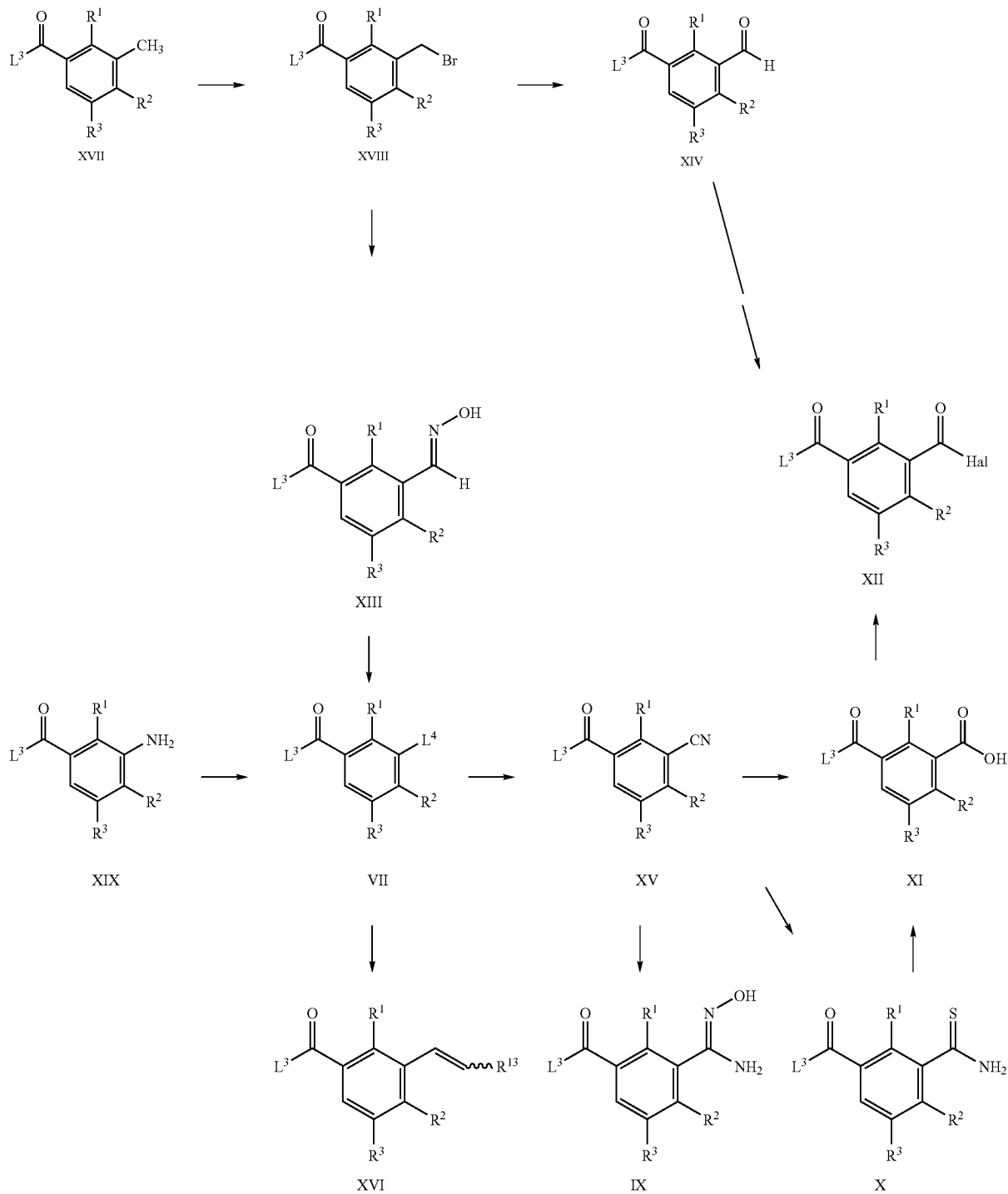

PREPARATION EXAMPLES

4-[2-Chloro-3-(4,5-dihydroisoxazol-3-yl)-4-methyl-sulfonyl-benzoyl]-5-hydroxy-1-methyl-1H-pyrazole (compound 3.35)

43.60 g (0.13 mol) of 2-chloro-3-(4,5-dihydroisoxazol-3-yl)-4-methylsulfonylbenzoyl chloride in 375 ml of anhydrous dioxane and 13.56 g (0.134 mol) of triethylamine in 375 ml of anhydrous dioxane are simultanouesly added dropwise at room temperature under a protective gas atmosphere to a solution 12.74 g (0.13 mol) of 5-hydroxy-1-methylpyrazole and 300 ml of anhydrous dioxane. After the reaction mixture had been stirred for 2 hours at room temperature, it was filtered through silica gel and the residue was washed with dioxane. The eluate was concentrated in vacuo to approximately 500 ml, and 17.94 by(0.13 mol) of dried, finely powdered potassium carbonate were added. After the mixture had been refluxed for 6 hours, the solvent was distilled off in vacuo and the residue was taken up in approximately 700 ml of water. Insoluble constituents were filtered off, and the pH of the filtrate was brought to 2-3 by slow addition of 10% strength hydrochloric acid. The precipitate which formed was filtered off with suction. This gave 46.16 g (92% of theory) of 4-[2-chloro-3-(4,5-dihydroisoxazol-3-yl)-4-methylsulfonyl-benzoyl]-5-hydroxy-1-methyl-1H-pyrazole.

(m.p.>250° C.)

Table 3 shows the above compound and, in addition, other 3-heterocyclyl-substituted benzoyl derivatives of the formula I which were prepared, or can be prepared, in a similar manner (if the end products had not precipitated upon acidification with 10% strength hydrochloric acid, they were extracted with ethyl acetate or dichloromethane; the organic phase was subsequently dried and concentrated in vacuo):

TABLE 3

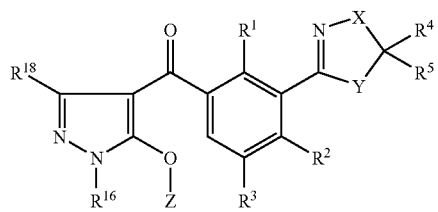

I

| No. | $R^1$ | $R^2$ | $R^3$ | X | $R^4$ | $R^5$ | Y | $R^{16}$ | Z | $R^{18}$ | Physical data m.p. [° C.]; $^1$H NMR [δ in ppm] |
|---|---|---|---|---|---|---|---|---|---|---|---|
| 3.1 | Cl | Cl | H | O | H | H | $CH_2$ | $n-C_4H_9$ | H | H | 116-117 |
| 3.2 | Cl | Cl | H | O | H | H | $CH_2$ | $i-C_4H_9$ | H | H | 148-151 |
| 3.3 | Cl | Cl | H | O | H | H | $CH_2$ | $n-C_4H_9$ | $C_2H_5SO_2$ | H | 0.95(t); 1.32(m); 1.62(t); 1.92(quin); 3.30(t); 3.78(quar) 4.17(t); 4.61(t); 7.42(d); 7.48(m). |
| 3.4 | Cl | Cl | H | O | H | H | $CH_2$ | $i-C_4H_9$ | $i-C_4H_9SO_2$ | H | 0.96(d); 1.21(d); 2.33(m); 2.48(m); 3.30(t); 3.67(d); 3.97(d); 4.58(t); 7.42(d); 7.50(m). |
| 3.5 | Cl | Cl | H | O | H | H | $CH_2$ | $n-C_3H_7$ | $i-C_4H_9SO_2$ | H | 0.97(t); 1.20(d); 1.96(m); 2.49(m); 3.30(t); 3.68(d); 4.12(t); 4.59(t); 7.42(d); 7.49(d); 7.52(s). |
| 3.6 | Cl | Cl | H | O | H | H | $CH_2$ | $n-C_3H_7$ | $C_2H_5SO_2$ | H | 0.97(t),1.12(d); 1.63(t); 1.94(m); 3.29(t); 3.76(q); 4.14(t); 4.60(t); 7.42(d),7.48(d); 7.51(s). |
| 3.7 | Cl | $SO_2CH_3$ | H | O | $COOC_2H_5$ | H | $CH_2$ | $CH_3$ | H | H | 70-75 |
| 3.8 | Cl | $SO_2CH_3$ | H | O | $COOC_2H_5$ | H | $CH_2$ | $C_2H_5$ | H | H | 65-70 |
| 3.9 | Cl | $SO_2CH_3$ | H | O | $CH_3$ | H | $CH_2$ | $CH_3$ | H | H | 230-235 |
| 3.10 | Cl | $SO_2CH_3$ | H | O | $CH_3$ | H | $CH_2$ | $C_2H_5$ | H | H | 210-215 |
| 3.11 | Cl | $SO_2CH_3$ | H | O | $CH_3$ | H | $CH_2$ | $n-C_3H_7$ | H | H | 95-100 |
| 3.12 | Cl | $SO_2CH_3$ | H | O | $CH_3$ | H | $CH_2$ | $CH_3$ | $C_2H_5SO_2$ | H | 70-75 |
| 3.13 | Cl | $SO_2CH_3$ | H | O | $CH_3$ | H | $CH_2$ | $C_2H_5$ | $C_2H_5SO_2$ | H | 78-83 |
| 3.14 | Cl | $SO_2CH_3$ | H | O | $CH_3$ | H | $CH_2$ | $C_2H_5$ | $i-C_4H_9SO_2$ | H | 1.24(2d); 1.53(t); 2.52(m); 3.05(dd); 3.29(s); 3.52(dd); 3.73(d); 4.24(q), |

TABLE 3-continued

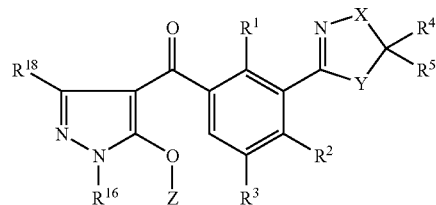

| No. | $R^1$ | $R^2$ | $R^3$ | X | $R^4$ | $R^5$ | Y | $R^{16}$ | Z | $R^{18}$ | Physical data m.p. [° C.]; $^1$H NMR [δ in ppm] |
|---|---|---|---|---|---|---|---|---|---|---|---|
| 3.15 | Cl | $SO_2CH_3$ | H | O | $CH_3$ | H | $CH_2$ | n-$C_3H_7$ | $C_2H_5SO_2$ | H | 5.05(m); 7.49(s); 7.66(d); 8.18(d). 0.96(t); 1.53(d); 1.68(t); 1.95(sext); 3.07(dd); 3.32(s); 3.58(dd); 3.86(quart); 4.15(t); 5.03(m); 7.46(d); 7.64(d); 8.18(d). |
| 3.16 | Cl | $SO_2CH_3$ | H | O | $CH_3$ | $CH_3$ | $CH_2$ | $CH_3$ | H | H | 220-225 |
| 3.17 | Cl | $SO_2CH_3$ | H | O | $CH_3$ | $CH_3$ | $CH_2$ | $C_2H_5$ | H | H | 82-86 |
| 3.18 | Cl | $SO_2CH_3$ | H | O | $CH_3$ | $CH_3$ | $CH_2$ | n-$C_3H_7$ | H | H | 70-75 |
| 3.19 | Cl | $SO_2CH_3$ | H | O | $CH_3$ | $CH_3$ | $CH_2$ | n-$C_4H_9$ | H | H | 68-73 |
| 3.20 | Cl | $SO_2CH_3$ | H | O | $CH_3$ | $CH_3$ | $CH_2$ | i-$C_4H_9$ | H | H | 45-50 |
| 3.21 | Cl | $SO_2CH_3$ | H | O | $C_2H_5$ | H | $CH_2$ | $CH_3$ | H | H | 220-225 |
| 3.22 | Cl | $SO_2CH_3$ | H | O | $C_2H_5$ | H | $CH_2$ | $C_2H_5$ | H | H | 170-175 |
| 3.23 | Cl | $SO_2CH_3$ | H | O | H | H | $CH_2$ | n-$C_3H_7$ | H | H | 65-70 |
| 3.24 | Cl | $SO_2CH_3$ | H | O | H | H | $CH_2$ | n-$C_4H_9$ | H | H | 55-60 |
| 3.25 | Cl | $SO_2CH_3$ | H | O | H | H | $CH_2$ | i-$C_4H_9$ | H | H | 58-63 |
| 3.26 | Cl | $SO_2CH_3$ | H | O | H | H | $CH_2$ | n-$C_4H_9$ | $C_2H_5SO_2$ | H | 78-83 |
| 3.27 | Cl | $SO_2CH_3$ | H | O | H | H | $CH_2$ | n-$C_4H_9$ | i-$C_4H_9SO_2$ | H | 0.94(t); 1.19(d); 1.22(t); 1.38(m); 1.74(br); 1.91(m); 2.53(m); 3.26(s); 4.45(t); 3.76(d); 4.18(t); 4.62(t); 7.45(s); 7.64(d); 8.16(d). |
| 3.28 | Cl | $SO_2CH_3$ | H | O | H | H | $CH_2$ | i-$C_4H_9$ | i-$C_4H_9SO_2$ | H | 0.96(d); 1.21(d); 2.33(m); 2.51(m); 3.75(d); 3.99(d); 4.61(t); 7.45(s); 7.66(d); 8.17(d). |
| 3.29 | Cl | $SO_2CH_3$ | H | O | H | H | $CH_2$ | i-$C_4H_9$ | $C_2H_5SO_2$ | H | 0.97(d); 1.66(t); 2.36(m); 3.29(s); 3.43(t); 3.82(q); 3.99(d); 4.60(t); 7.47(s); 7.68(d); 8.18(d). |
| 3.30 | Cl | $SO_2CH_3$ | H | O | H | H | $CH_2$ | $CH_3$ | $C_2H_5SO_2$ | H | 1.68(t); 3.29(s); 3.43(t); 3.78(q); 3.92(s); 3.63(t); 7.46(s); 7.62(d); 8.17(d). |
| 3.31 | Cl | $SO_2CH_3$ | H | O | H | H | $CH_2$ | $CH_3$ | i-$C_4H_9SO_2$ | H | 1.23(d); 2.53(m), 3.28(s); 3.43(t); 3.70(d); 3.91(s); 4.61(t); 7.48(s); 7.66(d); 8.18(d). |
| 3.32 | Cl | Cl | H | O | H | H | $CH_2$ | n-$C_3H_7$ | H | H | 119-121 |
| 3.33 | Cl | Cl | H | O | H | H | $CH_2$ | $CH_3$ | H | $CH_3$ | 115-117 |
| 3.34 | Cl | $NO_2$ | H | O | H | H | $CH_2$ | $C_2H_5$ | H | H | 217-218 |
| 3.35 | Cl | $SO_2CH_3$ | H | O | H | H | $CH_2$ | $CH_3$ | H | H | >250 |
| 3.36 | Cl | Cl | H | O | H | H | $CH_2$ | $C_2H_5$ | H | H | 125-128 |
| 3.37 | Cl | $SO_2CH_3$ | H | O | H | H | $CH_2$ | $C_2H_5$ | n-$C_3H_7SO_2$ | H | 78-83 |
| 3.38 | Cl | $SO_2CH_3$ | H | O | H | H | $CH_2$ | $C_2H_5$ | $C_2H_5SO_2$ | H | 1.52(t); 1.68(t); 3.29(s); 3.43(t); 3.82(q); 4.24(q); |

TABLE 3-continued

I

![Structure with R18, R1, R2, R3, R16, R4, R5, X, Y, Z substituents on pyrazole-benzoyl-oxazoline framework]

| No. | R¹ | R² | R³ | X | R⁴ | R⁵ | Y | R¹⁶ | Z | R¹⁸ | Physical data m.p. [° C.]; ¹H NMR [δ in ppm] |
|---|---|---|---|---|---|---|---|---|---|---|---|
| 3.39 | Cl | SO₂C₂H₅ | H | O | CH₃ | CH₃ | CH₂ | CH₃ | H | H | 4.63(t); 7.48(s); 7.65(d); 8.07(d). >200 |
| 3.40 | Cl | SO₂C₂H₅ | H | O | CH₃ | H | CH₂ | CH₃ | H | H | 220-223 |
| 3.41 | Cl | SO₂C₂H₅ | H | O | CH₃ | H | CH₂ | C₂H₅ | H | H | >230 |
| 3.42 | Cl | SO₂-n-C₃H₇ | H | O | CH₃ | H | CH₂ | CH₃ | H | H | 1.12(t); 1.53(d); 1.76(quin); 3.18(dd); 3.38(t); 3.55(dd); 3.73(s); 5.04(m); 5.55(s, br.); 7.37(s); 7.68(d); 8.13(d). |
| 3.43 | Cl | SO₂-n-C₃H₇ | H | O | CH₃ | H | CH₂ | C₂H₅ | H | H | 1.07(t); 1.50(m); 1.78(quin) 3.07(dd); 3.39(t); 3.55(dd); 4.12(t); 5.08(m); 7.38(s); 7.69(d); 8.11(d). |
| 3.44 | Cl | SO₂CH₃ | H | CH₂ | H | H | O | CH₃ | H | H | |
| 3.45ᵃ⁾ | Cl | SO₂CH₃ | H | C(CH₃)₂ | H | H | O | CH₃ | H | H | 1.33(s); 3.40(s); 4.17(s); 7.43(s); 7.79(d); 8.04(d). |
| 3.46 | Cl | SO₂CH₃ | H | O | H | H | CH₂ | C₂H₅ | Na⁺ | H | 218-220 |
| 3.47 | Cl | SO₂CH₃ | H | O | H | H | CH₂ | C₂H₅ | K⁺ | H | 193 |
| 3.48 | Cl | SO₂CH₃ | H | O | H | H | CH₂ | C₂H₅ | Li⁺ | H | >230 |
| 3.49 | Cl | SO₂CH₃ | H | O | H | H | CH₂ | C₂H₅ | NH₄⁺ | H | 170-175 |
| 3.50 | Cl | SO₂CH₃ | H | O | H | H | CH₂ | CH₃ | Na⁺ | H | >240 |
| 3.51 | Cl | SO₂CH₃ | H | O | H | H | CH₂ | CH₃ | K⁺ | H | 206-214 |
| 3.52 | Cl | SO₂CH₃ | H | O | H | H | CH₂ | CH₃ | Li⁺ | H | >240 |
| 3.53 | Cl | SO₂CH₃ | H | O | H | H | CH₂ | CH₃ | NH₄⁺ | H | |
| 3.54ᵃ⁾ | Cl | SO₂CH₃ | H | C(CH₃)₂ | H | H | O | C₂H₅ | H | H | 1.27(t); 1.36(s); 3.41(q); 4.01(q); 4.18(s); 7.47(s); 7.83(d); 8.07(d). |
| 3.55 | Cl | SO₂CH₃ | H | O | H | —(CH₂)₃CH— | CH₂ | C₂H₅ | H | H | 99-104 |
| 3.56 | Cl | SO₂CH₃ | H | O | H | —(CH₂)₃CH— | CH₂ | CH₃ | H | H | 95-100 |
| 3.57 | Cl | SO₂CH₃ | H | O | —(CH₂)₄— | | CH₂ | CH₃ | H | H | 230-235 |
| 3.58 | Cl | SO₂CH₃ | H | O | —(CH₂)₄— | | CH₂ | C₂H₅ | H | H | 190-195 |
| 3.59 | Cl | SO₂CH₃ | H | O | —(CH₂)₂O(CH₂)₂— | | CH₂ | C₂H₅ | H | H | 95-100 |
| 3.60 | Cl | SO₂C₂H₅ | H | O | CH₃ | CH₃ | CH₂ | CH₃ | H | H | <230 |
| 3.61 | Cl | SO₂C₂H₅ | H | O | CH₃ | CH₃ | CH₂ | C₂H₅ | H | H | 198-200 |
| 3.62 | Cl | SO₂C₂H₅ | H | O | H | H | CH₂ | CH₃ | H | H | 215-218 |
| 3.63 | Cl | SO₂C₂H₅ | H | O | H | H | CH₂ | C₂H₅ | H | H | 213-215 |
| 3.64 | Cl | SO₂-n-C₃H₇ | H | O | H | H | CH₂ | CH₃ | H | H | 186-190 |
| 3.65 | Cl | SO₂-n-C₃H₇ | H | O | H | H | CH₂ | C₂H₅ | H | H | 84-86 |
| 3.66 | Cl | SO₂CH₃ | H | O | —(CH₂)₂O(CH₂)₂— | | CH₂ | CH₃ | H | H | 90-95 |
| 3.67 | Cl | SO₂CH₃ | H | O | C₂H₅ | C₂H₅ | CH₂ | CH₃ | H | H | 70-75 |
| 3.68 | Cl | SO₂CH₃ | H | O | C₂H₅ | C₂H₅ | CH₂ | C₂H₅ | H | H | 50-55 |
| 3.69 | Cl | SO₂CH₃ | H | O | OCH₃ | H | CH₂ | CH₃ | H | H | 3.18-3.99(11H); 5.78(1H); 7.50(1H); 7.81(1H); 8.09(1H). |
| 3.70 | Cl | SO₂CH₃ | H | O | CH₃ | H | CHCH₂Cl | CH₃ | H | H | 1.52(3H); 3.30-4.12(8H); 4.36(1H); 4.93(1H); 7.49(1H); 7.81(1H); |

TABLE 3-continued

| No. | R¹ | R² | R³ | X | R⁴ | R⁵ | Y | R¹⁶ | Z | R¹⁸ | Physical data m.p. [° C.]; ¹H NMR [δ in ppm] |
|---|---|---|---|---|---|---|---|---|---|---|---|
| 3.71 | Cl | SO₂CH₃ | H | O | CH₃ | H | CHCH₂Cl | C₂H₅ | H | H | 8.09(1H). 1.27(3H); 1.55(3H); 3.28-4.02(7H) 4.37(1H); 4.92(1H); 7.48(1H); 7.80(1H); 8.07(1H) |
| 3.72 | Cl | SO₂CH₃ | H | C(CH₃)₂ | H | H | O | CH₃ | H | H | 132-135 |
| 3.73 | Cl | SO₂CH₃ | H | O | C₂H₅ | H | CH₂ | CH₃ | H | H | 95-100 |
| 3.74 | Cl | SO₂CH₃ | H | O | C₂H₅ | H | CH₂ | C₂H₅ | H | H | 1.16(3H); 1.27(3H); 3.20-4.00(9H); 5.89(1H); 7.50(1H); 7.82(1H); 8.07(1H). |
| 3.75 | Cl | SO₂CH₃ | H | O | C₂H₅ | C₂H₅ | CH₂ | C₂H₅ | K⁺ | H | 200-205 |
| 3.76 | Cl | SO₂C₂H₅ | H | C(CH₃)₂ | H | H | O | CH₃ | H | H | 120-123 |
| 3.77 | Cl | SO₂-n-C₃H₇ | H | O | CH₃ | CH₃ | CH₂ | C₂H₅ | H | H | 152-158 |
| 3.78 | Cl | SO₂-n-C₃H₇ | H | O | CH₃ | CH₃ | CH₂ | CH₃ | H | H | 172-176 |
| 3.79 | Cl | SO₂-n-C₃H₇ | H | O | CH₃ | H | CH₂ | CH₃ | H | H | 188-205 |
| 3.80 | Cl | SCH₃ | H | O | H | H | CH₂ | C₂H₅ | H | H | 1.29(t); 2.56(s); 3.28(t); 3.93(q); 4.49(t); 7.40(s); 7.43(d); 7.55(d). |
| 3.81 | Cl | SO₂CH₃ | H | O | CH₂Cl | H | CH₂ | C₂H₅ | H | H | 78-82 |
| 3.82 | CH₃ | H | H | CH₂ | H | H | S | C₂H₅ | H | H | 1.44(t); 2.50(s); 3.49(t); 4.09(q); 4.53(t); 7.35(m); 7.48(d); 7.62(d). |
| 3.83 | Cl | SO₂CH₃ | H | O | CH₂Cl | H | CH₂ | CH₃ | H | H | 81-85 |
| 3.84 | Cl | SCH₃ | H | O | H | H | CH₂ | CH₃ | H | H | 151-153 |
| 3.85 | Cl | SOCH₃ | H | O | H | H | CH₂ | C₂H₅ | H | H | 1.28(t); 2.82(s); 3.40(m); 3.92(m); 4.52(t); 7.45(s); 7.82(d); 8.10(d). |
| 3.86 | CH₃ | SO₂CH₃ | H | O | H | H | CH₂ | CH₃ | H | H | 205-210 |
| 3.87 | Cl | Cl | H | CH₂ | H | H | S | C₂H₅ | H | H | 173-179 |
| 3.88 | Cl | SCH₃ | H | CH₂ | H | H | S | C₂H₅ | H | H | 1.43(t); 2.51(s); 3.59(t); 4.08(q); 4.51(t); 7.22(d); 7.41(s); 7.50(d). |
| 3.89 | Cl | SO₂CH₃ | H | CH₂ | H | H | S | C₂H₅ | H | H | 1.50(t); 3.28(s); 3.62(t); 4.10(q); 4.49(t); 7.36(s); 7.68(d); 8.19(d). |
| 3.90 | CH₃ | SO₂CH₃ | H | O | H | H | CH₂ | C₂H₅ | H | H | 174-180 |
| 3.91 | Cl | SO₂CH₃ | H | O | CH₂Cl | H | CH₂ | CH₃ | H | H | 77-83 |
| 3.92 | Cl | SO₂CH₃ | H | O | F | H | CH₂ | CH₃ | H | H | |
| 3.93 | Cl | SO₂CH₃ | H | O | F | H | CH₂ | C₂H₅ | H | H | |
| 3.94 | Cl | SO₂CH₃ | H | O | F | F | CH₂ | CH₃ | H | H | |
| 3.95 | Cl | SO₂CH₃ | H | O | F | F | CH₂ | C₂H₅ | H | H | |
| 3.96 | Cl | SO₂CH₃ | H | O | CH₃ | H | CHCH₃ | C₂H₅ | H | H | 183-184 |
| 3.97 | Cl | SO₂CH₃ | H | O | CF₃ | H | CH₂ | CH₃ | H | H | 223-225 |
| 3.98 | Cl | SO₂CH₃ | H | O | CF₃ | H | CH₂ | C₂H₅ | H | H | 183-184 |
| 3.99 | Cl | SO₂CH₃ | H | O | SC₂H₅ | H | CH₂ | CH₃ | H | H | 195-196 |
| 3.100 | Cl | SO₂CH₃ | H | O | SC₂H₅ | H | CH₂ | C₂H₅ | H | H | 199-200 |
| 3.101 | Cl | SO₂CH₃ | H | O | CH₃ | H | CHCH₃ | CH₃ | H | H | 230-233 |

TABLE 3-continued

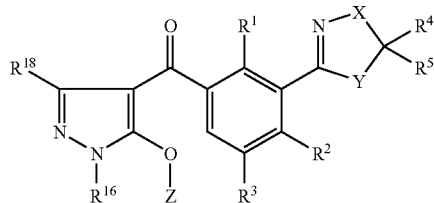

| No. | R¹ | R² | R³ | X | R⁴ | R⁵ | Y | R¹⁶ | Z | R¹⁸ | Physical data m.p. [° C.]; $^1$H NMR [δ in ppm] |
|---|---|---|---|---|---|---|---|---|---|---|---|
| 3.102 | Cl | SO₂CH₃ | H | O | CHCl(CH₃) | H | CH₂ | C₂H₅ | H | H | 102-107 |
| 3.103 | Cl | SO₂CH₃ | H | O | CHCl(CH₃) | H | CH₂ | CH₃ | H | H | 80-85 |
| 3.104 | Cl | SO₂CH₃ | H | O | n-C₃H₇ | H | CH₂ | CH₃ | H | H | |
| 3.105 | Cl | SO₂CH₃ | H | O | n-C₃H₇ | H | CH₂ | C₂H₅ | H | H | |
| 3.106 | Cl | SO₂CH₃ | H | O | H | H | CH₂ | CH₃ | ⁺NH₂(CH₃)₂ | H | 200 |
| 3.107 | Cl | SO₂CH₃ | H | O | H | H | CH₂ | CH₃ | ⁺NH₂(CH₂CH₂OH) | H | 187 |
| 3.108 | Cl | SO₂CH₃ | H | O | H | H | CH₂ | CH₃ | ⁺NH₃(CH₂CH₂OCH₂CH₂OH) | H | 180 |
| 3.109 | SCH₃ | SCH₃ | H | O | H | H | CH₂ | CH₃ | H | H | 2.33(s); 2.51(s); 3.40(t); 3.70(s); 4.58(t); 5.15(brs); 7.21(s); 7.31(d); 7.42(d) |
| 3.110 | SCH₃ | SCH₃ | H | O | H | H | CH₂ | C₂H₅ | H | H | 1.38(t); 2.33(s); 2.49(s); 3.41(t); 4.10(q); 4.58(t); 7.25(s); 7.32(d); 7.41(d); 7.82(brs). |
| 3.111 | SO₂CH₃ | SO₂CH₃ | H | O | H | H | CH₂ | CH₃ | H | H | oil |
| 3.112 | SO₂CH₃ | SO₂CH₃ | H | O | H | H | CH₂ | C₂H₅ | H | H | oil |

*a)*Prepared from 2-chloro-3-(1'-chloro-2',2'-dimethylethylaminocarbonyl)-4-methylsulfonylbenzoyl chloride with two equivalents of potassium carbonate.

The syntheses of some starting materials are given below:

2-Chloro-3-(4,5-dihydroisoxazol-3-yl)-4-methylsulfonylbenzoyl chloride (compound 4.5)

Step a) 2-Chloro-3-methyl-4-methylthioacetophenone

A solution of 157 g (2 mol) of acetyl chloride in 420 mol of 1,2-dichlorethane was added dropwise to a suspension of 286 g (2.14 mol) of aluminum trichloride in 420 ml of 1,2-dichloroethane at 15-20° C. A solution of 346 g (2 mol) of 2-chloro-6-methylthiotoluene in 1 l of 1,2-dichlorethane was subsequently added dropwise. After the reaction mixture had been stirred for 12 hours, it was poured into a mixture of 3 l of ice and 1 l of concentrated HCl. The mixture was extracted with methylene chloride, and the organic phase was washed with water, dried with sodium sulfate and concentrated. The residue was distilled in vacuo. This gave 256 g (60% of theory) of 2-chloro-3-methyl-4-methylthioacetophenone.

(m.p.: 46° C.)

Step b) 2-Chloro-3-methyl-4-methylsulfonylacetophenone 163.0 g (0.76 mol) of 2-chloro-3-methyl-4-methylthioacetophenone were dissolved in 1.5 l of glacial acetic acid, 18.6 g of sodium tungstate were added, and 173.3 g of a 30% strength hydrogen peroxide solution were added dropwise with cooling. Stirring was continued for 2 days and the mixture was subsequently diluted with water. The solid which had precipitated was filtered off with suction, washed with water and dried. This gave 164.0 g (88% of theory) of 2-chloro-3-methyl-4-methylsulfonyl-acetophenone.

(m.p.: 110-111° C.)

Step c) 2-Chloro-3-methyl-4-methylsulfonylbenzoic acid 82 g (0.33 mol) of 2-chloro-3-methyl-4-methyl-sulfonylacetophenone were dissolved in 700 ml of dioxane, and 1 l of a 12.5% strength sodium hypochlorite solution was added at room temperature. Stirring was continued for 1 hour at 80° C. After cooling, two phases formed, of which the bottom phase was diluted with water and acidifed weakly. The solid which had precipitated was filtered off with suction, washed with water and dried. This gave 60 g (73% of theory) of 2-chloro-3-methyl-4-methylsulfonylbenzoic acid.

(m.p.: 230-231° C.)

Step d) Methyl 2-chloro-3-methyl-4-methylsulfonylbenzoate 100 g (0.4 mol) of 2-chloro-3-methyl-4-methyl-sulfonylbenzoic acid were dissolved in 1 l of methanol and hydrogen chloride gas was passed in for 5 hours at reflux temperature. The mixture was subsequently concentrated. This gave 88.5 g (84% of theory) of methyl 2-chloro-3-methyl-4-methylsulfonylbenzoate.

(m.p.: 107-108° C.)

Step e) Methyl 3-bromomethyl-2-chloro-4-methylsulfonyl-benzoate 82 g (0.1 mol) of methyl 2-chloro-3-methyl-4-methyl-sulfonylbenzoate are dissolved in 2 l of tetrachloromethane, and 56 g (0.31 mol) of N-bromosuccinimide are added in portions with exposure to light. The reaction mixture was filtered, the filtrate was concentrated, and the residue was taken up in 200 ml of methyl tert-butyl ether. The solution was treated with petroleum ether and the solid which had precipitated was filtered off with suction and dried. This gave 74.5 g (70% of theory) of methyl 3-bromomethyl-2-chloro-4-methylsulfonylbenzoate.

(m.p.: 74-75° C.)

Step f) Methyl 2-chloro-3-formyl-4-methylsulfonylbenzoate

A solution of 41.0 g (0.12 mol) of methyl 3-bromomethyl-2-chloro-4-methylsulfonylbenzoate in 250 ml of acetonitrile was treated with 42.1 g (0.36 mol) of N-methylmorphline N-oxide. The batch was stirred for 12 hours at room temperature and subsequently concentrated, and the residue was taken up in ethyl acetate. The solution was extracted with water, dried with sodium sulfate and concentrated. This gave 31.2 g (94% of theory) of methyl 2-chloro-3-formyl-4-methylsulfonylbenzoate (m.p.: 98-105° C.)

Step g) 2-Chloro-3-hydroxyiminomethyl-4-methylsulfonyl-benzoic acid 15.00 g (54 mmol) of methyl 2-chloro-3-formyl-4-methylsulfonylbenzoate and 4,20 g (60 mmol) of hydroxylamine hydrochloride were taken up in 300 ml of methanol, and a solution of 3.18 g (30 mmol) of sodium carbonate in 80 ml of water was added dropwise. After the mixture had been stirred for 12 hours at room temperature, the methanol was distilled off, the residue was diluted with water and the mixture was extracted with diethyl ether. After the organic phase had been dried, the solvent was removed. This gave 14.40 g (91% of theory) of methyl 2-chloro-3-hydroxyiminomethyl-4-methylsulfonylbenzoate.

(m.p.: 126-128° C.).

Step h) Methyl 2-chloro-3-(4,5-dihydroisoxazol-3-yl)-4-methylsulfonylbenzoate (compound 4.3)

Ethylene was passed for 30 minutes at 15-20° C. into a solution of 158.0 g (0.54 mol) of methyl 2-chloro-3-hydroxyiminomethyl-4-methylsulfonylbenzoate and 1 l of dichloromethane. After 1.6 g of sodium acetate had been added, 454 ml of sodium hydrochlorite solution were added dropwise at 10° C. while simultaneously passing in ethylene. Ethylene was subsequently passed in at 10° C. for a further 15 minutes. After the mixture had been stirred for 12 hours, the phases were separated, and the organic phase was washed with water, dried and concentrated. This gave 156.5 g (90% of theory) of methyl 2-chloro-(4,5-dihydroisoxazol-3-yl)-4-methylsulfonylbenzoate.

($^1$H NMR (δ in ppm): 3.24 (s); 3.42 (t); 3.99 (s); 4.60 (t); 7.96 (d); 8.10 (d)).

Step i) 2-Chloro-3-(4,5-dihydroisoxazol-3-yl)-4-methylsulfonyl-benzoic acid (compound 4.4)

A solution of 32.8 g of sodium hydroxide, dissolved in 330 ml of methanol, was slowly added dropwise to a mixture of 170.0 g (0.54 mol) of methyl 2-chloro-3-(4,5-dihydroisoxazol-3-yl)-4-methylsulfonylbenzoate and 1 l of methanol at 40-45° C. The suspension was stirred for 5 hours at 50° C. After the solvent had been distilled off, the residue was taken up in 1.5 l of water, and the aqueous phase was extracted three times with ethyl acetate. The aqueous phase was acidified with hydrochloric acid and extracted three times with ethyl acetate. The combined organic phases were subsequently washed to neutrality with water, dried and concentrated. This gave 148.8 g (91% of theory) of 2-chloro-3-(4,5-dihydroisoxazol-3-yl)-4-methylsulfonyl-benzoic acid.

($^1$H NMR (δ in ppm): 3.26 (s); 3.45 (t); 4.63 (t); 8.15 (s) 8.53 (s, br)).

Step j) 2-Chloro-3-(4,5-dihydroisoxazol-3-yl)-4-methylsulfonyl-benzoyl chloride (compound 4.5)

74.8 g (0.63 mol) of thionyl chloride in 50 ml of dry toluene were added dropwise at 50° C. to a solution of 139.0 g of 2-chloro-3-(4,5-dihydroisoxazol-3-yl)-4-methylsulfonylbenzoic acid, 1 ml of dimethylformamide and 1 l of dry toluene. After the mixture had been heated for 6 hours at 110° C., the solvent was distilled off. This gave 2-chloro-3-(4,5-dihydroisoxazol-3-yl)-4-methyl-sulfonylbenzoyl chloride in quantitative yield.

($^1$H NMR (δ in ppm): 3.25 (s); 3.46 (t); 4.62 (t); 8.21 (dd)).

2-Chloro-3-(5-methyl-4,5-dihydroisoxazol-3-yl)-4-methylsulfonyl-benzoyl chloride (compound 4.39)

Step a) Methyl 2-chloro-3-(5-methyl-4,5-dihydroisoxazol-3-yl)-4-methylsulfonylbenzoate (compound 4.25)

Propene was passed for 30 minutes at room temperature into a solution of 15.0 g (52 mmol) of methyl 2-chloro-3-hydroxyiminomethyl-4-methylsulfonylbenzoate and 200 ml of dichloromethane. After 1.6 g of sodium acetate had been added, 42.8 ml of sodium hydrochlorite [sic] solution were added dropwise at room temperature while simultaneously passing in propene. Propene was subsequently passed in for a further 15 minutes at room temperature. After the mixture had been refluxed for 3 hours, it was stirred for 12 hours at room temperature, propene was again passed in for 5 hours under reflux, and the mixture was stirred for a further 12 hours at room temperature. After the phases had been separated, the organic phase was washed with water, dried and concentrated. This gave 15.5 g (89% of theory) of methyl 2-chloro-(5-methyl-4,5-dihydroisoxazol-3-yl)-4-methyl-sulfonylbenzoate.

(m.p.: 130-135° C.)

Step b) 2-Chloro-3-(5-methyl-4,5-dihydroisoxazol-3-yl)-4-methyl-sulfonylbenzoic acid (compound 4.26)

A solution of 3.52 g (88 mmol) of sodium hydroxide, dissolved in 100 ml of methanol, was slowly added dropwise to a mixture of 15.00 g (45 mmol) of methyl 2-chloro-3-(5-methyl-4,5-dihydroisoxazol-3-yl)-4-methyl-sulfonylbenzoate and 200 ml of methanol. The suspension was stirred for 48 hours at room temperature. After the solvent had been distilled off, the residue was taken up in water, and the aqueous phase was washed three times with ethyl acetate. The aqueous phase was acidified with hydrochloric acid and extracted three times with ethyl acetate. The combined organic phases were subsequently washed to neutrality with water, dried and concentrated. This gave 13.20 g (92% of theory) of 2-chloro-3-(5-methyl-4,5-dihydroisoxazol-3-yl)-4-methylsulfonylbenzoic acid.

(m.p.: 173-178° C.)

Step c) 2-Chloro-3-(5-methyl-4,5-dihydroisoxazol-3-yl)-4-methyl-sulfonylbenzoyl chloride (compound 4.39)

5.7 g (51 mmol) of thionyl chloride were added dropwise at room temperature to a solution of 13.0 g (41 mmol) of 2-chloro-3-(5-methyl-4,5-dihydroisoxazol-3-yl)-4-methyl-sulfonylbenzoic acid, 1 ml of dimethylformamide and 250 ml of dry toluene. The mixture was subsequently refluxed until the reaction was complete. After cooling, the solvent was distilled off. This gave 14.2 g of 2-chloro-3-(5-methyl-4,5-dihydroisoxazol-3-yl)-4-methyl-benzoyl chloride in quantitative yield.

2-Chloro-3-(1'-chloro-2',2'-dimethylethylaminocarbonyl)-4-methyl-sulfonylbenzoyl chloride Step a) Methyl 2-chloro-3-hydroxycarbonyl-4-methyl-sulfonylbenzoate 13.8 g (0.11 mol) of sodium hydrogen phosphate monohydrate in 170 ml of water, 49.3 g (0.43 mol) of 30% strength hydrogen peroxide solution and 66.2 g (0.59 mol) of 80% strength aqueous sodium chlorite solution were added in succession at 5° C. to a solution of 115.3 g (0.42 mol) of methyl 2-chloro-3-formyl-4-methyl-sulfonylbenzoate and [sic] 2000 ml of acetonitrile. The reaction solution was subsequently stirred for 1 hour at 5° C. and for 12 hours at room temperature. The pH was then brought to 1 with 10% strength hydrochloric acid, and 1500 ml of aqueous 40% strength sodium hydrogen sulfite solution were added. After the mixture had been stirred for 1 hour at room temperature, the aqueous phase was extracted three times with ethyl acetate. The combined organic phases were washed with sodium hydrogen sulfite solution and dried. After the solvent had been distilled off, 102.0 g of methyl 2-chloro-3-hydroxycarbonyl-4-methylsulfonylbenzoate were obtained.

($^1$H NMR ($\delta$ in ppm): 3.34 (s); 3.93 (s); 8.08 (s); 14.50 (s, br.).)

Step b) Methyl 2-chloro-3-chlorocarbonyl-4-methylsulfonylbenzoate 2 drops of dimethylformamide and 11.9 g (0.1 mol) of thionyl chloride were added to a solution of 6.0 g (0.021 mol) of methyl 2-chloro-3-hydroxycarbonyl-4-methylsulfonylbenzoate and 50 ml of dry toluene. The solution was refluxed for 4 hours. After the solvent had been removed in vacuo, 6.2 g of methyl 2-chloro-3-chlorocarbonyl-4-methylsulfonylbenzoate were obtained.

($^1$H NMR ($\delta$ in ppm): 3.21 (s); 4.02 (s); 8.02 (d); 8.07 (d).)

Step c) Methyl 2-chloro-3-(1'-hydroxy-2',2'-dimethylethylaminocarbonyl)-4-methylsulfonylbenzoate A solution of 7.80 g (25 mmol) of methyl 2-chloro-3-chlorocarbonyl-4-methylsulfonylbenzoate was added dropwise at 0-5° C. to a solution of 4.54 g (50 mmol) of 2,2-dimethylethanolamine in 40 ml of dichloromethane. After the reaction solution had been stirred for 6 hours at room temperature, it was extracted three times with water, dried and concentrated. This gave 8.20 g (80% of theory) of methyl 2-chloro-3-(1'-hydroxy-2',2'-dimethylethylaminocarbonyl)-4-methylsulfonylbenzoate. (m.p.: 70-72° C.).

Step d) Methyl 2-chloro-3-(1'-chloro-2',2'-dimethyl-ethylaminocarbonyl)-4-methylsulfonylbenzoate A mixture of 6.9 g (20 mmol) of methyl 2-chloro-3-(1'-hydroxy-2',2'-dimethylethylamino-carbonyl)-4-methylsulfonylbenzoate and 5 ml of thionyl chloride was stirred for 6 hours at room temperature. The solution was diluted with 50 ml of dichloromethane and subsequently concentrated. The residue was dissolved in 20 ml of dichloromethane. The addition of cyclohexane resulted in a crystalline precipitate which was filtered off with suction and dried. This gave 6.4 g (88% of theory) of methyl 2-chloro-3-(1'-chloro-2',2'-dimethylethylaminocarbonyl)-4-methylsulfonylbenzoate.

Step e) 2-Chloro-3-(4',4'-dimethyl-4',5'-dihydroxazol-2-yl)-4-methylsulfonylbenzoic acid (compound 4.38)

A solution of 5.82 g (15 mmol) of methyl 2-chloro-3-(1'-chloro-2',2'-dimethylethyl-aminocarbonyl)-4-methylsulfonylbenzoate and 0.81 g (20 mmol) of sodium hydroxide in 80 ml of methanol was stirred for 8 hours at room temperature. After the solvent had been distilled off, the residue was taken up in water and the mixture was washed three times with ethyl acetate. The aqueous phase was acidified with hydrochloric acid and extracted three times with ethyl acetate. After the organic phase had been dried, the solvent was removed in vacuo. This gave 3.10 g (56% of theory) of 2-chloro-3-(4',4'-dimethyl-4',5'-dihydrooxazol-2-yl)-4-methylsulfonylbenzoic acid.

($^1$H NMR ($\delta$ in ppm): 1.34 (s); 3.40 (s); 4.13 (s); 8.07 (s); 13.95 (s, br)).

Step f) 2-Chloro-3-(1'-chloro-2',2'-dimethylethylaminocarbonyl)-4-methylsulfonylbenzoyl chloride A solution of 3.00 g (9 mmol) of 2-chloro-3-(4',4'-dimethyl-4',5'-dihydrooxazol-2-yl)-4-methylsulfonyl-benzoic acid, 1.43 g of thionyl chloride and 1 drop of dimethylformamide in 80 ml of dry toluene was refluxed for 3 hours. After cooling, the solvent was distilled off in vacuo. This gave 3.43 g (86% of theory) of 2-chloro-3-(1'-chloro-2',2'-dimethylethylaminocarbonyl)-4-methylsulfonylbenzoyl chloride.

Methyl 2-chloro-3-(1,3,4-oxathiazolin-2-on-5-yl)-4-methylsulfonylbenzoate (compound 4.22)

Step a) Methyl 3-aminocarbonyl-2-chloro-4-methylsulfonylbenzoate

Ammonia was passed for 2 hours into a solution of 15.0 g (48 mmol) of methyl 2-chloro-3-chlorocarbonyl-4-methylsulfonylbenzoate and 300 ml of dry dioxane. The precipitate formed was filtered off with suction and the filtrate was concentrated. This gave 15.2 g of methyl 3-aminocarbonyl-2-chloro-4-methylsulfonylbenzoate in quantitative yield.

Step b) Methyl 2-chloro-3-(1,3,4-oxathiazolin-2-on-5-yl)-4-methylsulfonylbenzoate 9.80 g (75 mmol) of chlorocarbonylsulfenyl chloride were added dropwise to a solution of 4.37 g (15 mmol) of methyl 3-aminocarbonyl-2-chloro-4-methylsulfonylbenzoate in 150 ml of dry toluene. After the mixture had been stirred for 48 hours under reflux, the solvent is removed in vacuo and the residue is chromatographed on silica gel (eluent:ethyl acetate/cyclohexane=1/1). This gave 3.70 g (70% of theory) of methyl 2-chloro-3-(1,3,4-oxathiazolin-2-on-5-yl)-4-methylsulfonylbenzoate.

Methyl 2-chloro-4-methylsulfonyl-3-(4,5-dihydrooxazol-3-yl)-benzoate (compound 4.41)

At room temperature, 41.8 g (0.41 mol) of triethylamine and then 31.1 g (0.10 mol) of methyl 2-chloro-3-chlorocarbonyl-4-methylsulfonylbenzoate in 150 ml of toluene were added dropwise to 26.6 g (0.13 mol) of 1-amino-2-bromoethane hydrobromide in 500 ml of toluene. The mixture was heated under reflux for 5 hours and then stirred at room temperature for 12 hours, another 5.0 g (0.02 mol) of 1-amino-2-bromoethane hydrobromide were added and the mixture was heated under reflux for 7.5 hours. The reaction mixture was allowed to cool, diluted with ethyl acetate, washed with water, dried and concentrated. The residue was then recrystallized from methyl tert-butyl ether/ethyl acetate. 14.5 g (46% of theory) of methyl 2-chloro-4-methyl-sulfonyl-3-(4,5-dihydrooxazol-2-yl)benzoate were obtained.

2-Chloro-3-(5-methoxy-5-methyl-4,5-dihydroisoxazol-3-yl)-4-methylsulfonylbenzoic acid (compound 4.60)

Step a) Methyl 2-chloro-3-(5-methoxy-5-methyl-4,5-dihydro-isoxazol-3-yl)-4-methylsulfonylbenzoate 7.3 g (102 mmol) of 2-methoxy-1-propene, 28 ml of sodium hypochlorite solution (12.5% strength) and a spatula-tip of sodium acetate were added successively to 10.0 g (34 mmol) of methyl 2-chloro-3-(hydroxyiminomethyl)-4-methylsulfonylbenzoate in 200 ml of methylene chloride. The mixture was stirred at room temperature for 12 hours, the solvent was removed and the residue was taken up in ethyl acetate, washed with water, dried and concentrated. The residue was chromatographed over silica gel (eluent: cyclohexane:ethyl acetate=3:2). This gave 5.8 g (47% of theory) of methyl 2-chloro-3-(5-methoxy-5-methyl-4,5-dihydroisoxazol-3-yl)-4-methylsulfonylbenzoate.
(mp.: 100-105° C.)

Step b) 2-Chloro-3-(5-methoxy-5-methyl-4,5-dihydroisoxazol-3-yl)-4-methylsulfonylbenzoate At reflux temperature, 5.5 g (15.0 mmol) of methyl 2-chloro-3-(5-methoxy-5-methyl-4,5-dihydroisoxazol-3-yl)-4-methylsulfonylbenzoate in 100 ml of pyridine were added dropwise to 5.0 g (37.5 mmol) of lithium iodide in 200 ml of pyridine. The mixture was stirred at this temperature for 4 hours and then cooled, the solvent was distilled off and the residue was taken up in toluene and reconcentrated. The residue was subsequently admixed with water and washed with methylene chloride, and the pH was adjusted to 1 using hydrochloric acid. The aqueous phase was extracted with methylene chloride and the resulting organic phase was dried and concentrated. This gave 4.7 g (90% of theory) of 2-chloro-(5-methoxy-5-methyl-4,5-di-hydroisoxazol-3-yl)-4-methylsulfonylbenzoate.
(mp.: 40-45° C.)

Methyl 2-chloro-3-(2-methyl-2H-1,3,4-dioxazol-5-yl)-4-methyl-sulfonylbenzoate (compound 4.44)

8.0 g (27.4 mmol) of methyl 2-chloro-3-(hydroxyiminomethyl)-4-methylsulfonylbenzoate in 150 ml of methylene chloride were admixed dropwise with 16.0 g (27.4 mmol) of a 12.5% strength sodium hypochlorite solution, and a spatula-tip of sodium acetate was added. After 1 hour, 34.4 g (0.74 mol) of acetaldehyde were added a little at a time within a period of 36 hours, and the mixture was slowly heated to 55° C. The mixture was subsequently stirred at room temperature for 48 hours, washed with water, dried and concentrated. The residue was then taken up in methylene chloride, 10.0 g (0.23 mol) of acetaldehyde and a spatula-tip of sodium acetate were added and the mixture was heated under reflux for 8 hours. After 72 hours, a further 10.0 g (0.23 mol) of acetaldehyde were added and the mixture was stirred at room temperature. The mixture was subsequently washed with water, dried and concentrated. The residue was passed through silica gel (eluent: isopropanol:cyclohexane=1:9). This gave 5.0 g (55% of theory) of methyl 2-chloro-3-(2-methyl-2H-1,3,4-dioxazol-5-yl)-4-methylsulfonylbenzoate.

Table 4 which follows lists the compounds which have been described above and also further benzoic acid derivatives of the formula III which were prepared, or can be prepared, by a similar method.

TABLE 4

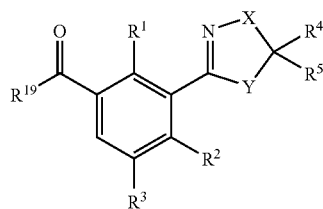

III

| No. | $R^1$ | $R^2$ | $R^3$ | X | $R^4$ | $R^5$ | Y | $R^{19}$ | Physical data m.p. [° C.]; $^1$H NMR [δ in ppm] |
|---|---|---|---|---|---|---|---|---|---|
| 4.1 | Cl | Cl | H | O | H | H | $CH_2$ | $OCH_3$ | 3.29(t); 3.91(s); 4.58(t); 7.46(d); 7.83(d). |
| 4.2 | Cl | Cl | H | O | H | H | $CH_2$ | OH | 3.28(t); 4.60(t); 7.02(s, br); 7.46(d); 7.98(d). |
| 4.3 | Cl | $SO_2CH_3$ | H | O | H | H | $CH_2$ | $OCH_3$ | 3.24(s); 3.42(s); 3.99(s); 4.60(t); 7.96(d); 8.10(d). |
| 4.4 | Cl | $SO_2CH_3$ | H | O | H | H | $CH_2$ | OH | 3.26(s); 3.45(t); 4.63(t); 8.15(s); 8.53(s, br). |
| 4.5 | Cl | $SO_2CH_3$ | H | O | H | H | $CH_2$ | Cl | 3.25(s); 3.46(t); 4.62(t); |

TABLE 4-continued

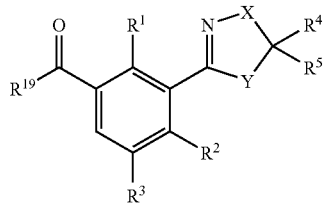

| No. | R¹ | R² | R³ | X | R⁴ | R⁵ | Y | R¹⁹ | Physical data m.p. [° C.]; ¹H NMR [δ in ppm] |
|---|---|---|---|---|---|---|---|---|---|
| 4.6 | Cl | Cl | H | C(CH$_3$)$_2$ | H | H | O | OH | 8.21(dd). 1.31(s); 4.16(s); 7.69(d); 7.90(d); 13.8(s, br). |
| 4.7 | Cl | SO$_2$C$_2$H$_5$ | H | O | CH$_3$ | CH$_3$ | CH$_2$ | OCH$_3$ | 1.25(t); 1.57(s); 3.21(s); 3.42(q); 3.99(s); 7.94(d); 8.07(d). |
| 4.8 | Cl | SO$_2$C$_2$H$_5$ | H | O | CH$_3$ | CH$_3$ | CH$_2$ | OH | 1.13(t); 1.47(s); 3.15(s); 3.43(q); 8.06(s); 13.8(s, br). |
| 4.9 | Cl | SO$_2$C$_2$H$_5$ | H | O | H | H | CH$_2$ | OCH$_3$ | 1.28(t); 3.41(m); 4.02(s); 4.62(t); 7.95(d); 8.06(d). |
| 4.10 | Cl | SO$_2$C$_2$H$_5$ | H | O | H | H | CH$_2$ | OH | 137-140 |
| 4.11 | Cl | SO$_2$C$_2$H$_5$ | H | O | CH$_3$ | H | CH$_2$ | OCH$_3$ | 1.26(t); 1.53(d); 3.06(dd); 3.42(q); 3.49(dd); 5.05(m); 7.95(d); 8.07(d). |
| 4.12 | Cl | SO$_2$C$_2$H$_5$ | H | O | CH$_3$ | H | CH$_2$ | OH | 140-143 |
| 4.13 | Cl | SO$_2$CH$_3$ | H | CH$_2$ | H | H | O | OCH$_3$ | 3.30(s); 3.98(s); 4.11(t); 4.55(t); 7.97(d); 8.08(d). |
| 4.14 | Cl | SO$_2$CH$_3$ | H | CH$_2$ | H | H | O | OH | 3.38(s); 4.00(t); 4.46(t); 8.08(s). |
| 4.15 | Cl | SO$_2$CH$_3$ | H | O | H | H | CH$_2$ | OH | 3.30(s); 3.35(t); 4.15(s, br); 4.50(t); 8.05(s). |
| 4.16 | Cl | SO$_2$-n-C$_3$H$_7$ | H | O | CH$_3$ | CH$_3$ | CH$_2$ | OCH$_3$ | 0.95(t); 1.47(s); 1.58(quin); 3.12(s); 3.31(s); 3.43(t); 3.93(s); 8.09(dd). |
| 4.17 | Cl | SO$_2$-n-C$_3$H$_7$ | H | O | CH$_3$ | CH$_3$ | CH$_2$ | OH | 0.93(t); 1.47(s); 1.58(quin); 3.15(s); 3.42(t); 8.05(s). |
| 4.18 | Cl | SO$_2$-n-C$_3$H$_7$ | H | O | H | H | CH$_2$ | OCH$_3$ | 0.92(t); 1.55(quin); 3.39(m); 3.93(s); 4.50(t); 8.08(dd). |
| 4.19 | Cl | SO$_2$-n-C$_3$H$_7$ | H | O | H | H | CH$_2$ | OH | 148-150 |
| 4.20 | Cl | SO$_2$-n-C$_3$H$_7$ | H | O | CH$_3$ | H | CH$_2$OCH$_3$ | 0.93 | (t); 1.49(d); 1.58(quin); 2.94(dd); 3.42(m); 3.93(s); 4.97(m); 8.10(dd). |
| 4.21 | Cl | SO$_2$-n-C$_3$H$_7$ | H | O | CH$_3$ | H | CH$_2$ | OH | 0.94(t); 1.39(d); 1.58(quin); 2.96(dd); 3.50(m); 4.95(m); 8.05(s). |
| 4.22 | Cl | SO$_2$CH$_3$ | H | S | =O | | O | OCH$_3$ | 3.24(s); 4.02(s); 8.14(dd). |
| 4.23 | Cl | SO$_2$CH$_3$ | H | O | COOC$_2$H$_5$ | H | CH$_2$ | OCH$_3$ | 118-121 |
| 4.24 | Cl | SO$_2$CH$_3$ | H | O | COOC$_2$H$_5$ | H | CH$_2$ | OH | |
| 4.25 | Cl | SO$_2$CH$_3$ | H | O | CH$_3$ | H | CH$_2$ | OCH$_3$ | 130-135 |
| 4.26 | Cl | SO$_2$CH$_3$ | H | O | CH$_3$ | H | CH$_2$ | OH | 173-178 |
| 4.27 | Cl | SO$_2$CH$_3$ | H | O | CH$_3$ | CH$_3$ | CH$_2$ | OCH$_3$ | 1.57(s); 3.18(s); 3.27(s); 4.01(s); 7.97(d); 8.12(d). |
| 4.28 | Cl | SO$_2$CH$_3$ | H | O | CH$_3$ | CH$_3$ | CH$_2$ | OH | 1.48(s); 3.15(s); 3.34(s); 8.08(dd). |
| 4.29 | Cl | SO$_2$CH$_3$ | H | O | C$_2$H$_5$ | H | CH$_2$ | OCH$_3$ | 0.97(t); 1.72(m); 3.10(dd); 3.32(s); 3.37(dd); 4.72(m); 8.08(dd). |
| 4.30 | Cl | SO$_2$CH$_3$ | H | O | H | —(CH$_2$)$_3$—CH— | | OCH$_3$ | 1.57(m); 1.81(m); 2.21(m); 3.20(s); 4.02(s); 4.32(t); 5.35(dd); 7.92(d); 8.18(d). |
| 4.31 | Cl | SO$_2$CH$_3$ | H | O | H | —(CH$_2$)$_3$—CH— | | OH | 1.72(m); 2.01(m); 3.27(s); 4.24(t); 5.23(dd); 8.05(d); 8.15(d); 13.8(s, br). |
| 4.32 | Cl | SO$_2$CH$_3$ | H | O | —(CH$_2$)$_2$—O—(CH$_2$)$_2$— | | CH$_2$ | OCH$_3$ | 2.00(m); 3.23(s); 3.27(s), 3.72(m); 4.00(s); 7.96(d); 8.04(d). |
| 4.33 | Cl | SO$_2$CH$_3$ | H | O | —(CH$_2$)$_2$—O—(CH$_2$)$_2$— | | OH | | 78-83 |
| 4.34 | Cl | SO$_2$CH$_3$ | H | O | —(CH$_2$)$_4$— | | CH$_2$ | OCH$_3$ | 1.78(m); 2.24(m); 3.27(s); 3.36(s); 3.98(s); 7.94(d); 8.12(d). |
| 4.35 | Cl | SO$_2$CH$_3$ | H | O | —(CH$_2$)$_4$— | | CH$_2$ | OH | 1.76(m); 2.05(m); 3.30(s); 3.33(s); 8.09(dd). |

TABLE 4-continued

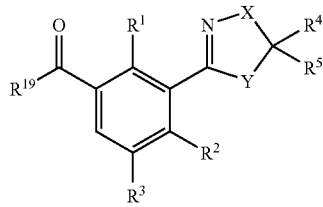

| No. | R¹ | R² | R³ | X | R⁴ | R⁵ | Y | R¹⁹ | Physical data m.p. [° C.]; ¹H NMR [δ in ppm] |
|---|---|---|---|---|---|---|---|---|---|
| 4.36 | Cl | SO₂CH₃ | H | O | C₂H₅ | C₂H₅ | CH₂ | OCH₃ | 1.00(t); 1.85(m); 3.13(s); 3.27(s); 3.98(s); 7.94(d); 8.11(d) |
| 4.37 | Cl | SO₂CH₃ | H | O | C₂H₅ | C₂H₅ | CH₂ | OH | 0.91(t); 1.76(m); 3.12(s); 3.33(s); 8.07(dd); 13.75(s, br). |
| 4.38 | Cl | SO₂CH₃ | H | C(CH₃)₂ | H | H | O | OH | 1.34(s); 3.40(s); 4.13(s); 8.07(s); 13.95(s, br). |
| 4.39 | Cl | SO₂CH₃ | H | O | CH₃ | H | CH₂ | Cl | |
| 4.40 | Cl | SO₂CH₃ | H | CH₂ | H | H | O | OH | >260 |
| 4.41 | Cl | SO₂CH₃ | H | CH₂ | H | H | O | OCH₃ | 3.29(3H); 3.96(3H); 4.12(2H); 4.55(2H); 7.98(1H); 8.09(1H). |
| 4.42 | Cl | SCH₃ | H | O | H | H | CH₂ | OCH₃ | 202-203 |
| 4.43 | Cl | SO₂CH₃ | H | O | COOMe | H | CHCO₂CH₃ | OCH₃ | 1.05(3H); 1.35(3H); 3.19(3H); 4.01(3H); 4.09(2H); 4.35(2H); 5.06(1H); 5.77(1H); 8.08(1H); 8.17(1H). |
| 4.44 | Cl | SO₂CH₃ | H | O | CH₃ | H | O | OCH₃ | 1.78(3H); 3.30(3H); 3.98(3H); 6.40(1H); 8.08(1H); 8.15(1H). |
| 4.45 | Cl | SO₂CH₃ | H | O | CHO | H | CHCH₃ | OCH₃ | 80-85 |
| 4.46 | Cl | SO₂CH₃ | H | O | CH₃ | H | CHCH₂Cl | OCH₃ | 1.65(3H); 3.27(3H); 3.50(2H); 4.00(3H); 4.22(1H); 4.88/5.08 (1H); 7.99(1H); 8.12(1H). |
| 4.47 | Cl | SO₂CH₃ | H | O | CH₃ | H | CHCH₂Cl | OH | 100-105 |
| 4.48 | Cl | SO₂CH₃ | H | O | CHO | H | CHCH₃ | OH | 180-185 |
| 4.49 | Cl | SO₂CH₃ | H | O | SC₂H₅ | H | CH₂ | OCH₃ | 1.30(3H); 2.75(2H); 3.25(1H); 3.34(3H); 3.78(1H); 3.94(3H); 6.22(1H); 8.15(2H). |
| 4.50 | Cl | SO₂CH₃ | H | O | SC₂H₅ | H | CH₂ | OH | 65-67 |
| 4.51 | Cl | SO₂CH₃ | H | O | CH₃ | H | CHCH₃ | OCH₃ | 1.01(3H); 1.28(3H); 3.33(4H); 3.96(3H); 4.98(1H); 8.12(1H); 8.20(1H). |
| 4.52 | Cl | SO₂CH₃ | H | O | CH₃ | H | CHCH₃ | OH | 68-75 |
| 4.53 | Cl | SO₂CH₃ | H | O | OCOCH₃ | H | CH₂ | OCH₃ | 105-110 |
| 4.54 | Cl | SO₂CH₃ | H | O | H | H | CH₂ | OH | |
| 4.55 | Cl | SO₂CH₃ | H | O | OCOCH₃ | H | CH₂ | OH | 45-50 |
| 4.56 | Cl | SO₂CH₃ | H | O | OCH₃ | H | CH₂ | OH | 60-65 |
| 4.57 | Cl | SO₂CH₃ | H | O | CHCl(CH₃) | H | CH₂ | OCH₃ | 1.63(3H); 3.23(3H); 3.50(2H); 3.99(3H); 4.25(1H); 4.83/5.03 (1H); 7.96(1H); 8.13(1H). |
| 4.58 | Cl | SO₂CH₃ | H | O | CHCl(CH₃) | H | CH₂ | OH | 1.56(3H); 3.33(3H); 3.43(2H); 4.36(1H); 4.93(1H); 8.10(2H). |
| 4.59 | Cl | SO₂CH₃ | H | O | CH₃ | OCH₃ | CH₂ | OCH₃ | 100-105 |
| 4.60 | Cl | SO₂CH₃ | H | O | CH₃ | OCH₃ | CH₂ | OH | 40-45 |
| 4.61 | Cl | SO₂CH₃ | H | O | CF₃ | OCOCH₃ | CH₂ | OCH₃ | 60-65 |
| 4.62 | Cl | SCH₃ | H | O | H | H | CH₂ | OH | |
| 4.63 | Cl | SO2Me | H | O | COCH₃ | H | CH₂ | OCH₃ | 2.36(3H); 3.25(3H); 3.66(2H); 4.01(3H); 5.20(1H); 8.01(1H); 8.12(1H). |
| 4.64 | Cl | SO₂CH₃ | H | O | CF₃ | H | CH₂ | OCH₃ | 156 |
| 4.65 | Cl | SO₂CH₃ | H | O | CF₃ | H | CH₂ | OH | 170 |
| 4.66 | Cl | SO₂CH₃ | H | O | F | F | CH₂ | OCH₃ | |
| 4.67 | Cl | SO₂CH₃ | H | O | F | F | CH₂ | OH | |
| 4.68 | Cl | SO₂CH₃ | H | O | F | H | CH₂ | OCH₃ | 142-143 |
| 4.69 | Cl | SO₂CH₃ | H | O | F | H | CH₂ | OH | |
| 4.70 | Cl | SO₂CH₃ | H | O | CH₂Cl | H | CH₂ | OCH₃ | 107-110 |
| 4.71 | Cl | SO₂CH₃ | H | O | CH₂Cl | H | CH₂ | OH | 60-65 |
| 4.72 | Cl | SO₂CH₃ | H | O | OCH₃ | H | CH₂ | OCH₃ | 105-110 |
| 4.73 | Cl | SO₂CH₃ | H | O | OC₂H₅ | H | CH₂ | OCH₃ | 155-160 |
| 4.74 | Cl | SO₂CH₃ | H | CH₂ | H | H | S | OCH₃ | |
| 4.75 | CH₃ | H | H | C=O | H | H | S | OCH₃ | 112-120 |
| 4.76 | Cl | SO₂CH₃ | H | O | CF₃ | OH | CH₂ | OH | 3.38(s); 3.56(d); 3.79(d); 8.16(s); 8.67(s, br). |

TABLE 4-continued

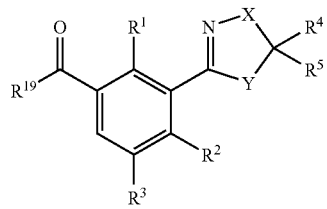

| No. | $R^1$ | $R^2$ | $R^3$ | X | $R^4$ | $R^5$ | Y | $R^{19}$ | Physical data m.p. [° C.]; $^1$H NMR [δ in ppm] |
|---|---|---|---|---|---|---|---|---|---|
| 4.77 | Cl | $SO_2CH_3$ | H | O | O-t-$C_4H_9$ | H | $CH_2$ | $OCH_3$ | 130-135 |
| 4.78 | Cl | $SO_2CH_3$ | H | O | O-t-$C_4H_9$ | H | $CH_2$ | OH | 1.25(s); 3.05(dd); 3.34(s); 3.45(dd); 6.17(m); 8.08(s). |
| 4.79 | Cl | $SO_2CH_3$ | H | O | $CH_3$ | H | $CHCH_3$ | $OCH_3$ | 1.01(d); 1.28(d); 3.35(m); 3.96(s); 4.99(m); 8.12(d); 8.20(d). |
| 4.80 | Cl | $SO_2CH_3$ | H | O | $CH_3$ | H | $CHCH_3$ | OH | 68-75 |
| 4.81 | Cl | $SO_2CH_3$ | H | O | $SC_2H_5$ | H | $CH_2$ | $OCH_3$ | 1.30(t); 2.77(q); 3.25(dd); 3.34(s); 3.78(dd); 3.94(s); 6.22(m), 8.24(s). |
| 4.82 | Cl | $SO_2CH_3$ | H | O | $SC_2H_5$ | H | $CH_2$ | OH | 65-67 |
| 4.83 | $SCH_3$ | $SCH_3$ | H | O | H | H | $CH_2$ | $OCH_2CH_3$ | 1.28(t); 2.30(s); 2.46(s); 3.28(t); 4.31(q); 4.45(t); 7.42(d); 7.68(d). |
| 4.84 | $SCH_3$ | $SCH_3$ | H | O | H | H | $CH_2$ | OH | 2.32(s); 2.48(s); 3.28(t); 4.42(t); 7.48(d); 7.64(d); 13.2(s). |
| 4.85 | $SO_2CH_3$ | $SO_2CH_3$ | H | O | H | H | $CH_2$ | OH | 3.25(s); 3.35(s); 3.44(t); 8.05(d); 8.45(d). |

The 3-heterocycly-substituted benzoyl derivatives of the formula I and their agriculturally useful salts are suitable as herbicides, both in the form of isomer mixtures and in the form of the pure isomers. The herbicidal compositions comprising compounds of the formula I effect very good control of vegetation on non-crop areas, especially at high rates of application. In crops such as wheat, rice, maize, soybeans and cotton they act against broad-leaved weeds and grass weeds without damaging the crop plants substantially. This effect is observed especially at low rates of application.

Depending on the application method in question, the compounds of the formula I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N.rustica), Olea europaea, Oryza sativa Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays*.

Moreover, the compounds of the formula I can also be used in crops which tolerate the action of herbicides due to breeding including genetic engineering methods.

The compounds of the formula I, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

The herbicidal compositions comprise a herbicidally active amount of at least one compound of the formula I or of an agriculturally useful salt of I and auxiliaries conventionally used for the formulation of crop protection products.

Suitable inert auxiliaries are essentially:

mineral oil fractions of medium to high boiling point such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone and water.

Aqueous use forms can be prepared from emulsion concentrates, suspensions, pastes, wettable powders or water-dispersible granules by adding water. To prepare emulsions, pastes or oil dispersions, the substrates [sic], as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants (adjuvants) are the alkali metal, alkaline earth metal and ammonium salts of aromatic sulfonic acids, eg. ligno-, phenol-, naphthalene- and dibutylnaphthalenesulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl, tributylphenyl polyglycol ether, alkylaryl polyether alcohols, isotridecyl alcohol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bolus, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the compounds of the formula I in the ready-to-use products can be varied within wide ranges. In general, the formulations comprise approximately from 0.001 to 98% by weight. preferably 0.01 to 95% by weight, of at least one active ingredient. The active ingredients are employed in a purity of from 90% to 100%, preferably 95% to 100% (according to NMR spectrum).

The formulation examples below illustrate the preparation of such products:

I. 20 parts by weight of the compound No. 3.2 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. 3.9 are dissolved in a mixture composed of 40 parts by weight of cyclohexanone, 30 parts-by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 3.10 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 3.16 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which compries 0.1% by weight of the active ingredient.

V. 3 parts by weight of the active ingredient No. 3.21 are mixed with 97 parts by weight of finely divided kaolin. This gives a dust which comprises 3% by weight of the active ingredient.

VI. 20 parts by weight of the active ingredient No. 3.22 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active ingredient No. 3.34 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of active ingredient No. 3.35 is dissolved in a mixture composed of 80 parts by weight of cyclohexanone and 20 parts by weight of Wettol$^R$ EM 31 (=nonionic emulsifier based on ethoxylated castor oil). This gives a stable emulsion concentrate.

The compounds of the formula I, or the herbicidal compositions comprising them, can be applied pre- or post-emergence. If the active ingredients are less well tolerated by certain crop plants, application techniques may be used in which the herbicidal compositions are sprayed, with the aid of the spray apparatus, in such a way that they come into as little contact as possible, if any, with the leaves of the sensitive crop plants while reaching the leaves of undesirable plants which grow underneath, or the bare soil (post-directed, lay-by).

Depending on the intended aim of the control measures, the season, the target plants and the growth stage, the application rates of the compound of the formula I are from 0.001 to 3.0, preferably 0.01 to 1.0 kg/ha of active substanz (a.s.).

To widen the spectrum of action and to achieve synergistic effects, the 3-heterocyclyl-substituted benzoyl derivatives of the formula I can be mixed and applied jointly with a large number of representatives of other groups of herbicidally or growth-regulatory active ingredients. Suitable components in mixtures are, for example, 1,2,4-thiadiazoles, 1,3,4-thiadiazoles, amides, aminophosphoric acid and its derivatives, aminotriazoles, anilides, aryloxy-/hetaryloxyalkanic acids and their derivatives, benzoic acid and its derivatives, benzothiadiazinones, 2-(hetaroyl/aroyl)-1,3-cyclohexandiones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofuranes, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolcarboxamides and uracils.

Moreover, it may be advantageous to apply the compounds of the formula I, alone or in combination with other herbicides, in the form of a mixture with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

USE EXAMPLES

The herbicidal action of 3-heterocyclyl-substituted benzoyl derivatives of the formula I was demonstrated by the following greenhouse experiments:

The culture containers used were plastic flowerpots containing loamy sand with approximately 3.0% of humus as substrate. The seeds of the test plants were sown separately for each species.

For the pre-emergence treatment, the active ingredients, suspended or emulsified in water, were applied directly after sowing by means of finely distributing nozzles. The containers were irrigated gently to promote germination and growth and subsequently covered with transparent plastic hoods until the plants had rooted. This cover causes [sic] uniform germination of the test plants unless this was adversely affected by the active ingredients.

For the post-emergence treatment, the test plants were grown to a plant height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to treatment. The rate of application for the post-emergence treatment was 31.2 or 15.6 g/ha a.s. (active substance).

Depending on the species, the plants were kept at from 10 to 25° C. and 20 to 35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific name | Common name |
| --- | --- |
| Chenopodium album | lambsquarters (goosefoot) |
| Setaria faberii | giant foxtail |
| Sinapsis alba | white mustard |
| Solanum nigrum | black nightshade |

-continued

| Scientific name | Common name |
| --- | --- |
| Triticum aestivum | winter wheat |
| Zea mays | Indian corn |

Compound 3.33 (Table 3) was very effective against the abovementioned mono- and dicotyledonous harmful plants and was well tolerated in winter wheat and maize when applied post-emergence at rates of application of 31.2 and 15.6 g/ha, respectively.

The invention claimed is:

1. A 3-heterocyclyl-substituted benzoic acid compound of formula III,

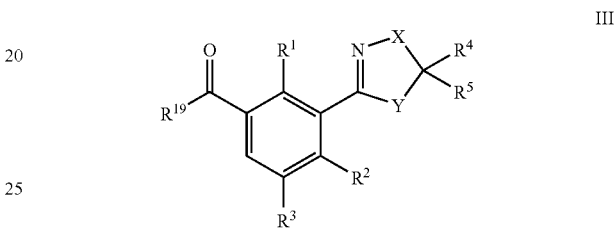

wherein:
R$^{19}$ is hydroxyl or a member selected from the group consisting of alkoxy, phenoxy, alkylthio and phenylthio radicals which are unsubstituted or substituted, halides, hetaryl radicals which are bonded via nitrogen; and amino, imino radicals which are unsubstituted or substituted, R$^1$, R$^2$ is nitro, halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl or $C_1$-$C_6$-haloalkylsulfonyl;

R$^3$ is hydrogen;

R$^4$ is halogen, nitro, $C_1$-$C_4$-alkyl, $C_1$-$C_4$-alkoxy-$C_1$-$C_4$-alkyl, $C_1$-$C_4$-alkoxycarbonyl-$C_1$-$C_4$-alkyl, $C_1$-$C_4$-alkylthio-$C_1$-$C_4$-alkyl, $C_1$-$C_4$-haloalkyl, $C_1$-$C_4$-cyanoalkyl, $C_3$-$C_8$-cycloalkyl, $C_1$-$C_4$-alkoxy, $C_1$-$C_4$-alkoxy-$C_2$-$C_4$-alkoxy, $C_1$-$C_4$-haloalkoxy, $C_1$-$C_4$-alkylthio, $C_1$-$C_4$-haloalkylthio, di($C_1$-$C_4$-alkyl)amino, COR$^6$, phenyl or benzyl, it being possible for the two last-mentioned substituents to be partially or fully halogenated and/or to have attached to them one to three of the following groups: nitro, cyano, $C_1$-$C_4$-alkyl, $C_1$-$C_4$-haloalkyl, $C_1$-$C_6$-alkoxy or $C_1$-$C_4$-haloalkoxy;

R$^5$ is $C_1$-$C_4$-alkyl;

R$^6$ is hydrogen, $C_1$-$C_4$-alkyl, $C_1$-$C_4$-haloalkyl, $C_1$-$C_4$-alkoxy, $C_1$-$C_4$-alkoxy-$C_2$-$C_4$-alkoxy, $C_1$-$C_4$-haloalkoxy, $C_3$-$C_6$-alkenyloxy, $C_3$-$C_6$-alkynyloxy or NR$^7$R$^8$;

X is O;

Y is CR$^{13}$R$^{14}$;

R$^{13}$, R$^{14}$ are hydrogen, $C_1$-$C_4$-alkyl, $C_1$-$C_4$-haloalkyl, $C_1$-$C_4$-alkoxycarbonyl, $C_1$-$C_4$-haloalkoxycarbonyl or CONR$^7$R$^8$;

R$^7$ is hydrogen or $C_1$-$C_4$-alkyl; and

R$^8$ is $C_1$-$C_4$-alkyl.

2. The 3-heterocyclyl-substituted benzoic acid compound of formula III defined in claim 1, wherein R$^{19}$ is halogen, hydroxyl or $C_1$-$C_6$-alkoxy.

3. A 3-heterocyclyl-substituted benzoyl compound of formula I

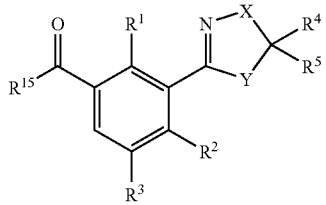

wherein:
X is O;
R$^1$, R$^2$ is nitro, halogen, cyano, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_1$-C$_6$-alkylsulfinyl, C$_1$-C$_6$-haloalkylsulfinyl, C$_1$-C$_6$-alkylsulfonyl or C$_1$-C$_6$-haloalkylsulfonyl;
R$^3$ is hydrogen;
R$^4$ is halogen, nitro, C$_1$-C$_4$-alkyl, C$_1$-C$_4$-alkoxy-C$_1$-C$_4$-alkyl, C$_1$-C$_4$-alkoxycarbonyl-C$_1$-C$_4$-alkyl, C$_1$-C$_4$-alkylthio-C$_1$-C$_4$-alkyl, C$_1$-C$_4$-haloalkyl, C$_1$-C$_4$-cyanoalkyl, C$_1$-C$_8$-cycloalkyl, C$_1$-C$_4$-alkoxy, C$_1$-C$_4$-alkoxy-C$_2$-C$_4$-alkoxy, C$_1$-C$_4$-haloalkoxy, C$_1$-C$_4$-alkylthio, C$_1$-C$_4$-haloalkylthio, di(C$_1$-C$_4$-alkyl)amino, COR$^6$, phenyl or benzyl, it being possible for the two last-mentioned substituents to be partially or fully halogenated and/or to have attached to them one to three of the following groups: nitro, cyano, C$_1$-C$_4$-alkyl, C$_1$-C$_4$-haloalkyl, C$_1$-C$_4$-alkoxy or C$_1$-C$_4$-haloalkoxy;
R$^5$ is C$_1$-C$_4$-alkyl;
R$^6$ is hydrogen, C$_1$-C$_4$-alkyl, C$_1$-C$_4$-haloalkyl, C$_1$-C$_4$-alkoxy, C$_1$-C$_4$-alkoxy-C$_2$-C$_4$alkoxy, C$_1$-C$_4$-haloalkoxy, C$_3$-C$_6$-alkenyloxy, C$_3$-C$_6$-alkynyloxy or NR$^7$R$^8$;
Y is CR$^{13}$R$^{14}$;
R$^{13}$, R$^{14}$ are hydrogen, C$_1$-C$_4$-alkyl, C$_1$-C$_4$-haloalkyl, C$_1$-C$_4$-alkoxycarbonyl, C$_1$-C$_4$-haloalkoxycarbonyl or CONR$^7$R$^8$;
R$^7$ is hydrogen or C$_1$-C$_4$-alkyl;
R$^8$ is C$_1$-C$_4$-alkyl;
R$^{15}$ is a pyrazole of the formula II which is linked in the 4-position

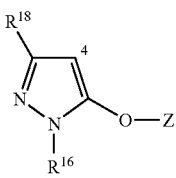

wherein
R$^{16}$ is methyl, ethyl, n-propyl or n-butyl;
Z is H or SO$^2$R$^{17}$;
R$^{17}$ is C$_1$-C$_4$-, C$_1$-C$_4$-haloalkyl, phenyl or phenyl which is partially or fully halogenated and/or has attached to it one to three of the following groups:
nitro, cyano, C$_1$-C$_4$-alkyl, C$_1$-C$_4$-haloalkyl, C$_1$-C$_4$-alkoxy or C$_1$-C$_4$-haloalkoxy; and
R$^{18}$ is hydrogen or methyl.

4. A composition comprising a herbicidally active amount of at least one 3-heterocyclyl-substituted benzoyl compound of formula I or of the agriculturally useful salt of formula I defined in claim 3, and auxiliaries conventionally used for the formulation of crop protection products.

5. A process for the preparation of the composition defined in claim 4, which comprises mixing a herbicidally active amount of at least one 3-heterocyclyl-substituted benzoyl compound of the formula I or of the agriculturally useful salt of I and auxiliaries conventionally used for the formulation of crop protection products.

6. A method of controlling undesirable vegetation, which comprises allowing a herbicidally active amount of at least one 3-heterocyclyl-substituted benzoyl compound of the formula I or of the agriculturally useful salt of I defined in claim 3 to act on plants, their environment and/or on seeds.

7. The 3-heterocyclyl-substituted benzoyl compound of the formula I defined in claim 3, wherein R$^1$ is methyl, R$^2$ is methylsulfonyl, R$^3$ is hydrogen, R$^{16}$ is methyl and R$^{18}$ is hydrogen.

8. The 3-heterocyclyl-substituted benzoyl compound of the formula I defined in claim 3, wherein R$^1$ is methyl, R$^2$ is methylsulfonyl, R$^3$ is hydrogen, R$^{16}$ is ethyl and R$^{18}$ is hydrogen.

9. The 3-heterocyclyl-substituted benzoyl compound of the formula I defined in claim 3, wherein R$^1$ is methyl, R$^2$ is methyl-sulfonyl, R$^3$ is hydrogen, R$^{16}$ is methyl and R$^{18}$ is methyl.

10. The 3-heterocyclyl-substituted benzoyl compound of the formula I defined in claim 3, wherein R$^1$ is methyl.

11. The 3-heterocyclyl-substituted benzoic acid compound of the formula III defined in claim 1, wherein R$^1$ is methyl.

12. The 3-heterocyclyl-substituted benzoic acid compound of the formula III defined in claim 2, wherein R$^1$ is methyl.

13. The 3-heterocyclyl-substituted benzoyl compound of the formula I defined in claim 3, wherein
X is O;
R$^1$ is C$_1$-C$_2$-alkyl;
R$^2$ is C$_1$-C$_6$-alkylthio or C$_1$-C$_6$-alkylsulfonyl;
R$^3$ is hydrogen;
Y is CR$^{13}$R$^{14}$; and
R$^{13}$, R$^{14}$ are hydrogen or C$_1$-C$_4$-alkyl.

14. The composition defined in claim 4, comprising a herbicidally active amount of at least one 3-heterocyclyl-substituted benzoyl compound of the formula I or of the agriculturally useful salt the formula of I, wherein
X is O;
R$^1$ is C$_1$-C$_2$-alkyl;
R$^2$ is C$_1$-C$_4$-alkylthio or C$_1$-C$_6$-alkylsulfonyl;
R$^3$ is hydrogen;
Y is CR$^{13}$R$^{14}$; and
R$^{13}$, R$^{14}$ are hydrogen or C$_1$-C$_4$-alkyl.

15. The 3-heterocyclyl-substituted benzoic acid compound of the formula III defined in claim 1, wherein
X is O;
R$^1$ is C$_1$-C$_2$-alkyl;
R$^2$ is C$_1$-C$_6$-alkylthio or C$_1$-C$_6$-alkylsulfonyl;
R$^3$ is hydrogen;
Y is CR$^{13}$R$^{14}$; and
R$^{13}$, R$^{14}$ are hydrogen or C$_1$-C$_4$-alkyl.

* * * * *